United States Patent
Edge et al.

(10) Patent No.: US 11,466,252 B2
(45) Date of Patent: Oct. 11, 2022

(54) EXPANSION AND DIFFERENTIATION OF INNER EAR SUPPORTING CELLS AND METHODS OF USE THEREOF

(71) Applicants: Massachusetts Eye and Ear Infirmary, Boston, MA (US); Decibel Therapeutics, Inc., Boston, MA (US)

(72) Inventors: Albert Edge, Brookline, MA (US); Michael Venuti, San Francisco, CA (US); Agnieszka Czechowicz, Stanford, CA (US)

(73) Assignees: Massachusetts Eye and Ear Infirmary, Boston, MA (US); Decibel Therapeutics, Inc., Boston, MA (US)

( * ) Notice: Subject to any disclaimer, the term of this patent is extended or adjusted under 35 U.S.C. 154(b) by 559 days.

(21) Appl. No.: 16/073,701

(22) PCT Filed: Jan. 27, 2017

(86) PCT No.: PCT/US2017/015379
§ 371 (c)(1),
(2) Date: Jul. 27, 2018

(87) PCT Pub. No.: WO2017/132530
PCT Pub. Date: Aug. 3, 2017

(65) Prior Publication Data
US 2019/0010449 A1 Jan. 10, 2019

Related U.S. Application Data

(60) Provisional application No. 62/288,958, filed on Jan. 29, 2016.

(51) Int. Cl.
| | |
|---|---|
| *C12N 5/0793* | (2010.01) |
| *C12N 5/071* | (2010.01) |
| *G01N 33/50* | (2006.01) |
| *A61P 43/00* | (2006.01) |
| *A61P 27/16* | (2006.01) |
| *A61K 31/506* | (2006.01) |
| *A61K 31/519* | (2006.01) |
| *A61K 31/55* | (2006.01) |
| *A61K 35/12* | (2015.01) |

(52) U.S. Cl.
CPC ............ *C12N 5/062* (2013.01); *A61K 31/506* (2013.01); *A61K 31/519* (2013.01); *A61K 31/55* (2013.01); *A61P 27/16* (2018.01); *A61P 43/00* (2018.01); *C12N 5/0625* (2013.01); *G01N 33/5044* (2013.01); *G01N 33/5058* (2013.01); *A61K 35/12* (2013.01); *C12N 2501/01* (2013.01); *C12N 2501/065* (2013.01); *C12N 2501/155* (2013.01); *C12N 2501/385* (2013.01); *C12N 2501/415* (2013.01); *C12N 2501/42* (2013.01); *C12N 2501/60* (2013.01); *C12N 2501/727* (2013.01); *C12N 2503/02* (2013.01); *C12N 2510/00* (2013.01)

(58) Field of Classification Search
CPC .... A61K 31/506; A61K 31/519; A61K 31/55; A61K 35/12; A61P 27/16; A61P 43/00; G01N 33/5044; G01N 33/5058; C12N 2501/01; C12N 2501/065; C12N 2501/155; C12N 2501/385; C12N 2501/415; C12N 2501/42; C12N 2501/60; C12N 2501/727; C12N 2503/02; C12N 2510/00; C12N 5/062; C12N 5/0625
See application file for complete search history.

(56) References Cited

U.S. PATENT DOCUMENTS

| | | |
|---|---|---|
| D309,535 S | 7/1990 | Wilson |
| D360,535 S | 7/1995 | Sjoberg |
| D447,031 S | 8/2001 | Oh |
| 6,417,185 B1 | 7/2002 | Goff et al. |
| 6,489,344 B1 | 12/2002 | Nuss et al. |
| 6,608,063 B2 | 8/2003 | Nuss et al. |
| 6,756,511 B2 | 6/2004 | Castro Pineiro et al. |
| 6,890,956 B2 | 5/2005 | Churcher et al. |
| 6,984,626 B2 | 1/2006 | Nadin et al. |

(Continued)

FOREIGN PATENT DOCUMENTS

| | | |
|---|---|---|
| CN | 1441841 | 9/2003 |
| JP | 2006-117536 | 5/2006 |

(Continued)

OTHER PUBLICATIONS

Bramhall et al., Stem Cell Reports, vol. 2 j 311-322, Mar. 11, 2014.*
Cheng et al., "Destabilization of Atoh1 by E3 Ubiquitin Ligase Huwel and Casein Kinase Is Essential for Normal Sensory Hair Cell Development," Journal of Biological Chemistry, Sep. 2016, 291(40):21096-21109.
Chim et al., "Deafness associated with the use of Bortezomib in multiple myeloma," Acta Oncologica, Jan. 2008, 47(2):323-324.

(Continued)

*Primary Examiner* — Erich A Leeser
(74) *Attorney, Agent, or Firm* — Fish & Richardson P.C.

(57) ABSTRACT

This disclosure relates to methods for expanding inner ear supporting cells (e.g., Lgr5+ inner ear supporting cells) and differentiating inner ear supporting cells (e.g., Lgr5+ inner ear supporting cells) to inner ear hair cells (e.g., atonal homolog 1 (Atoh1)+ inner ear hair cells) and the use of the inner hear supporting cells and hair cells, e.g., for identifying candidate therapeutic compounds for the treatment of hearing loss and balance loss. Additionally, the methods described herein can be used in the treatment of a subject having hearing loss and balance loss that would benefit from increased proliferation and differentiation of inner ear supporting cells (e.g., Lgr5+ inner ear supporting cells).

9 Claims, 6 Drawing Sheets
Specification includes a Sequence Listing.

(56) References Cited

U.S. PATENT DOCUMENTS

| | | | |
|---|---|---|---|
| 7,049,296 | B2 | 5/2006 | Castro Pineiro et al. |
| 7,101,895 | B2 | 9/2006 | Churcher et al. |
| 7,138,400 | B2 | 11/2006 | Collins et al. |
| 7,144,910 | B2 | 12/2006 | Madin et al. |
| 7,183,303 | B2 | 2/2007 | Castro Pineiro et al. |
| 7,206,639 | B2 | 4/2007 | Jacobsen et al. |
| 7,399,633 | B2 | 7/2008 | Bernstein et al. |
| D646,625 | S | 10/2011 | Youn |
| 8,188,069 | B2 | 5/2012 | Miller et al. |
| 8,518,944 | B2 | 8/2013 | Subramanyam et al. |
| 8,617,810 | B2 | 12/2013 | Heller et al. |
| 8,673,634 | B2 | 3/2014 | Li et al. |
| 10,406,163 | B2 | 9/2019 | Edge et al. |
| 10,603,295 | B2 | 3/2020 | Edge et al. |
| 10,925,872 | B2 | 2/2021 | Lorrain et al. |
| 2003/0114381 | A1 | 6/2003 | Cotanche et al. |
| 2004/0029862 | A1 | 2/2004 | Belanger et al. |
| 2004/0049038 | A1 | 3/2004 | Collins et al. |
| 2004/0186147 | A1 | 9/2004 | Hannam et al. |
| 2005/0019801 | A1 | 1/2005 | Rubin et al. |
| 2005/0119293 | A1 | 6/2005 | Collins et al. |
| 2005/0143369 | A1 | 6/2005 | Castro Pineiro et al. |
| 2005/0182109 | A1 | 8/2005 | Collins et al. |
| 2005/0182111 | A1 | 8/2005 | Pineiro et al. |
| 2005/0215602 | A1 | 9/2005 | Campbell et al. |
| 2005/0287127 | A1 | 12/2005 | Huawei et al. |
| 2006/0030837 | A1 | 2/2006 | McKenna et al. |
| 2007/0093878 | A1 | 4/2007 | Edge et al. |
| 2008/0146617 | A1 | 6/2008 | Aud et al. |
| 2008/0267929 | A1 | 10/2008 | Li et al. |
| 2009/0098093 | A1 | 4/2009 | Edge |
| 2009/0099237 | A1 | 4/2009 | And et al. |
| 2009/0124568 | A1 | 5/2009 | Heller et al. |
| 2009/0232780 | A1 | 9/2009 | Edge et al. |
| 2009/0297533 | A1 | 12/2009 | Lichter et al. |
| 2009/0306225 | A1 | 12/2009 | Lichter et al. |
| 2011/0020232 | A1 | 1/2011 | Eberhart et al. |
| 2011/0033480 | A1 | 2/2011 | Sarkar et al. |
| 2011/0305674 | A1 | 12/2011 | Edge et al. |
| 2013/0085112 | A1 | 4/2013 | Collard et al. |
| 2013/0210145 | A1 | 8/2013 | Edge |
| 2013/0225543 | A1 | 8/2013 | Jones et al. |
| 2014/0044763 | A1 | 2/2014 | Kustov et al. |
| 2015/0030568 | A1 | 1/2015 | Li et al. |
| 2015/0209406 | A1 | 7/2015 | Chen |
| 2019/0203210 | A1 | 7/2019 | Edge et al. |
| 2019/0247381 | A1 | 8/2019 | Edge et al. |
| 2020/0255800 | A1 | 8/2020 | Edge |
| 2021/0290686 | A1 | 9/2021 | Edge et al. |
| 2021/0299138 | A1 | 9/2021 | Edge et al. |

FOREIGN PATENT DOCUMENTS

| | | | |
|---|---|---|---|
| JP | | 2006/520386 | 9/2006 |
| JP | | 2007/503816 | 3/2007 |
| JP | | 2007/526248 | 9/2007 |
| JP | | 2011-518195 | 6/2011 |
| JP | | 2012-509899 | 4/2012 |
| WO | WO 1998/028268 | | 7/1998 |
| WO | WO 2000/053632 | | 9/2000 |
| WO | WO 2000/059939 | | 10/2000 |
| WO | WO 2001/070677 | | 9/2001 |
| WO | WO 2002/049038 | | 6/2002 |
| WO | WO 2003/093251 | | 11/2003 |
| WO | WO 2003/093252 | | 11/2003 |
| WO | WO 2003/093253 | | 11/2003 |
| WO | WO 2003/093264 | | 11/2003 |
| WO | WO 2004/039370 | | 5/2004 |
| WO | WO 2004/039800 | | 5/2004 |
| WO | WO 2005/014553 | | 2/2005 |
| WO | WO 2005/030731 | | 4/2005 |
| WO | WO 2006/026570 | | 3/2006 |
| WO | WO 2007/075911 | | 7/2007 |
| WO | WO 2008/076556 | | 6/2008 |
| WO | WO 2009/087130 | | 7/2009 |
| WO | WO 2009/132050 | | 10/2009 |
| WO | WO 2010/060088 | | 5/2010 |
| WO | WO 2012/005805 | | 1/2012 |
| WO | WO 2014/145205 | | 9/2014 |
| WO | WO 2014/159356 | | 10/2014 |
| WO | WO 2015/168149 | * 11/2015 | ............ A61K 38/12 |
| WO | WO 2016/022776 | | 2/2016 |
| WO | WO 2016/037016 | | 3/2016 |
| WO | WO 2017/151907 | | 9/2017 |
| WO | WO 2018/111926 | | 6/2018 |

OTHER PUBLICATIONS

D'Onofrio et al., "Advances in the identification of γ-secretase inhibitors for the treatment of Alzheimer's disease," Expert Opinion on Drug Discovery, Jan. 1, 2012, 7(1):19-37.

EP Office Action in European Appln. No. 17744987, dated May 14, 2020, 3 pages.

Fujioka et al, "SY3A-H5 A novel y-secretase inhibitor, LY411575, replaced auditory hair cells and recovered hearing loss after severe acoustic trauma in mice," Neurosci Res., 2008, 61(Suppl):S25.

Fujioka et al., "In vivo differentiation toward hair cell: A novel gamma-secretase inhibitor, LY411575, replaced auditory hair cells and ameliorated hearing impairment after severe acoustic trauma in mice," Presented at The 31st Annual Meeting of the Japan Neuroscience Society Symposium "Regeneration of Sensory Cells in the Inner Ear—From Bench to Bedside," Jul. 7, 2008, 30 pages.

JP Office Action in Japanese Appln. No. 2015-531223, dated Sep. 11, 2019, 5 pages (with English translation).

JP Office Action in Japanese Appln. No. 2019-091552, dated Apr. 28, 2020, 8 pages (with English translation).

Lee et al., "Proteasome inhibitors induce auditory hair cell death through peroxisome dysfunction," Biochem. Biophys. Res. Comm., 456(1):269-274.

Abbott et al., "Coordinated regulation of Toll-like receptor and NOD2 signaling by K63-linked polyubiquitin chains," Molecular and Cellular Biology, 2007, 27:6012-6025.

Adam et al., "Cell fate choices and the expression of Notch, Delta and Serrate homologues in the chick inner ear: parallels with *Drosophila* sense-organ development," Development, 125(23):4645-54 (Dec. 1998).

Adhikary et al., The ubiquitin ligase HectH9 regulates transcriptional activation by Myc and is essential for tumor cell proliferation, Cell, 2005, 123 :409-421.

Adler and Raphael "New hair cells arise from supporting cell conversion in the acoustically damaged chick inner ear," Neuroscience Letters, Feb. 1996, 205: 17-20.

Aletsee et al., "The disintegrin Kistrin inhibits neurite extension from spiral ganglion explants cultured on laminin," Audiol. Neurootol., 6:57-65 (2001).

Armstrong et al, "Porcine neural xenografts in the immunocompetent rat: immune response following grafting of expanded neural precursor cells," Neuroscience, Sep. 2001, 106(1):201-216.

Artavanis-Tsakonas et al., "Notch Signaling," Sci., 268: 225-232 (1995).

Barker et al, "A Role for Complement in the Rejection of Porcine Ventral Mesencephalic Xenografts in a Rat Model of Parkinson's Disease," The Journal of Neuroscience, May 2000, 20(9):3415-3424.

Barker et al., "Identification of stem cells in small intestine and colon by marker gene Lgf5," Nature, 2007, 449: 1003-1007.

Barker, "Wnt Signaling: vol. 1: Pathway Methods and Mammalian Models," in Methods in Molecular Biology, Nov. 2008, 5-15.

Bartolami et al., "Appearance and Distribution of the 275 kD Hair-Cell Antigen During Development of the Avian Inner Ear," J. Comp. Neurol., 314:777-788 (1991).

Basi et al., "Amyloid precursor protein selective gamma-secretase inhibitors for treatment Amyloid precursor protein selective gamma-secretase of Alzheimer's disease," Alzheimer's Research & Therapy, 2:36 (2010) pp. 1-21.

Batts et al., "Notch signaling and Hes labeling in the normal and drug-damaged organ of Corti," Hear Res., 249:15-22 (Mar. 2009).

(56) References Cited

OTHER PUBLICATIONS

Becvarovski et al., "Round Window Gentamicin Absorption: An In Vivo Human Model," Laryngoscope, Sep. 2002, 112: 1610-1613.
Ben-Arie et al., "Functional conservation of atonal and Math1 in the CNS and PNS," Development, 2000, 127:1039-1048.
Ben-Arie et al., Math1 is essential for genesis of cerebellar granule neurons. Nature, 19987, 390: 169-172.
Bermingham et al., "Math1: An Essential Gene for the Generation of Inner Ear Hair Cells," Science, 1999, 284: 1837-1841.
Bertrand et al., "Proneural genes and the specification of neural cell types," Nature Reviews Neuroscience, 2002, 3:517-530.
Beurel et al., "Glycogen synthase kinase-3 (GSIG): Regulation, actions, and diseases," Pharmacology & Therapeutics, 2015, 148:114-131.
Bodson et al., "Hair cell progenitors: identification and regulatory genes," Acta Otolaryngol, Mar. 2010, 130(3):312-7.
Bossuyt et al., "Atonal homolog 1 is a tumor suppressor gene," PLoS Biology, 2009, 7:e39.
Bouchard et al., "Pax2 and homeodomain proteins cooperatively regulate a 435 bp enhancer of the mouse Pax5 gene at the midbrain-hindbrain boundary," Develop., 127:1017-28 (2000).
Bramhall, "Lgr5-Positive Supporting Cells Generate New Hair Cells in the Postnatal Cochlea," Stem Cell Reports, Mar. 2014, 2:1-12.
Breuskin et al., "Strategies to regenerate hair cells: identification of progenitors and critical genes," Hear Res, 2008, 236(1-2):1-10.
Brooker et al., "Notch ligands with contrasting functions: Jagged1 and Delta1 in the mouse inner ear," Development, 2006,133:1277-1286.
Brors et al., "EphA4 Provides Repulsive Signals to Developing Cochlear Ganglion Neurites Mediated through Ephrin-B2 and-B3," J. Comp. Neurol., 462:90-100 (2003).
Bryant et al., "Sensory organ development in the inner ear: Molecular and cellular mechanisms," British Medical Bulletin, 63:39-57 (2002).
Burns and Stone, "Development and regeneration of vestibular hair cells in mammals," Semin Cell Dev Biol, 2017, 65:96-105.
Burns et al, "MYC Gene Delivery to Adult Mouse Utricles Stimulates Proliferation of Postmitotic Supporting Cells In Vitro," PLOS ONE, Oct. 2012, 7: 248704.
Burton et al., "The role of Pax2 in mouse inner ear development," Dev. Biol., 272:161-175 (2004).
Cafaro et al., "Atoh1 expression defines activated progenitors and differentiating hair cells during avian hair cell regeneration," Developmental dynamics, 2007, 236:156-170.
Cai et al., "Conditional deletion of Atoh1 reveals distinct critical periods for survival and function of hair cells in the organ of Corti," The Journal of Neuroscience, 2013, 10110-10122.
Caiazzo et al., "Direct generation of functional dopaminergic neurons from mouse and human fibroblasts," Nature, 476:224-7 (Jul. 2011).
CA Office Action in Canadian Appln. No. 2,883,896, dated Jul. 16, 2019, 4 pages.
Cau et al., "Mash1 activates a cascade of bHLH regulators in olfactory neuron progenitors," Develop., 124:1611-1621 (1997).
Chai et al., "Wnt signaling induces proliferation of sensory precursors in the postnatal mouse cochlea," PNAS, 2012, 109: 8167-8172.
Charron et al., "The Morphogen Sonic Hedgehog is an Axonal Chemoattractant that Collaborates with Netrin-1 in Midline Axon Guidance," Cell., 113:11-23 (2003).
Chen et al., "ARF-BPI/Mule is a critical mediator of the ARF tumor suppressor," Cell, 2005. 121: 1071-1083.
Chen et al., "The role of Math1 in inner ear development: Uncoupling the establishment of the sensory primordium from hair cell fate determination," Develop., 129:2495-2505 (2002).
Cheng, "Role of the Ubiquitin-Proteasome Pathway in the Inner Ear: Identification of an E3 Ubiquitin Ligase For Atoh1," Thesis for the Degree of Doctor of Philosophy in Health Sciences and Technology, Harvard—Massachusetts Institute of Technology, Aug. 29, 2014, 1-99.

Clevers, "Wnt/P-Catenin Signaling in Development and Disease," Cell, Nov. 2006, 127: 469-480.
Colter et al., "Rapid expansion of recycling stem cells in cultures of plastic-adherent cells from human bone marrow," Proc. Natl. Acad. Sci. U.S.A, 97:3213-3218 (2000).
Corrales et al., "Engraftment and Differentiation of Embryonic Stem Cell-Derived Neural Progenitor Cells in the Cochlear Nerve Trunk: Growth of Processes into the Organ of Corti," J. Neurobiol., 66:1489-500 (2006).
Corwin et al., "Regeneration of Sensory Hair Cells After Acoustic Trauma," Science, Jun. 1988, 240:1772-1774.
Cosgrove et al., Am J. Pathol., 157:1649-59 (2000).
Cox et al., "Spontaneous hair cell regeneration in the neonatal mouse cochlea in vivo," Development, 2014, 141: 816-829.
Crowder and Freeman, "Glycogen Synthase Kinase-3b Activity Is Critical for Neuronal Death Caused by Inhibiting Phosphatidylinositol 3-Kinase or Akt but Not for Death Caused by Nerve Growth Factor Withdrawal," The Journal of Biological Chemistry, Nov. 2000, 275: 34266-34271.
Dabdoub et al., "Abstract # 443: WNt/B-Catenin Signaling in the Developing Mammalian Cochlea," ARO 31st Annual Midwinter Meeting, Phoenix, Arizona, Feb. 16-21, 2008, 3 pages.
Dabdoub et al., "Abstract # 8: Wnt Signaling in the Developing Mammalian Cochlea,"ARO 30th Annual Midwinter Meeting, Denver, Colorado, Feb. 10-15, 2007, 2 pages.
D'Arca et al., "Huwe 1 ubiquitin ligase is essential to synchronize neuronal and glial differentiation in the developing cerebellum," PNAS, 2010, 107:5875-5880.
Daudet and Lewis, "Two contrasting roles for Notch activity in chick inner ear development: specification of pro sensory patches and lateral inhibition of hair-cell differentiation," Development, 132:541-51 (Feb. 2005).
Daudet et al., "Notch regulation of progenitor cell behavior in quiescent and regenerating auditory epithelium of mature birds," Dev Biol., 326(1):86-100 (Feb. 1, 2009).
Davis, "Hearing disorders in the population: first phase findings of the MRC National Study of Hearing," Hearing Science and Hearing Disorders, 1983, 35-60.
De Groot et al., "Huwel-mediated ubiquitylation of dishevelled defines a negative feedback loop in the Wnt signaling pathway," Science Signaling, Mar. 2014, 7:ra26.
Declaration of Non-Establishment of International Search Report for PCT/US2009/065747, dated Apr. 8, 2010.
Deshaies and Joazeiro, "RING domain E3 ubiquitin ligases," Annual Review of Biochemistry, 2009, 78:399-434.
Dezawa et al., "Specific induction of neuronal cells from bone marrow stromal cells and application for autologous transplantation," J. Clin. Invest., 113:1701-1710 (2004).
Doetzlhofer et al., "Hey2 regulation by FGF provides a Notch-independent mechanism for maintaining pillar cell fate in the organ of Corti," Dev Cell, 16:58-69 (Jan. 2009).
Dong et al., "Calpain inhibitor MDL28170 modulates $A\beta$ formation by inhibiting the formation of intermediate $A\beta_{46}$ and protecting $A\beta$ from degradation," The FASEB Journal, Dec. 2005, 21 pages.
Doyonnas et al., "Hematopoietic contribution to skeletal muscle regeneration by myelomoncytic precursors," Proc. Natl. Acad. Sci. U.S.A, 101:13507-13512 (2004).
Eatock and Rusch, "Developmental changes in the physiology of hair cells," Cell & Developmental Biology, 1997, 8:265-275.
Edge and Chen, "Hair cell regeneration," Curr Opin Neurobiol, 2008, 18: 377-382.
Edge et al., "Current Applications of Cellular Xenografts," Trans. Proc., 32:1169-1171 (2000).
Eng et al., "An approach to correlate tandem mass spectral data of peptides with amino acid sequences in a protein database," Journal of the American Society for Mass Spectrometry, 1994, 5:976-989.
EP Extended Search Report in EP Appln. No. 17744987.3, dated Jul. 3, 2019, 9 pages.
European Search Report in Application No. 13836099, dated Mar. 8, 2016, 9 Pages.
Examination Report issued in Australian Patent Application No. 2007334260 dated Aug. 23, 2012 (5 pages).

(56) References Cited

OTHER PUBLICATIONS

Extended European Search Report issued in corresponding European Patent Application No. 07871464.9, dated Nov. 17, 2010.
Extended European Search Report issued in EP 0982830, dated Dec. 7, 2012.
Final Office Action issued in U.S. Appl. No. 13/130,607 dated Oct. 21, 2013.
Flora et al., "Deletion of Atoh1 disrupts Sonic Hedgehog signaling in the developing cerebellum and prevents medulloblastoma," Science, 2009, 326:1424-1427.
Flora et al., "The E-protein Tcf4 interacts with Math 1 to regulate differentiation of a specific subset of neuronal progenitors," PNAS, 2007, 104: 15382-15387.
Forge et al., "Hair Cell Recovery in the Vestibular Sensory Epithelia of Mature Guinea Pigs," The Journal of Comparative Neurology, 1998, 397: 69-88.
Forge et al., "Ultrastructural evidence for hair cell regeneration in the mammalian inner ear," Science, 1993, 259: 1616-1619.
Forget et al., "Shh Signaling Protects Atohl from Degradation Mediated By The E3 Ubiquitin Ligase Huwel In Neural Precursors," Developmental Cell, Jun. 2014, 29: 649-661.
Frisina, "Age-related hearing loss: ear and brain mechanisms," Annals of the New York Academy of Sciences, 2009, 1170: 708-717.
Fritzsch et al., "Atoh1 Null Mice Show Directed Afferent Fiber Growth to Undifferentiated Ear Sensoiy Epithelia Followed by Incomplete Fiber Retention," Dev. Dyn., 233:570-583 (2005).
Fritzsch et al., "Lack of Neurotrophin 3 Causes Losses of Both Classes of Spiral Ganglion Neurons in the Cochlea in a Region-Specific Fashion," J. Neurosci., 17:6213-6225 (1997).
Fritzsch, "Development of inner ear afferent connections: forming primaly neurons and connecting them to the developing sensory epithelia," Brain Research Bulletin, 2003, 60:423-433.
Fujioka et al., "Manipulating cell fate in the cochlea: a feasible therapy for hearing loss," Trends Neurosci, 2015, 38: 139-144.
Gage, "Cell therapy," Nature, 392(6679 Suppl):18-24 (1998).
Gao et al., "mTOR drives its own activation via SCF(~TrCP)dependent degradation of the mTOR inhibitor DEPTOR," Molecular Cell, 2011, 44:290-303.
Gao et al., "Quantitative imaging of cochlear soft tissues in wild-type and hearingimpaired transgenic mice by spectral domain optical coherence tomography," Optics Express, 2011, 19:15415-15428.
Garapaty-Rao et al., "Identification of EZH2 and EZHI Small Molecule Inhibitors with Selective Impact on Diffuse Large B Cell Lymphoma Cell Growth," Chem. Biol, 2013, 20(11):1329-1339.
Geling et al., "A γ-secretase inhibitor blocks Notch signaling in vivo and causes a severe neurogenic phenotype in zebrafish," EMBO report, 2002, 688-694.
Gillespie et al., "LIF is more potent than BDNF in promoting neurite outgrowth of mammalian auditoiy neurons in vitro," Neuro. Rep., 12:275-279 (2001).
Golub et al., "Hair Cell Replacement in Adult Mouse Utricles after Targeted Ablation of Hair Cells with Diphtheria Toxin," The Journal of Neuroscience, Oct. 2012, 32: 15093-15105.
Gowan et al., "Crossinhibitory Activities of Ngnl and Mathl Allow Specification of Distinct Dorsal Interneurons," Neuron., 31:219-232 (2001).
Goycoolea and Lundman, "Round window membrane. Structure function and permeability: a review," Microsc Res Tech., 36:201-11 (Feb. 1, 1997).
Gregorieff and Clevers, "Wnt signaling in the intestinal epithelium: from endoderm to cancer," Genes & Development, 2005, 19:877-890.
Gubbels et al., "Functional auditory hair cells produced in the mammalian cochlea by in utero gene transfer," Nature, 2008, 455:537-541.
Guo et al., "Targeting the Notch signaling pathway in cancer therapeutics," Thoracic Cancer, 2014, 5: 473-486.

Haapasalo and Kovacs; "The Many Substrates of Presenilin/γ-Secretase" Journal Alzheimers Disease. 2011: 25(1): 3-28.
Hadland et al., "γ-secretase inhibitors repress thymocyte development," Proc Natl. Acad Sci USA, 98:7487-91 (Jun. 19, 2001).
Han and Shen, "Targeting γ-secretase in breast cancer," Breast Cancer: Targets and Therapy, 2012, 2012: 83-90.
Hartman et al., "Hes5 expression in the postnatal and adult mouse inner ear and the drug-damaged cochlea," J Assoc Res Otolaryngol., 10:321-40 (Sep. 2009).
Hawkins et al., "The developmental genetics of auditory hair cells," Hum. Mol. Genet., 13:R289-296 (2004).
Heller et al., "Parvalbumin 3 is an Abundant $Ca^{2+}$ Buffer in Hair Cells," J. Assoc. Res. Otolaryngol., 3:488-498 (2002).
Helms et al., "Autoregulation and multiple enhancers control Math1 expression in the developing nervous system," Develop., 127:1185-1196 (2000).
Helms et al., "Overexpression of MATH1 Disrupts the Coordination of Neural Differentiation in Cerebellum Development," Mol. Cell. Neurosci., 17:671-682 (2001).
Hendrickx & Leyns, "Non-conventional Frizzled ligands and Wnt receptors," Develop Growth Differ., 2008, 50:229-243.
Hermann et al., "Efficient generation of neural stem cell-like cells from adult human bone marrow stromal cells," J. Cell. Sci., 117:4411-4422 (2004).
Herold et al., "Mizl and HectH9 regulate the stability of the checkpoint protein, TopBPI," The EMBO Journal, 2008, 27:2851-2861.
Herzog et al., "Plasticity of marrow-derived stem cells," Blood, 102:3483-3493 (2003).
Hess et al., "Bone marrow-derived stem cells initiate pancreatic regeneration," Nat. Biotechnol., 21:763-770 (2003).
Hildebrand et al, "Advances in Molecular and Cellular Therapies for Hearing Loss," Molecular Therapy, 2008, 16(2):224-236.
Hirabayashi et al., "The Wnt/beta-catenin pathway directs neuronal differentiation of cortical neural precursor cells," Development, 2004, 131: 2791-2801.
Hosoya et al., "Method for efficient screening of substances inducing differentiation into inner ear hair cells with the use of spheres derived from inner ear cells," Otol Jpn, 2008, 18(4): 275 (with Englsih translation).
Hosoya et al., "An efficient screening method using inner-ear derived spheres for selection of compounds that induce hair cell differentiation," Neurosci Res., 61S:S57 Abstract, 2 pages (2008).
Hu and Ulfendahl, "Cell replacement therapy in the inner ear," Stem Cell and Development, 15:449-459 (2006).
Hu et al., "Neural cograft stimulates the survival and differentiation of embryonic stem cells in the adult mammalian auditory System,". Brain Research, 2005, 1051:137-144.
Hu et al., "Survival and neural differentiation of adult neural stem cells transplanted into the mature inner ear," Exper. Cell. Res., 302:40-47 (2005).
Huang et al., "Lysine 63-linked polyubiquitination is required for EGF receptor degradation," PNAS, 2013, 110: 15722-15727.
Huang, "Age-related hearing loss," Minn Med, 2007, 90(10):48-50.
Huawei et al., "Generation of hair cells by stepwise differentiation of embryonic stem cells," Proc. Natl. Acad. Sci. U.S.A., 23:13495-13500 (2003).
Huibregtse et al., A family of proteins structurally and functionally related to the E6-AP ubiquitin-protein ligase, PNAS, 19995, 92:5249.
Hume et al., "Expression of LHX3 and SOX2 during mouse inner ear development," Gene Expression Patterns, 2007, 7:798-807.
Husseman and Raphael, Gene therapy in the inner ear using adenovirus vectors. Advances in Oto-Rhino-Laryngology, 2009, 66:37-51.
Huynh et al., "The novel gamma secretase inhibitor RO4929097 reduces the tumor initiating potential of melanoma," PLoS One, 6(9):e25264, (2011) 10 pages.
Hyde et al., "Studies to investigate the in vivo therapeutic window of the γ-secretase inhibitor$N^2$-[(2S)-2-(3,5-difluorophenyl)-2-hydroxyethanoyl]-$N^1$-[(7S)-5-methyl-6-oxo-6,7-dihydro-5H-dibenzo[b,d]azepin-7-yl]-$_L$-alaninamide (LY411,575) in the CRND8 mouse," J Pharmacol Exp Ther., 319:1133-43 (Dec. 2006).

(56) References Cited

OTHER PUBLICATIONS

Ikeda and Dikic, "Atypical ubiquitin chains: new molecular signals. "Protein Modifications: Beyond the Usual Suspects" review series," EMBO Reports, 2008, 9:536-542.
Incesulu and Nadal, "Correlation of acoustic threshold measures and spiral ganglion cell survival in severe to profound sensorineural hearing loss: implications for cochlear implantation," The Annals of Otology, Rhinology, and Latyngology, 1998, 107:906-911.
Inoue et al., "Mule/Huwel/Arf-BPl suppresses Ras-driven tumorigenesis by preventing c-Myc/Mizl-mediated down-regulation ofp21 and p15," Genes & Development, 2013, 27: 1101-1114.
International Preliminary Report on Patentability for PCT/US2009/065747, dated May 24, 2011.
International Preliminary Report on Patentability in International Application No. PCT/US2013/058446, dated Mar. 10, 2015, 11 pages.
International Preliminary Report on Patentability in International Application No. PCT/US2016/064727, dated Jun. 14, 2018, 9 pages.
International Preliminary Report on Patentability in International Application No. PCT/US2017/015379, dated Aug. 9, 2018, 11 pages.
International Preliminary Report on Patentability issued in corresponding International Application No. PCT/US2007/084654, dated May 28, 2009.
International Search Report and Written Opinion in International Application No. PCT/US15/43976, dated Jan. 20, 2016, 16 pages.
International Search Report and Written Opinion in International Application No. PCT/US2013/058446, dated Dec. 26, 2013, 8 pages.
International Search Report and Written Opinion in International Application No. PCT/US2016/064727, dated May 1, 2017, 18 pages.
International Search Report and Written Opinion in International application No. PCT/US2017/015379, dated May 31, 2017, 18 pages.
International Search Report issued in corresponding International Application No. PCT/US2007/84654, dated Oct. 3, 2008.
Inuzuka et al., "SCFFBW7 regulates cellular apoptosis by targeting MCL1 for ubiquitylation and destruction," Nature, 2012, 470:104-109.
Ito et al., "Neurotrophins Facilitate Neuronal Differentiation of Cultmed Neural Stem Cells via Induction of mRNA Expression of Basic Helix-Loop-Helix Transcription Factors Mashl and Mathl," J. Neurosci. Res., 71:648-658 (2003).
Ivan et al., "HIFalpha targeted for VHL-mediated destruction by praline hydroxylation: implications for 02 sensing," Science, 2001,292:464-468.
Ivanov et al., "Genes required for *Drosophila* nervous system development identified by RNA interference," Proc. Nat. Acad. Sci., 101:16216-16221 (2004).
Izumikawa et al., "Auditory hair cell replacement and hearing improvement by Atohl gene therapy in deaf mammals," Nat Med., 11(3)271-6 (Mar. 2005).
Jaakkola et al., "Targeting ofHIF-alpha to the von Hippel-Lindau ubiquitylation complex by 02-regulated prolyl hydroxylation," Science, 2001, 292:468-472.
Jahan et al., "Beyond generalized hair cells: molecular cues for hair cell types," Hear Res, Mar. 2013, 297:30-41.
Jarriault et al., "Delta-1 Activation of Notch-1 Signaling Results in HES-1 Transactivation," Mol. Cell. Biol, 1998, 18:7423-7431.
Jarriault et al., "Signalling downstream of activated mammalian Notch," Nature, 1995, 377:355-358.
Jeon et al., "Notch Signaling Alters Sensory or Neuronal Cell Fate Specification of Inner Ear Stem Cells," J. Neurosci, 2011, 31: 8351-8358.
Jeon et al., "Bone marrow mesenchymal stem cells are progenitors in vitro for inner ear hair cells," Molecular and Cellular Neurosciences, 2007, 34:59-68.
Jiang et al., "Neuroectodermal differentiation from mouse multipotent adult progenitor cells," Proc. Natl. Acad. Sci .U.S.A, 100:11854-11860 (2003).
Jiang et al., "Pluripotency of mesenchymal stem cells derived from adult marrow," Nature, 418:41-49 (2002).
Jin et al., "Systematic analysis and nomenclature of mammalian F-box proteins," Genes Dev, 2004, 18(21):2573-2580.
JP Office Action in Japanese Appln. No. 2017-132839, dated Jun. 18, 2019, 10 pages with English translation).
Kaneko et al., "Musashi1: an evolutionarily conserved marker for CNS progenitor cells including neural stem cells," Dev Neurosci., 22:139-53 (2000).
Kawamoto et al., "Spontaneous hair cell regeneration in the mouse utricle following gentamicin ototoxicity," Hearing Research, 2009, 247: 17-26.
Kelley et al., "Regulation of cell fate in the sensory epithelia of the inner ear," Nat Rev Neurosci, 2006, 7: 837-849.
Kicic et al., "Differentiation of Marrow Stromal Cells into Photoreceptors in the Rat Eye," J. Neurosci., 23:7742-7749 (2003).
Kiernan et al., "Sox2 is required for sensory organ development in the mammalian inner ear," Nature, 434:1031-1035 (2005).
Kim et al., "Dopamine neurons derived from embryonic stem cells function in an animal model of Parkinson's disease," Nature, 418:50-6 (2002).
Kim et al., "NeuroD-null mice are deaf due to a severe loss of the inner ear sensory neurons during development," Develop., 128:417-426 (2001).
Klisch et al., "In vivo Atohl targetome reveals how a proneural transcription factor regulates cerebellar development," PNAS, 2011.
Knippschild et al., "The CK1 family: contribution to cellular stress response and its role in carcinogenesis," Frontiers in Oncology, May 2014, 4: 32 pages.
Knippschild et al., Metaanalysis to Estimate the Expected Drop Out-Rates Reported in Clinical Trials on Cataract Surgery, 2014, 231: 151-157 (with English abstract).
Kondo et al., "Sonic Hedgehog and retinoic acid synergistically promote sensory fate specification from bone marrow-derived pluripotent stem cells," Proc. Natl. Acad. Sci. U.S.A., 102(13):4789-4794 (Mar. 2005).
Kondo et al., "Wnt Signaling Promotes Neuronal Differentiation From Mesenchymal Stem Cells Through Activation ofTlx3," Stem Cells, 2011.
Kopan et al., "The Canonical Notch Signaling Pathway: Unfolding the Activation Mechanism," Cell, 2009, 137:216-233.
Kurokawa et al., "A network of substrates of the E3 ubiquitin ligases MDM2 and HUWEI control apoptosis independently ofp53," Science Signaling, 2013, 6:ra32.
Lanford et al., "Notch signalling pathway mediates hair cell development in mammalian cochlea," Nature Genetics, 21:289-292 (1999).
Lang et al., "Contribution of Bone Marrow Hematopoietic Stem Cells to Adult Mouse Inner Ear: Mesenchymal Cells and Fibrocytes," J .Comp. Neurol., 496:187-201 (2006).
Lanzoni et al., "MDL 28170 Attenuates Gentamicin Ototoxicity," Audiological Medicine, 2005, 3: 82-89.
Latres et al., "The human F box protein beta-Trcp associates with the Cull/Skpl complex and regulates the stability ofbeta-catenin," Oncogene, Jan. 1999, 18:849-854.
Ledent et al., "Phylogenetic analysis of the human basic helix-loop-helix proteins," Genome Biology, 2002 3:research0030.1.
Lee et al., "Efficient generation of midbrain and hindbrain neurons from mouse embryonic stem cells," Nat. Biotech., 18:675-9, (2000).
Lee et al., "EZH2 generates a methyl degron that is recognized by the DCAF1/DDB1/CUL4 E3 ubiquitin ligase complex," Molecular Cell, 2012, 48:572-586.
Leon et al.,. "Insulin-Like Growth Factor-I Regulates Cell Proliferation in the Developing Inner Ear, Activating Glycosyl-Phosphatidylinositol Hydrolysis and Fos Expression," Endocrinol., 136:3494-3503 (1995).
Li et al., "Correlation of Pax-2 Expression with Cell Proliferation in the Developing Chicken Inner Ear," J. Neurobiol., 60:61-70 (2004).
Li et al., "Generation of hair cells by stepwise differentiation of embryonic stem cells," Proc. Natl. Acad. Sci U.S.A., 100:13495-13500 (2003).

(56) References Cited

OTHER PUBLICATIONS

Li et al., "Pluripotent stem cells from the adult mouse inner ear," Nat. Med., 9:1293-1299 (2003).

Li et al., "Specification of motoneurons from human embryonic stem cells," Nat. Biotechnol., 23:215-21 (2005).

Li et al., "Stem cells as therapy for hearing loss," Trends Mol. Med., 10:309-315 (2004).

Lin et al., "Hair cell damage recruited Lgr5-expressing cells are hair cell progenitors in neonatal mouse utricle," Front Cell Neurosci, Apr. 2015, 9: 1-11.

Lin et al., "Inhibition of notch activity promotes non-mitotic regeneration of hair cells in the adult mouse utricles," J Neurosci., 31(43):15329-15339 (Oct. 26, 2011).

Lo et al., "Mammalian achaete-scute homolog 1 is transiently expressed by spatially restricted subsets of early neuroepithelial and neural crest cells," Genes & Development, 1991, 5: 1524-1537.

Loseva et al, "Comparison of reactive processes in the rat brain elicited by xenotransplantation of nervous tissues of chicken orpulmonate snail," Brain Research, 2001, 915:125-132.

Lu et al., "Abstract #: 774: The Influence of Glycogen Synthase Kinase 3 on Cell Proliferation in the Murine Vestibular Sensory Epithelium," ARO 31st Annual Midwinter Meeting, Phoenix, Arizona, Feb. 16-21, 2008, 3 pages.

Lu et al., "The Influence of Glycogen Synthase Kinase 3 in Limiting Cell Addition in the Mammalian Ear," Develop. Neurobiol., 68:1059-1075 (2008).

Luistro et al., "Preclinical Profile of a Potent γ-Secretase Inhibitor Targeting Notch Signaling with In vivo Efficacy and Pharmacodynamic Properties," Cancer Res, Oct. 2009, 69(19):7672-7690.

Lumpkin et al., "Math1-driven GFP expression in the developing nervous system of transgenic mice," Gene Expr Patterns, 3:389-95 (Aug. 2003).

Ma and Raible, "Signaling pathways regulating zebrafish lateral line development," Current Biology, 2009, 19:R381-386.

Ma et al., "Neurogenin 1 Null Mutant Ears Develop Fewer, Morphologically Normal Hair Cells in Smaller Sensory Epithelia Devoid of Innervation," Assoc. Res. Otolamyngol., 1:129-143 (2000).

Madisen et al., "A robust and high-throughput Cre reporting and characterization system for the whole mouse brain," Nat Neurosci, 2010, 13: 133-140.

Maksimovic et al., "Epidermal Merkel cells are mechanosensory cells that tune mammalian touch receptors," Nature, 2014, 509:617-621.

Mangi et al., "Mesenchymal stem cells modified with Akt prevent remodeling and restore performance of infarcted hearts," Nat. Med., 9:1195-201 (2003).

Markkanen et al., "Regulation of oxidative DNA damage repair by DNA polymerase A and MutYH by cross-talk of phosphorylation and ubiquitination," PNAS, 2012, 109:437-442.

Masuda et al., "Dual antitumor mechanisms of notch signaling inhibitor in a T-cell acute lymphoblastic leukemia xenograft model," Cancer Sci., 100(12):2444-2450 (Dec. 2009).

Matei et al., "Smaller Inner Ear Sensory Epithelia in Neurog1 Null Mice Are Related to Earlier Hair Cell Cycle Exit," Dev. Dyn., 234:633-50 (2005).

Matsui et al., "Regeneration and replacement in the vertebrate inner ear," Drug Discov. Today, 10:1307-12 (2005).

Matsuoka et al, In Vivo and In Vitro Characterization of Bone Marrow-Derived Stem Cells in the Cochlea, Laryngoscope, Aug. 2006, 116:1363-1367.

McLean et al, "Clonal Expansion of Lgr5-Positive Cells from Mammalian Cochlea and High-Purity Generation of Sensoiy Hair Cells," Cell Reports, Feb. 2017, 18(8):1917-1929.

Meierhofer et al., "Quantitative analysis of global ubiquitination in HeLa cells by mass spectrometiy," Journal of Proteome Research, 2008, 7:4566-4576.

Mezey et al., "Transplanted bone marrow generates new neurons in human brains," Proc. Natl. Acad. Sci. U.S.A., 100:1364-1369 (2003).

Miesegaes et al., "Identification and subclassification of new Atoh1 derived cell populations during mouse spinal cord development," Developmental Biology, Mar. 2009, 327:339-351.

Mikulec et al., "Permeability of the round window membrane is influenced by the composition of applied drug solutions and by common surgical procedures," Otol Neurotol., 29:1020-6 (Oct. 2008).

Mitani et al., "Differential Effects between γ-Secretase Inhibitors and Modulators on Cognitive Function in Amyloid Precursor Protein-Transgenic and Nontransgenic Mice," J. Neuroscience, Feb. 2012.

Mizutari et al., "Notch inhibition induces cochlear hair cell regeneration and recovery of hearing after acoustic trauma," Neuron, 2013, 77: 58-69.

Moon et al., "WNT and B-catenin signalling: diseases and therapies," Nature Reviews, Sep. 2004, 5: 689-699.

Morrison et al., "Mammalian Merkel cells are descended from the epidermal lineage," Developmental Biology, 2009, 336:76-83.

Murre et al., "Interactions between heterologous helixloop-helix proteins generate complexes that bind specifically to a common DNA sequence.," Cell, 1989, 58:537-544.

Murry et al., "Haematopoietic stem cells do not transdifferentiate into cardiac myocytes in myocardial infarcts," Nature., 428:664-668 (2004).

Nadol, Jr. et al., "Degenerative Changes in the Organ of Corti and Lateral Cochlear Wall in Experimental Endolymphatic Hydrops and Human Meniere's Disease," Acta Otolaryngol, 1995, Suppl 519: 47-59.

Naito Yasushi et al., "Transplantation of bone marrow stromal cells into the cochlea of chinchillas," NeuroReport, Lippincott Williams & Wilkins, 15:1-4 (2004).

Naujokat and Saric, "Concise review: role and function of the ubiquitinproteasome system in mammalian stem and progenitor cells," Stem Cells, 2007, 25 :2408-2418.

Non-Final Office Action issued in U.S. Appl. No. 13/130,607 dated Apr. 19, 2013.

Non-Final Office Action issued in U.S. Appl. No. 13/130,607 dated Oct. 23, 2014.

Notice of Opposition to European Patent in European Application No. 09828380.7, dated Jan. 11, 2018, 39 pages.

Noy et al., "HUWE1 ubiquitinates MyoD and targets it for proteasomal degradation," Biochemical and Biophysical Research Communications, 2012, 418:408-413.

Oesterle et al., "Sox2 and JAGGED1 expression in normal and drug-damaged adult mouse inner ear," J Assoc Res Otolaryngol., 9:65-89 (Mar. 2008).

Office Action in European Application No. 13836099.5, dated Jul. 25, 2018, 5 pages.

Office Action in Japanese Application No. 2015-178811, dated Jun. 5, 2018, 12 pages (with English translation).

Office Action in Japanese Application No. 2015-178811, dated Oct. 17, 2017, 6 pages (with English translation).

Office Action in Japanese Application No. 2015-531223, dated Jan. 15, 2019, 6 pages (with English translation).

Office Action in Japanese Application No. 2015-531223, dated Jul. 11, 2017, 8 pages (with English translation).

Office Action in Japanese Application No. 2015-531223, dated Jun. 19, 2018, 7 pages (with English translation).

Office Action in Japanese Application No. 2017-132839, dated Jun. 18, 2019, 7 pages (with English translation).

Office Action issued in AU2009316264 dated Jan. 16, 2015 (5 pages).

Office Action issued in CA2,669,693 dated Apr. 4, 2014 (4 pages).

Office Action issued in EP07871464.9 dated May 6, 2014 (5 pages).

Office Action issued in European Application No. 09828380.7 dated Mar. 26, 2014 (6 pages).

Office Action issued in Japanese Application No. 2011-537715 dated Feb. 4, 2014 (translation) 4 pages.

Office Action issued in JP2009-537328 dated Feb. 12, 2013 (7 pages).

Office Action issued in JP2011-537715 dated Jan. 20, 2015 with English translation (7 pages).

Office Action issued in JP2015-178811 dated Mar. 7, 2017 with English translation (5 pages).

(56) References Cited

OTHER PUBLICATIONS

Ohyama et al., "Wnt signals mediate a fate decision between otic placode and epidermis," Development, 2006, 133:865-875.

Okubo and Hogan, "Hyperactiye Wnt signaling changes the developmental potential of embiyonic lung endoderm," Journal of Biology, 2004, 3:11.

Oshima et al., "Differential distribution of stem cells in the auditory and vestibular organs of the inner ear," J Assoc Res Otolaryngol., 8:18-31 (Mar. 2007).

Oshima et al., "Mechanosensitive hair cell-like cells from embryonic and induced pluripotent stem cells," Cell, 2010, 141(4): 704-716.

Pagani et al., "Autologous Skeletal Myoblasts Transplanted to Ischemia-Damaged Myocardium in Humans," J. Am. Coll. Cardiol., 41:879-888 (2003).

Pan et al., "A novel Atohl "self-terminating" mouse model reveals the necessity of proper Atohl level and duration for hair cell differentiation and viability," PloS One, 2012, 7:e30358.

Pandya et al., "A structural element within the HUWE1 HECT domain modulates self-ubiquitination and substrate ubiquitination activities," The Journal of Biological Chemistry, 2010, 285:5664-5673.

Parker et al., "An independent construct for conditional expression of atonal homolog-1," Human Gene Therapy Methods, 2014, 25:1-13.

Parker et al., "Primary culture and plasmid electroporation of the murine organ of Corti," Journal of Visualized Experiments, 2010.

Parker, "Biotechnology in the treatment of sensorineural hearing loss: foundations and future of hair cell regeneration," Journal of Speech, Language, and Hearing Research, 2011, 54: 1 709-1731.

Patzel et al., "Design of siRNAs producing unstructured guide-RNAs results in improved RNA interference efficiency," Nature Biotechnol., 23:1440-1444 (2005).

Pauley et al., "Expression and Function of FGF10 in Mammalian Inner Ear Development," Dev. Dyn., 227:203-215 (2003).

Pedersen, "Cells for Medicine," Scientif. Am., 280:68-73 (1999).

Peng et al., "A proteomics approach to understanding protein ubiquitination," Nature Biotechnology, 2003, 21:921-926.

Petit, "Usher syndrome: from genetics to pathogenesis," Annu Rev Genomics Hum Genet., 2:271-97 (2001).

Pickart, "Ubiquitin enters the new millennium," Molecular Cell, Sep. 2001, 8(3):499-504.

Pirvola et al., "Neurotrophic Factors during Inner Ear Development," Curr. Top. Dev. Biol., 57:207-223 (2003).

Pittenger et al., "Multilineage Potential of Adult Human Mesenchymal Stem Cells," Sci., 284:143-147 (1999).

Plum et al., "Connexin31-deficiency in mice causes transient placental dysmorphogenesis but does not impair hearing and skin differentiation," Dev Biol., 231:334-47 (2001).

Presente et al., "Notch is required for long-term memory in *Drosophila*," Proc. Nat. Acad. Sci., 101:1764-1768 (2004).

Price, "CKI, there's more than one: casein kinase I family members in Wnt and Hedgehog signaling," Genes & Development, 20: 399-410.

Purow et al., "Expression of Notch-1 and Its Ligands, Delta-Like-1 and Jagged-1, Is Critical for Glioma Cell Survival and Proliferation," Cancer Res., 65:2353-2363 (2005).

Qyang et al., "The renewal and differentiation of Isl 1 + cardiovascular progenitors are controlled by a Wnt/beta-catenin pathway," Cell Stem Cell, 2007, 1: 165-179.

Rask-Andersen et al., "Regeneration of human auditory nerve. In vitro/in video demonstration of neural progenitor cells in adult human and guinea pig spiral ganglion," Hear. Res., 203:180-191 (2005).

Ravid and Hochstrasser, "Diversity of degradation signals in the ubiquitin-proteasome system," Nat Rev Mol Cell Biol, 2008, 9(9):679-90.

RCE and Response to Final Office Action issued in U.S. Appl. No. 13/130,607, filed Apr. 21, 2014.

Rena et al., "D4476, a cell-permeant inhibitor of CKI, suppresses the site-specific phosphorylation and nuclear exclusion of FOXOIa," EMBO reports, 2004, 5: 60-65.

Response to Non-Final Office Action issued in U.S. Appl. No. 13/130,607, filed Jul. 19, 2013.

Response to Non-Final Office Action issued in U.S. Appl. No. 13/130,607 dated Oct. 23, 2014, filed Apr. 23, 2015 (10 pages).

Response to Restriction Requirement issued in U.S. Appl. No. 13/130,607, filed Dec. 12, 2012.

Response to Restriction Requirement issued in U.S. Appl. No. 13/759,441 dated Dec. 22, 2014, filed Mar. 19, 2015 (4 pages).

Response to U.S. Final Office Action in U.S. Appl. No. 13/130,607, dated Jan. 15, 2016.

Restriction Requirement issued in U.S. Appl. No. 13/130,607 dated Oct. 12, 2012.

Restriction Requirement issued in U.S. Appl. No. 13/759,441 dated Dec. 22, 2014 (4 pages).

Riccomagno et al., "Wnt-dependent regulation of inner ear morphogenesis is balanced by the opposing and supporting roles of Shh," Genes & Development, 2005, 19: 1612-1623.

Roberson et al., "Direct transdifferentiation gives rise to the earliest new hair cells in regenerating avian auditory epithelium," Journal of Neuroscience Research, 2004,7 8: 461-4 71.

Roccio et al., "Cell cycle reactivation of cochlear progenitor cells in neonatal FUCCI mice by a GSK3 small molecule inhibitor," Sci Rep, Dec. 2015, 5: 1-11.

Ross et al., "Basic helix-loop-helix factors in cortical development," Neuron, Jul. 2003, 39: 13-25.

Rotin and Kumar, "Physiological functions of the HECT family ofubiquitin Ligases," Nature Reviews Molecular Cell Biology, 2009, 10:398-409.

Rubel et al., "Mammalian Vestibular Hair Cell Regeneration," Science, Feb. 1995, 267(5198):701-707.

Ryals and Rubel, "Hair Cell Regeneration After Acoustic Trauma in Adult Cotumix Quail," Science, Jun. 1988, 240:1774-1776.

Ryusuke et al., "Pharmacological inhibition of Notch signaling in the mature guinea pig cochlea" Neuroreport, Lippincott Williams and Wilkins, UK, Dec. 2007, 18(18): 1911-1914.

Sakaguchi et al., "Spatiotemporal patterns of Musashil expression during inner ear development," Neuroreport, 15:997-1001 (Apr. 29, 2004).

Sakamoto et al., "Fates of mouse embryonic stem cells transplanted into the inner ears of adult mice and embiyonic chickens," Acta Otolarynol Suppl., 551:48-52 (2004).

Salt and Plontke, "Principles of local drug delivery to the inner ear," Audiol Neurootol., 14:350-60 (2009).

Samon et al., "Preclinical analysis of the γ-secretase inhibitor PF-03084014 in combination with glucocorticoids in T-cell acute lymphoblastic leukemia," Mol Cancer Ther., 11(7):1565-1575 (Jul. 2012).

Samstein an Platt, "Physiologic and immunologic hurdles to xenotransplantation," Journal of American Society of Nephrology, 12:182-193 (2001).

Sarrazin et al., "Proneural gene requirement for hair cell differentiation in the zebrafish lateral line," Dev. Biol., 295:534-545 (2006).

Satoh and Fekete, "Clonal analysis of the relationships between mechanosensory cells and the neurons that innervate them in the chicken ear," Develop., 132:1687-1697 (2005).

Scheffner and Staub, "HECT E3s and human disease," BMC Biochemistry, Nov. 2007, 8 Suppl 1:S6.

Schwarz et al., "Characterization of human hect domain family members and their interaction with UbcH5 and UbcH7," The Journal of Biological Chemistiy, 1998, 273: 12148-12154.

Shakoori et al., "Deregulated GSK3b activity in colorectal cancer: Its association with tumor cell survival and proliferation," Biochem and Biophys Research Comm, 2005, 334: 1365-1373.

Shi et al., "Abstract #: 732: Interaction of B-Catenin with an Atohl 3' Enhancer Upregulates Atohl Expression and Increases Differentiation of Progenitors to Hair Cells," ARO 32nd Annual Midwinter Meeting, Baltimore, Maiyland, Feb. 14-19, 2009, 3 pages.

Shi et al., "Generation of hair cells in neonatal mice by beta-catenin overexpression in Lgr5-positive cochlear progenitors," PNAS, 2013, 110: 13851-13856.

(56) References Cited

OTHER PUBLICATIONS

Shi et al., "β-Catenin Up-regulates Atohl Expression in Neural Progenitor Cells by Interaction with an Atohl 3' Enhancer," J Biol Chem, 2010, 285: 392-400.
Shi et al., Wnt-responsive Lgr5-expressing stem cells are hair cell progenitors in the cochlea. The Journal of Neuroscience, 2012, 32:9639-9648.
Shi et al., "β-Catenin Is Required for Hair-Cell Differentiation in the Cochlea," The Journal of Neuroscience, 2014, 34:6470-6479.
Skowyra et al., "F-box proteins are receptors that recruit phosphorylated substrates to the SCF ubiquitin-ligase complex," Cell, 1997, 91:209-219.
Sowa et al., "Defining the human deubiquitinating enzyme interaction landscape," Cell, 2009, 138:389-403.
Sparling et al., "Adipocyte-specific blockade of gamma-secretase, but not inhibition of Notch activity, reduces adipose insulin sensitivity," Molecular Metabolism, 2016, 5: 113-121.
Spence et al., "A ubiquitin mutant with specific defects in DNA repair and multiubiquitination," Molecular and Cellular Biology, 1995, 15:1265-1273.
Staecker et al., "Vestibular hair cell regeneration and restoration of balance function induced by math1 gene transfer," Otology & Neurotology, 2007, 28:223-231.
Stahle et al., "Long-term Progression of Meniere's Disease," Acta Otolaryngol, 1991, Suppl. 485: 78-83.
Stallwood et al., "Small Interfering RNA-Mediated Knockdown of Notch Ligands in Primary CD4+ T Cells and Dendritic Cells Enhances Cytokine Production," J. Immunol., 177:885-895 (2006).
Stambolic et al., "Lithium inhibits glycogen synthase kinase-3 activity and mimics Wingless signalling in intact cells," Current Biology, 1996, 6: 1664-1668.
Stevens et al., "Forced activation of Wnt signaling alters morphogenesis and sensory organ identity in the chicken inner ear," Dev. Biol, 2003, 261: 149-164.
Stone and Cotanche, "Identification of the timing of S phase and the patterns of cell proliferation during hair cell regeneration in the chick cochlea," The Journal of Comparative Neurology 341:50-67.
Sumitran et al, "Porcine Embryonic Brain Cell Cytotoxicity Mediated by Human Natural Killer Cells," Cell Transplantation, 1999, 601-610.
Supplementary European Search Report issued in EP09828380 dated Nov. 30, 2012 (8 pages).
Swan et al., "Inner ear drug delivery for auditory applications," Advanced Drug Delivery Reviews, 2008, 60: 1583-1599.
Tai and Schuman, "Ubiquitin, the proteasome and protein degradation in neuronal function and dysfunction," Nature Reviews Neuroscience, 2008, 9:826-838.
Takebayashi et al., "Multiple roles of Notch signaling in cochlear development," Developmental Biology, 2007, 307: 165-178.
Tan et al., "Parallel SCF adaptor capture proteomics reveals a role for SCFFBXL17 in NRF2 activation via BACH1 repressor turnover," Molecular Cell, 2013, 52:9-24.
Tiveron et al., "Role of Phox2b and Mash1 in the generation of the vestibular efferent nucleus," Developmental Biology, 2003, 260:46-57.
Tsuchiya et al., "Reciprocal targeting of Hath1 and beta-catenin by Wnt glycogen synthase kinase 3beta in human colon cancer," Gastroenterology, 2007, 132:208-220.
U.S. Final Office Action in U.S. Appl. No. 13/130,607, dated Jan. 15, 2016, 26 pages.
Varshavsky, "Naming a targeting signal," Cell, 1991, 64:13-15.
Vats et al, "Stem cells: sources and applications," Clin. Otoaryngol, 27:227-232.
Vierbuchen et al., "Direct conversion of fibroblasts to functional neurons by defined factors," Nature, 463:1035-41 (Feb. 25, 2010).
Wagers et al., "Little Evidence for Developmental Plasticity of Adult Hematopoietic Stem Cells," Science, 297:2256-2259 (2002).
Wagner and Jung, "New lysine methyltransferase drug targets in cancer," Nature Biotechnology, 2012, 30:622-623.

Wang et al., "Cell fusion is the principal source of bone-marrow-derived hepatocytes," Nature, 422:897-901 (2003).
Wang et al., "Dynamics of noise-induced cellular injury and repair in the mouse cochlea," J Assoc Res Otolaryngol., 3:248-68 (Sep. 2002).
Wang et al., "HUWE1 interacts with BRCA1 and promotes its degradation in the ubiquitin-proteasome pathway," Biochemical and Biophysical Research Communications, 2013.
Warchol et al., "Regenerative proliferation in inner ear sensory epithelia from adult guinea pigs and humans," Science, 1993, 259: 1619-1622.
Warner et al., "Expression of ZIC Genes in the Development of the Chick Inner Ear and Nervous System," Dev. Dyn., 226:702-712 (2003).
Weimann et al., "Contribution of transplanted bone marrow cells to Purkinje neurons in human adult brains," Proc. Natl. Acad. Sci. U.S.A., 100:2088-2093 (2003).
White et al., "Mammalian cochlear supporting cells can divide and trans-differentiate into hair cells," Nature, 441:984-987 (2006).
Wolfe, "γ-secretase Inhibition and Modulation for Alzheimer's Disease," Curr Alzheimer Res., 5(2):158-164 (Apr. 2008) (Author Manuscript).
Wong et al., "Chronic treatment with the gamma-secretase inhibitor L Y-411,575 inhibits beta-amyloid peptide production and alters lymphopoiesis and intestinal cell differentiation," J Biol Chem., 279:12876-82 (Mar. 26, 2004).
Woods et al., "Math1 regulates development of the sensory epithelium in the mammalian cochlea," Nat. Neurosci., 7:1310-1318 (2004).
Written Opinion of the International Searching Authority for PCT/US2009/065747, dated Apr. 8, 2010.
Written Opinion of the International Searching Authority issued in corresponding International Application No. PCT/US2007/84654, dated Oct. 3, 2008.
Wu et al., "Structure of a beta-TrCP 1-Skp 1-beta-catenin complex: destruction motif binding and lysine specificity of the SCF(beta-TrCP 1) ubiquitin ligase," Molecular Cell, 2003, 11:1445-1456.
Yamamoto et al., "Inhibition of Notch/RBP-J signaling induces hair cell formation in neonate mouse cochleas," J. Mol. Med., 84(1):37-45 (Jan. 2006).
Yang et al., "E3 ubiquitin ligase Mule ubiquitinates Miz1 and is required for TNFalphainduced JNK activation," PNAS, 2010, 107:13444-13449.
Yang et al., "Generation and characterization of Atoh1-Cre knock-in mouse line," Genesis, 2010, 48:407-413.
Yang et al., "Requirement of Math 1 for Secretory Cell Lineage Commitment in the Mouse Intestine," Science, 2001, 294:2155.
Ye et al., "Recognition of phosphodegron motifs in human cyclin E by the SCF(Fbw7) ubiquitin ligase," The Journal of biological chemistly, 2004, 279:50110-50119.
Zaragosi et al., "Effects of GSK3 inhibitors on in vitro expansion and differentiation of human adipose-derived stem cells into adipocytes," BMC Cell Biology, 2008, 9: 11.
Zhang et al., "Gene regulatory networks mediating canonical Wnt signal-directed control of pluripotency and differentiation in embryo stem cells," Stem Cells, 2013, 31(12):2667-79.
Zhang et al., "Mule determines the apoptotic response to HDAC inhibitors by targeted ubiquitination and destruction of HDAC2," Genes & Development, 2011, 25:2610-2618.
Zhao et al., "The HECT-domain ubiquitin ligase Huwe1 controls neural differentiation and proliferation by destabilizing the N-Myc oncoprotein," Nature Cell Biology, 2008, 10:643-653.
Zhao et al., "The N-Myc-DLL3 cascade is suppressed by the ubiquitin ligase Huwe1 to inhibit proliferation and promote neurogenesis in the developing brain," Developmental Cell, 2009, 17:210-221.
Zheng and Gao, "Overexpression of Math1 induces robust production of extra hair cells in postnatal rat inner ears," Nat. Neurosci., 2000, 3:580-586.
Zheng et al., "Induction of Cell Proliferation by Fibroblast and Insulin-Like Growth Factors in Pure Rat Inner Ear Epithelial Cell Cultures," J. Neurosci., 17:216-226 (1997).

(56) References Cited

OTHER PUBLICATIONS

Zhong et al., "Mule/ARF-BP1, a BH3-only E3 ubiquitin ligase, catalyzes the polyubiquitination of Mcl-1 and regulates apoptosis," Cell, 2005, 21:1085-1095.

Zine et al., "Hes1 and Hes5 activities are required for the normal development of the hair cells in the mammalian inner ear," J Neurosci., 21:4712-20 (Jul. 1, 2001).

Zine et al., "Notch signaling regulates the pattern of auditory hair cell differentiation in mammals," Development., 2000, 127:3373-3383.

CA Office Action in Canadian Appln. No. 2,883,896, dated Apr. 1, 2021, 4 pages.

EP Brief Communication in European Appln. No. 13836099.5, dated Jan. 19, 2021, 9 pages.

Feng et al., "Blocking caspase-3-dependent pathway preserves hair cells from salicylate-induced apoptosis in the guinea pig cochlea," Mol Cell Biochem., 2011, 353:291-303.

JP Office Action in Japanese Appln. No. 2015-531223, dated Jan. 5, 2021, 20 pages (with English translation).

JP Office Action in Japanese Appln. No. 2018-540010, dated Mar. 2, 2021, 6 pages (with English translation).

JP Office Action in Japanese Appln. No. 2018-540010, dated Sep. 21, 2021, 5 pages (with English translation).

JP Office Action in Japanese Appln. No. 2019-228284, dated Jan. 26, 2021, 5 pages (with English translation).

JP Office Action in Japanese Appln. No. 2020-180340, dated Jul. 6, 2021, 10 pages (with English translation).

Li et al., "Round Window Membrane Delivery of L-Methionine Provides Protection from Cisplatin Ototoxicity Without Compromising Chemotherapeutic Efficacy," NeuroToxicology, 2001, 22:163-176.

Nakagawa, "Aiming for the treatment of inner ear diseases—the forefront of basic research," Bulletin of the Japan Otolaryngology Society, 2008, 11(10):655-663 (with machine abstract).

Sziklai et al., "Otosclerosis: an organ-specific inflammatory disease with sensorineural hearing loss," Eur. Arch. Otorhinolaryngol., 2009, 266:1711-1718.

Xia et al., "Ototoxicity of cisplatin administered to guinea pigs via the round window membrane," J Toxicol Sci., 2012, 37(4):823-830.

Yang et al., "EGb 761 (Ginkgo biloba) protects cochlear hair cells against ototoxicity induced by gentamicin via reducing reactive oxygen species and nitric oxide-related apoptosis," J Nutr Biochem., 2011, 22:886-894.

Yoneda, "Attempt to regenerate cochlear morphology and function using gene transfer," Otol. Jpn., May 2006, 16(2):135-138 (with machine translation).

Extended European Search Report in European Appln No. 21190313.3, dated Feb. 16, 2022, 11 pages.

Extended European Search Report in European Appln No. 21181586.5, dated Nov. 26, 2021, 8 pages.

Office Action in Canadian Appln. No. 2,883,896, dated Dec. 13, 2021, 4 pages.

Office Action in Chinese Appln. No. 201780017058.9, dated Nov. 15, 2021, 12 pages (English translation).

Office Action in Japanese Appln. No. 2020-180340, dated Dec. 21, 2021, 10 pages (with English Translation).

Notice of Allowance in Japanese Appln. No. 2018-540010, dated Apr. 18, 2022, 6 pages (with English translation).

\* cited by examiner

SEQUENCE LISTING

<160> NUMBER OF SEQ ID NOS: 2

<210> SEQ ID NO 1
<211> LENGTH: 1397
<212> TYPE: DNA
<213> ORGANISM: Artificial Sequence
<220> FEATURE:
<223> OTHER INFORMATION: Atoh1 enhancer

<400> SEQUENCE: 1

```
tccaaggtcc ggcaatgaag tttgcataac aaacgtttgg cagctccctc tctcacaccc        60
cattaacaag ctgtaacata tagctgcagg ttgctataat ctcattaata tttttggaaac      120 ttgaatattg agtatttctg agcgctcatt ccccatatgc cagaccactc ctgccatgct       180
gactggttcc tttctctcca ttattagcaa ttagcttcta ccttccaaag tcagatccaa       240
gtatctaaga tactaccaaa ggcatcaact atgtatgcaa gttaggcatg cttaatatca       300
cccaaacaaa caaagagtca gcacttctta aagtaatgaa gatagataaa tcgggttagt       360
tctttgggac accgctgttg ttttccagag tttttctata cttaagcag cttgttttat        420 attctgtctt tgccctcagc cagctaacat tttatttgtt gagggttttg gctcaccaca       480
```

```
cttttggaaaa cttatttgat ttcacgggga gctgaaggaa gattgttttt ggcaacaggc    540
aagtttaaca cgttcttcat ggggcattgc gaatggcaca tctaccagaa agggaggggg    600
agtaacttcc tcgtgctgaa ccagcaggag accagagctt tcctgaggtc ttcctattga    660
ttttaaagat ttaaaactga gccccaaagt tgtaatgtta ttgaagtttg tcttggaata    720
tacatctcct ctgctaactt aaaagttcaa gaaaggaaag gaaagaaata gaacccttg     780 ctaactacaa cctagactga gaggtgaaga tcgcgggcaa agacaggtgg tcactgaaac    840
gtttgcagtt ctttcttcc gaaggcttag gacacagggt aaggaggagc taaaataaag     900
ccgagtgtac gtttagtctt ctctgcaccc caggcctagt gtctcccag gcaaggagtc     960 accccctttg cttctggctc taactgaaa aaggcaaaag ggagtggaga atgggttaaa    1020
tcccaggaca caggggagag gcaggggagg agagaagtcg gaggaagata aaggaagga    1080 caggaaccaa gaagcgtggg ggtagtttgc cgtaatgtga gtgtttctta attagagagc    1140
ggctgacaat agaggggctg gcagaggctc ctggccccgg tgcggagcgt ctggagcgga    1200
gcacgcgctg tcagctggtg agcgcactcg cttttcaggcc gctccccggg gagctgagcg    1260
gccacattta acaccgtcgt caccctcccc ggcctcctca acatcggcct cctcctcgta    1320
gacagccttg ctcggccccc caccggcaga gtttacagaa gccagagcct ctcgccgttc    1380
ccccgcattc gcccggg                                                  1397

<210> SEQ ID NO 2
<211> LENGTH: 5236
<212> TYPE: DNA
<213> ORGANISM: Artificial Sequence
<220> FEATURE:
<223> OTHER INFORMATION: Atoh1-mCherry plasmid

<400> SEQUENCE: 2
ggtaccgagc tcttacgcgt gctagcccgg gctcgagatc ttccaaggtc cggcaatgaa     60
gtttgcataa caaacgtttg gcagctccct ctctcacacc ccattaacaa gctgtaacat    120
atagctgcag gttgctataa tctcattaat atttttggaaa cttgaatatt gagtatttct    180
gagcgctcat tccccatatg ccagaccact cctgccatgc tgactggttc ctttctctcc    240
attattagca attagcttct accttccaaa gtcagatcca agtatctaag atactaccaa    300
aggcatcaac tatgtatgca agttaggcat gcttaatatc acccaaacaa acaaagagtc    360
agcacttctt aaagtaatga agatagataa atcgggttag ttctttggga caccgctgtt    420
gttttccaga gttttctat actttaagca gcttgtttta tattctgtct ttgccctcag    480
ccagctaaca ttttatttgt tgagggtttt ggctcaccac acttttggaa acttatttga    540
tttcacgggg agctgaagga agattgtttt tggcaacagg caagtttaac acgttcttca    600
tggggcattg cgaatggcac atctaccaga aagggagggg gagtaacttc ctcgtgctga    660
accagcagga gaccagagct ttcctgaggt cttcctattg attttaaaga tttaaaactg    720
agccccaaag ttgtaatgtt attgaagttt gtcttggaat atacatctcc tctgctaact    780
taaaagttca agaaaggaaa ggaaagaaat agaacccctt gctaactaca acctagactg    840
agaggtgaag atcgcgggca agacaggtg gtcactgaaa cgtttgcagt tcttttcttc     900
cgaaggctta ggacacaggg taaggaggag ctaaaataaa gccgagtgta cgtttagtct    960
tctctgcacc ccaggcctag tgtctcccca ggcaaggagt cacccccttt gcttctggct   1020
cctaactgaa aaggcaaaa gggagtggag aatgggttaa atcccaggac acaggggaga    1080
```

```
ggcaggggag gagagaagtc ggaggaagat aaaggaaagg acaggaacca agaagcgtgg    1140
gggtagtttg ccgtaatgtg agtgtttctt aattagagag cggctgacaa tagagggct    1200 ggcagaggct cctggccccg gtgcggagcg tctggagcgg agcacgcgct gtcagctggt    1260
gagcgcactc gctttcaggc cgctccccgg ggagctgagc ggccacattt aacaccgtcg    1320
tcaccctccc cggcctcctc aacatcggcc tcctcctcgt agacagcctt gctcggcccc    1380
ccaccggcag agtttacaga agccagagcc tctcgccgtt cccccgcatt cgcccgggtc    1440
tagaatggtg agcaagggcg aggaggataa catggccatc atcaaggagt tcatgcgctt    1500
caaggtgcac atggagggct ccgtgaacgg ccacgagttc gagatcgagg gcagggcga    1560 gggccgcccc tacgagggca cccagaccgc caagctgaag gtgaccaagg gtggcccct    1620 gcccttcgcc tgggacatcc tgtcccctca gttcatgtac ggctccaagg cctacgtgaa    1680
gcaccccgcc gacatccccg actacttgaa gctgtccttc cccgagggct tcaagtggga    1740
gcgcgtgatg aacttcgagg acggcggcgt ggtgaccgtg acccaggact cctccctgca    1800
ggacggcgag ttcatctaca aggtgaagct gcgcggcacc aacttcccct ccgacggccc    1860
cgtaatgcag aagaagacca tgggctggga ggcctcctcc gagcggatgt accccgagga    1920
cggcgccctg aagggcgaga tcaagcagag gctgaagctg aaggacggcg ccactacga    1980 cgctgaggtc aagaccacct acaaggccaa gaagcccgtg cagctgcccg gcgcctacaa    2040
cgtcaacatc aagttggaca tcacctccca caacgaggac tacaccatcg tggaacagta    2100
cgaacgcgcc gagggccgcc actccaccgg cggcatggac gagctgtaca agtaatctag    2160
agtcggggcg gccggccgct tcgagcagac atgataagat acattgatga gtttggacaa    2220
accacaacta gaatgcagtg aaaaaaatgc tttatttgtg aaatttgtga tgctattgct    2280
ttatttgtaa ccattataag ctgcaataaa caagttaaca acaacaattg cattcatttt    2340
atgtttcagg ttcaggggga ggtgtgggag gttttttaaa gcaagtaaaa cctctacaaa    2400
tgtggtaaaa tcgataagga tccgtcgacc gatgcccttg agagccttca acccagtcag    2460
ctccttccgg tgggcgcggg gcatgactat cgtcgccgca cttatgactg tcttctttat    2520
catgcaactc gtaggacagg tgccggcagc gctcttccgc ttcctcgctc actgactcgc    2580
tgcgctcggt cgttcggctg cggcgagcgg tatcagctca ctcaaaggcg gtaatacggt    2640
tatccacaga atcaggggat aacgcaggaa agaacatgtg agcaaaaggc cagcaaaagg    2700
ccaggaaccg taaaaaggcc gcgttgctgg cgttttttcca taggctccgc cccctgacg    2760 agcatcacaa aaatcgacgc tcaagtcaga ggtggcgaaa cccgacagga ctataaagat    2820
accaggcgtt tcccctgga agctccctcg tgcgctctcc tgttccgacc ctgccgctta    2880
ccggatacct gtccgccttt ctcccttcgg aagcgtggc gctttctcat agctcacgct    2940
gtaggtatct cagttcggtg taggtcgttc gctccaagct gggctgtgtg cacgaacccc    3000
ccgttcagcc cgaccgctgc gccttatccg gtaactatcg tcttgagtcc aacccggtaa    3060
gacacgactt atcgccactg gcagcagcca ctggtaacag gattagcaga gcgaggtatg    3120
taggcggtgc tacagagttc ttgaagtggt ggcctaacta cggctacact agaagaacag    3180
tatttggtat ctgcgctctg ctgaagccag ttaccttcgg aaaaagagtt ggtagctctt    3240
gatccggcaa acaaaccacc gctggtagcg gtggtttttt tgtttgcaag cagcagatta    3300
cgcgcagaaa aaaaggatct caagaagatc ctttgatctt ttctacgggg tctgacgctc    3360
agtggaacga aaactcacgt taagggattt tggtcatgag attatcaaaa aggatcttca    3420
cctagatcct tttaaattaa aaatgaagtt ttaaatcaat ctaaagtata tatgagtaaa    3480
```

-continued

```
cttggtctga cagttaccaa tgcttaatca gtgaggcacc tatctcagcg atctgtctat    3540
ttcgttcatc catagttgcc tgactcccg tcgtgtagat aactacgata cgggagggct     3600
taccatctgg ccccagtgct gcaatgatac cgcgagaccc acgctcaccg gctccagatt    3660
tatcagcaat aaaccagcca gccggaaggg ccgagcgcag aagtggtcct gcaactttat    3720
ccgcctccat ccagtctatt aattgttgcc gggaagctag agtaagtagt tcgccagtta    3780
atagtttgcg caacgttgtt gccattgcta caggcatcgt ggtgtcacgc tcgtcgtttg    3840
gtatggcttc attcagctcc ggttcccaac gatcaaggcg agttacatga tcccccatgt    3900
tgtgcaaaaa agcggttagc tccttcggtc ctccgatcgt tgtcagaagt aagttggccg    3960
cagtgttatc actcatggtt atggcagcac tgcataattc tcttactgtc atgccatccg    4020
taagatgctt ttctgtgact ggtgagtact caaccaagtc attctgagaa tagtgtatgc    4080
ggcgaccgag ttgctcttgc ccggcgtcaa tacgggataa taccgcgcca catagcagaa    4140
ctttaaaagt gctcatcatt ggaaaacgtt cttcggggcg aaaactctca aggatcttac    4200
cgctgttgag atccagttcg atgtaaccca ctcgtgcacc caactgatct tcagcatctt    4260
ttactttcac cagcgtttct gggtgagcaa aaacaggaag gcaaaatgcc gcaaaaaagg    4320
gaataagggc gacacggaaa tgttgaatac tcatactctt ccttttcaa tattattgaa     4380
gcatttatca gggttattgt ctcatgagcg gatacatatt tgaatgtatt tagaaaaata    4440
aacaaatagg ggttccgcgc acatttcccc gaaaagtgcc acctgacgcg ccctgtagcg    4500
gcgcattaag cgcggcgggt gtggtggtta cgcgcagcgt gaccgctaca cttgccagcg    4560
ccctagcgcc cgctcctttc gctttcttcc cttcctttct cgccacgttc gccggctttc    4620
cccgtcaagc tctaaatcgg gggctccctt tagggttccg atttagtgct ttacggcacc    4680
tcgaccccaa aaaacttgat tagggtgatg gttcacgtag tgggccatcg ccctgataga    4740
cggttttttcg cccctttgacg ttggagtcca cgttctttaa tagtggactc ttgttccaaa   4800
ctggaacaac actcaaccct atctcggtct attctttga tttataaggg attttgccga     4860
tttcggccta ttggttaaaa aatgagctga tttaacaaaa atttaacgcg aattttaaca    4920
aaatattaac gcttacaatt tgccattcgc cattcaggct gcgcaactgt tgggaagggc    4980
gatcggtgcg ggcctcttcg ctattacgcc agcccaagct accatgataa gtaagtaata    5040
ttaaggtacg ggaggtactt ggagcggccg caataaaata tctttatttt cattacatct    5100
gtgtgttggt tttttgtgtg aatcgatagt actaacatac gctctccatc aaaacaaaac    5160
gaaacaaaac aaactagcaa aataggctgt ccccagtgca agtgcaggtg ccagaacatt    5220
tctctatcga tacata                                                     5236
```

EXPANSION AND DIFFERENTIATION OF INNER EAR SUPPORTING CELLS AND METHODS OF USE THEREOF

CLAIM OF PRIORITY

This application is a § 371 U.S. National Phase Application of PCT/US2017/015379, filed on Jan. 27, 2017, which claims the benefit of U.S. Provisional Application Ser. No. 62/288,958, filed on Jan. 29, 2016. The entire contents of the foregoing are incorporated herein by reference.

STATEMENT OF FEDERALLY SPONSORED RESEARCH

This invention was made with government support under Grant Number DC015824, DC000038, W81XWH-15-1-0472, awarded by the National Institutes of Health. The government has certain rights in the invention.

TECHNICAL FIELD

Described herein are methods for expanding and differentiating inner ear supporting cells (e.g., Lgr5+ inner ear supporting cells) from the sensory epithelium of the inner ear of a mammal, and the use of the expanded cells, e.g., for identifying candidate therapeutic compounds for the treatment of hearing loss or balance loss. Additionally, the methods described herein can be used in the treatment of hearing loss or balance loss that would benefit from increased proliferation of inner ear supporting cells (e.g., Lgr5+ inner ear supporting cells), and differentiation thereof into inner ear hair cells (e.g., atonal homolog 1 (Atoh1)+ inner ear hair cells).

BACKGROUND

Hearing impairment is a major health challenge estimated by the WHO to affect over 5% of the world's population (360 million people, including 32 million children). The sensory hair cells that detect sound and transmit their signal to the brain via the auditory nerve are susceptible to damage. After loss, the hair cells are never replaced[1,2], and thus the number of cells, which is low (15,000 per ear) at the start of postnatal life, only decreases with age, and the absence of cell replacement leads to a high prevalence of acquired forms of deafness. Indeed, hair cell and auditory nerve damage, typically caused by noise exposure, ototoxic drugs, viral/bacterial infections, and aging accounts for more than 80% of all cases of hearing loss[3]. In addition to hearing impairment, damage or loss of sensory hair cells can cause balance impairment and diseases related to balance impairment, e.g., benign paroxysmal positional vertigo (BPPV).

SUMMARY

The present disclosure is based, at least in part, on the discovery of methods for expanding inner ear supporting cells (e.g., Lgr5+ inner ear supporting cells, e.g., Lgr5+ cochlear or vestibular supporting cells) from the sensory epithelium of the inner ear of a mammal, and the use of the expanded cells, e.g., for identifying candidate therapeutic compounds for the treatment of hearing loss or balance loss. Additionally, described herein are methods for using screened compounds in the treatment of hearing loss or balance loss that would benefit from increased proliferation of inner ear supporting cells (e.g., Lgr5+ inner ear supporting cells) and/or increased numbers of inner ear hair cells (e.g., atonal homolog 1 (Atoh1)+ inner ear hair cells).

In a first aspect, the invention features a method of producing an expanded population of inner ear supporting cells. The method includes contacting a population of inner ear supporting cells with one or more agents selected from the group consisting of: (a) a retinoid receptor signaling activator; (b) a Wnt signaling activator set forth in Table A; (c) a bone morphogenetic protein (BMP) signaling inhibitor set forth in Table B; (d) a cyclin-dependent kinase (CDK) activator set forth in Table C; (e) an E box-dependent transcriptional activator set forth in Table D; (f) a Notch signaling activator set forth in Table E; (g) a histone deacetylase (HDAC) inhibitor set forth in Table F; (h) a protein degradation inhibitor set forth in Table G; (i) a PI3K-Akt signaling inhibitor set forth in Table H; and (j) a cAMP response element binding protein (CREB) activator set forth in Table I, in which the one or more agents are present in amounts sufficient to produce an expanded population of inner ear supporting cells.

In some embodiments of the first aspect of the invention, the Notch signaling activator is a Delta-like protein activator, a Jagged protein activator, a Notch activator, and/or a γ-secretase activator.

In some embodiments of the first aspect of the invention, the one or more agents are selected from the group consisting of: (a) a retinoid receptor signaling activator; (b) a Wnt signaling activator set forth in Table A; (c) a BMP signaling inhibitor set forth in Table B; (d) a CDK activator set forth in Table C; and (e) an E box-dependent transcriptional activator set forth in Table D.

In some embodiments of the first aspect of the invention, the expanded population of inner ear supporting cells is an expanded population of Lgr5+ inner ear supporting cells. In some embodiments, the expanded population of Lgr5+ inner ear supporting cells is an expanded population of Lgr5+ cochlear supporting cells. In some embodiments, the expanded population of Lgr5+ inner ear supporting cells is an expanded population of Lgr5+ vestibular supporting cells.

In a second aspect, the invention features a method of promoting differentiation of a population of inner ear supporting cells into a population of inner ear hair cells. The method includes contacting a population of inner ear supporting cells with one or more agents selected from the group consisting of: (a) a retinoid receptor signaling activator; (b) a Wnt signaling activator set forth in Table A; (c) a BMP signaling inhibitor set forth in Table B; (d) a CDK activator set forth in Table C; (e) an E box-dependent transcriptional activator set forth in Table D; (0 an HDAC inhibitor set forth in Table F; (g) a protein degradation inhibitor set forth in Table G; (h) a PI3K-Akt signaling inhibitor set forth in Table H; (i) a CREB activator set forth in Table I; and (j) a Notch signaling inhibitor set forth in Table J, in which the one or more agents are present in amounts sufficient to promote differentiation into a population of inner ear hair cells.

In some embodiments of the second aspect of the invention, the one or more agents is selected from the group consisting of: (a) a Wnt signaling activator set forth in Table A; (b) an E box-dependent transcriptional activator set forth in Table D; (c) an HDAC inhibitor set forth in Table F; (d) a protein degradation inhibitor set forth in Table G; and (e) a Notch signaling inhibitor set forth in Table J.

In some embodiments of the second aspect of the invention, the Notch signaling inhibitor is a Delta-like protein inhibitor, a Jagged protein inhibitor, a Notch inhibitor, and/or a γ-secretase inhibitor.

In some embodiments of the second aspect of the invention, the population of inner ear hair cells is a population of Atoh1+ inner ear hair cells. In some embodiments, the population of Atoh1+ inner ear hair cells is a population of Atoh1+ cochlear hair cells. In some embodiments, the population of Atoh1+ inner ear hair cells is a population of Atoh1+ vestibular hair cells.

In some embodiments of the first and second aspects of the invention, the retinoid receptor signaling activator is a retinoic acid receptor (RAR) agonist set forth in Table K and/or a retinoic X receptor (RXR) agonist set forth in Table K. In some embodiments, the RAR agonist is an RARα agonist, an RARβ agonist, and/or an RARγ agonist. In some embodiments, the RXR agonist is an RXRα agonist, an RXRβ agonist, and/or an RXRγ agonist.

In some embodiments of the first and second aspects of the invention, the Wnt signaling activator is a glycogen synthase kinase-3β (GSK-3β) inhibitor, a Wnt activator, a Frizzled receptor activator, a lipoprotein receptor-related protein 5/6 (LRP5/6) activator, a Disheveled (Dvl) activator, an Axin inhibitor, a Dickkopf (Dkk) inhibitor, a secreted Frizzled-related protein (sFRP) inhibitor, a Groucho inhibitor, and/or a Wnt inhibitory protein (WIF) inhibitor.

In some embodiments of the first and second aspects of the invention, the BMP signaling inhibitor is a Noggin activator, a Chordin activator, a BMP receptor inhibitor, a SMAD1/5/8 inhibitor, a SMAD2/3 inhibitor, and/or a SMAD4 inhibitor.

In some embodiments of the first and second aspects of the invention, the CDK activator is a p27Kip1 inhibitor and/or a retinoblastoma protein (Rb) inhibitor.

In some embodiments of the first and second aspects of the invention, the E box-dependent transcriptional activator is an Atoh1 activator.

In some embodiments of the first and second aspects of the invention, the HDAC inhibitor is an HDAC class I inhibitor, an HDAC class II inhibitor, an HDAC class III inhibitor, and/or a pan-HDAC inhibitor. In some embodiments, the HDAC class III inhibitor is a SIRT1 inhibitor and/or a SIRT2 inhibitor.

In some embodiments of the first and second aspects of the invention, the protein degradation inhibitor is a proteasome inhibitor or a ubiquitin ligase inhibitor.

In some embodiments of the first and second aspects of the invention, the PI3K-Akt signaling inhibitor is an Akt inhibitor, a PI3K inhibitor, a PKC inhibitor, and/or a PDK1 inhibitor.

In some embodiments of the first and second aspects of the invention, the population of inner ear supporting cells is a population of Lgr5+ inner ear supporting cells. In some embodiments, the population of Lgr5+ inner ear supporting cells is a population of Lgr5+ cochlear supporting cells. In some embodiments, the population of Lgr5+ inner ear supporting cells is a population of Lgr5+ vestibular supporting cells.

In a third aspect, the invention features a transgenic mouse having two or more recombinant nucleic acid molecules stably integrated into the genome of the mouse. The two or more recombinant nucleic acid molecules include at least a first recombinant nucleic acid molecule that includes a first reporter gene under the control of a regulatory element of an inner ear supporting cell marker selected from the group consisting of Lgr5, Sox2, p27, Prox1, FGFR3, Glast, and Lfng, and a second recombinant nucleic acid molecule that includes a second reporter gene under the control of a regulatory element of an inner ear hair cell marker selected from the group consisting of Atoh1, Myo7a, Cdh23, Pcdh15, Myo6, Myo1c, Tmc1, and Cav1.3, in which the first reporter gene is different from the second reporter gene.

In some embodiments of the third aspect of the invention, the inner ear supporting cell marker is Lgr5.

In some embodiments of the third aspect of the invention, the inner ear hair cell marker is Atoh1.

In some embodiments of the third aspect of the invention, the inner ear supporting cell marker is Lgr5 and the inner ear hair cell marker is Atoh1.

In some embodiments of the third aspect of the invention, the regulatory element of an inner ear supporting cell marker is an Lgr5 promoter.

In some embodiments of the third aspect of the invention, the regulatory element of an inner ear hair cell marker is an Atoh1 enhancer. In some embodiments, the Atoh1 enhancer is operably linked to a promoter element, e.g., an SV40 promoter or a globin promoter.

In some embodiments of the third aspect of the invention, the first reporter gene encodes a first fluorescent protein and the second reporter gene encodes a second fluorescent protein, wherein the first fluorescent protein is different from the second fluorescent protein.

In a fourth aspect, the invention features a cell isolated from the transgenic mouse of the third aspect of the invention. The cell includes the first recombinant nucleic acid molecule and the second recombinant nucleic acid molecule.

In some embodiments of the fourth aspect of the invention, the cell is isolated from the inner ear of the transgenic mouse.

In a fifth aspect of the invention, the invention features a method for identifying a candidate agent for the treatment of hearing loss or balance loss associated with a loss of cochlear or vestibular hair cells, in which the method includes: (a) isolating a population of inner ear supporting cells from the mouse of any one of claims 29-36; (b) maintaining the population of inner ear supporting cells under conditions sufficient to produce an expanded population of inner ear supporting cells; (c) administering a test compound to the expanded population of inner ear supporting cells; (d) detecting the expression levels of the first reporter gene and the second reporter gene in the expanded population of inner ear supporting cells in the presence of the test compound; and (e) selecting as a candidate agent for the treatment of hearing loss or balance loss a test compound that increases the expression level of the first reporter gene compared to the expression level of the first reporter gene in the absence of the test compound, and/or increases the expression level of the second reporter gene compared to the expression level of the second reporter gene in the absence of the test compound.

In some embodiments of the fifth aspect of the invention, the conditions sufficient to produce an expanded population of inner ear supporting cells include media, e.g., a mixture of DMEM and F12 media, e.g., a 1:1 mixture, in the presence of one or more growth factors, e.g., epidermal growth factor (EGF), basic fibroblast growth factor (bFGF), and/or insulin-like growth factor (IGF1). In some embodiments, the population of inner ear supporting cells is cultured for two or more days, e.g., between two days and ten days, e.g., between two days and five days.

In some embodiments of the fifth aspect of the invention, the conditions sufficient to produce an expanded population of inner ear supporting cells further include one or more agents selected from the group consisting of: (a) a retinoid receptor signaling activator; (b) a Wnt signaling activator set forth in Table A; (c) a BMP signaling inhibitor set forth in Table B; (d) a CDK activator set forth in Table C; (e) an E box-dependent transcriptional activator set forth in Table D; (f) a Notch signaling activator set forth in Table E or a Notch signaling inhibitor set forth in Table J; (g) an HDAC inhibitor set forth in Table F; (h) a protein degradation inhibitor set forth in Table G; (i) a PI3K-Akt signaling inhibitor set forth in Table H; and (j) a CREB activator set forth in Table I.

In some embodiments of the fifth aspect of the invention, the retinoid receptor signaling activator is an RAR agonist set forth in Table K or an RXR agonist set forth in Table K.

In some embodiments of the fifth aspect of the invention, the conditions sufficient to produce an expanded population of inner ear supporting cells include one or more agents set forth in Table 1.

In some embodiments of the fifth aspect of the invention, the conditions sufficient to produce an expanded population of inner ear supporting cells include media, e.g., a 1:1 mixture of DMEM and F12, supplemented with N2, B27, EGF, bFGF, IGF1, CHIR99021, and VPA.

In some embodiments of the fifth aspect of the invention, the candidate agent is selected from a group consisting of a small molecule, a compound, a nucleic acid, a peptide, a polypeptide, a growth factor, and an epigenetic modifier.

In some embodiments of the fifth aspect of the invention, the population of inner ear supporting cells is isolated from the cochlea of the mouse by a method including first dissecting the organ of Corti, isolating sensory epithelium, and creating a single cell suspension. In some embodiments of the fifth aspect of the invention, the population of inner ear supporting cells is isolated from the vestibule of the inner ear of the mouse.

In some embodiments of the fifth aspect of the invention, the population of inner ear supporting cells is a population of Lgr5+ inner ear supporting cells.

In some embodiments of the fifth aspect of the invention, the first reporter gene is encodes a first fluorescent protein and the second reporter gene encodes a second fluorescent protein, wherein the first fluorescent protein is different from the second fluorescent protein.

In some embodiments of the fifth aspect of the invention, the expression levels of the first reporter gene and the second reporter gene are protein expression levels.

In a sixth aspect, the invention features a method for identifying a candidate agent for the treatment of hearing loss or balance loss associated with a loss of cochlear or vestibular hair cells, in which the method includes: (a) providing a population of inner ear supporting cells having a stably integrated recombinant nucleic acid molecule that includes a reporter gene under the control of a regulatory element of an inner ear supporting cell marker selected from the group consisting of Lgr5, Sox2, p27, Prox1, FGFR3, Glast, and Lfng; (b) maintaining the population of inner ear supporting cells under conditions sufficient to produce an expanded population of inner ear supporting cells, wherein the conditions include one or more agents selected from the group consisting of: (i) a retinoid receptor signaling activator, (ii) a Wnt signaling activator set forth in Table A, (iii) a BMP signaling inhibitor set forth in Table B, (iv) a CDK activator set forth in Table C, (v) an E box-dependent transcriptional activator set forth in Table D, (vi) a Notch signaling activator set forth in Table E, (vii) an HDAC inhibitor set forth in Table F, (viii) a protein degradation inhibitor set forth in Table G, (ix) a PI3K-Akt signaling inhibitor set forth in Table H, and (x) a CREB activator set forth in Table I; (c) administering a test compound to the expanded population of inner ear supporting cells; (d) detecting the expression level of the reporter gene in the expanded population of inner ear supporting cells in the presence of the test compound; and (e) selecting as a candidate agent for the treatment of hearing loss or balance loss a test compound that increases the expression level of the reporter gene compared to the expression level of the reporter gene in the absence of the test compound.

In a seventh aspect, the invention features a method for identifying a candidate agent for the treatment of hearing loss or balance loss associated with a loss of cochlear or vestibular hair cells, in which the method includes: (a) providing a population of inner ear supporting cells having a stably integrated recombinant nucleic acid molecule that includes a reporter gene under the control of a regulatory element of an inner ear hair cell marker selected from the group consisting of Atoh1, Myo7a, Cdh23, Pcdh15, Myo6, Myo1c, Tmc1, and Cav1.3; (b) maintaining the population of inner ear supporting cells under conditions sufficient to produce an expanded population of inner ear supporting cells, wherein the conditions include one or more agents selected from the group consisting of: (i) a retinoid receptor signaling activator, (ii) a Wnt signaling activator set forth in Table A, (iii) a BMP signaling inhibitor set forth in Table B, (iv) a CDK activator set forth in Table C, (v) an E box-dependent transcriptional activator set forth in Table D, (vi) a Notch signaling activator set forth in Table E, (vii) an HDAC inhibitor set forth in Table F, (viii) a protein degradation inhibitor set forth in Table G, (ix) a PI3K-Akt signaling inhibitor set forth in Table H, and (x) a CREB activator set forth in Table I; (c) administering a test compound to the expanded population of inner ear supporting cells; (d) detecting the expression level of the reporter gene in the expanded population of inner ear cells in the presence of the test compound; and (e) selecting as a candidate agent for the treatment of hearing loss or balance loss a test compound that increases the expression level of the reporter gene compared to the expression level of the reporter gene in the absence of the test compound.

In some embodiments of the sixth and seventh aspects of the invention, the retinoid receptor signaling activator is an RAR agonist set forth in Table K or an RXR agonist set forth in Table K.

In some embodiments of the sixth and seventh aspects of the invention, the conditions sufficient to produce an expanded population of inner ear supporting cells include one or more agents selected from the group consisting of: (a) a retinoid receptor signaling activator; (b) a Wnt signaling activator set forth in Table A; (c) a BMP signaling inhibitor set forth in Table B; (d) a CDK activator set forth in Table C; and (e) an E box-dependent transcriptional activator set forth in Table D.

In some embodiments of the sixth and seventh aspects of the invention, the expanded population of inner ear supporting cells is an expanded population of Lgr5+ inner ear supporting cells. In some embodiments, the expanded population of Lgr5+ inner ear supporting cells is an expanded population of Lgr5+ cochlear supporting cells. In some embodiments, the expanded population of Lgr5+ inner ear supporting cells is an expanded population of Lgr5+ vestibular supporting cells.

In some embodiments of the sixth and seventh aspects of the invention, the population of inner ear supporting cells is isolated from a human. In some embodiments, the population of inner ear supporting cells is isolated from a mouse.

In some embodiments of the sixth and seventh aspects of the invention, the reporter gene encodes a fluorescent protein.

In an eighth aspect, the invention features a method of treating a subject having hearing loss or balance loss, in which the method includes administering to the subject in need thereof one or both of: (a) a therapeutically effective amount of one or more agents that promote proliferation of inner ear supporting cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; (v) an E box-dependent transcriptional activator set forth in Table D; (vi) a Notch signaling activator set forth in Table E; (vii) an HDAC inhibitor set forth in Table F; (viii) a protein degradation inhibitor set forth in Table G; and (ix) a PI3K-Akt signaling inhibitor set forth in Table H; and/or (b) a therapeutically effective amount of one or more agents that promote differentiation of inner ear supporting cells into inner ear hair cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; (v) an E box-dependent transcriptional activator set forth in Table D; (vi) an HDAC inhibitor set forth in Table F; (vii) a protein degradation inhibitor set forth in Table G; (viii) a PI3K-Akt signaling inhibitor set forth in Table H; (ix) a CREB activator set forth in Table I; and (x) a Notch signaling inhibitor set forth in Table J.

In some embodiments of the eighth aspect of the invention, the method includes administering to the subject in need thereof one or both of: (a) a therapeutically effective amount of one or more agents that promote proliferation of inner ear supporting cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; and (v) an E box-dependent transcriptional activator set forth in Table D; and/or (b) a therapeutically effective amount of one or more agents that promote differentiation of inner ear supporting cells into inner ear hair cells selected from the group consisting of: (i) a Wnt signaling activator set forth in Table A; (ii) an E box-dependent transcriptional activator set forth in Table D; (iii) an HDAC inhibitor set forth in Table F; (iv) a protein degradation inhibitor set forth in Table G; and (v) a Notch signaling inhibitor set forth in Table J.

In some embodiments of the eighth aspect of the invention, the one or more agents are administered systemically. In some embodiments of the eighth aspect of the invention, the one or more agents are administered locally, e.g., to the ear of the subject, e.g., transtympanically to the middle ear of the subject.

In some embodiments of the eighth aspect of the invention, the one or more agents that promote proliferation of inner ear supporting cells are administered prior to the one or more agents that promote differentiation of inner ear supporting cells into inner ear hair cells.

In a ninth aspect, the invention features a method of treating a subject having hearing loss or balance loss, in which the method includes: (a) contacting one or more inner ear supporting cells, e.g., in vitro, with one or more agents that promote proliferation of inner ear supporting cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; (v) an E box-dependent transcriptional activator set forth in Table D; (vi) a Notch signaling activator set forth in Table E; (vii) an HDAC inhibitor set forth in Table F; (viii) a protein degradation inhibitor set forth in Table G; (ix) a PI3K-Akt signaling inhibitor set forth in Table H; and (x) a CREB activator set forth in Table I; (b) optionally contacting the expanded population of inner ear supporting cells with one or more agents that promote differentiation of inner ear supporting cells into inner ear hair cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; (v) an E box-dependent transcriptional activator set forth in Table D; (vi) an HDAC inhibitor set forth in Table F; (vii) a protein degradation inhibitor set forth in Table G; (viii) a PI3K-Akt signaling inhibitor set forth in Table H; (ix) a CREB activator set forth in Table I; and (x) a Notch signaling inhibitor set forth in Table J; and (c) administering the inner ear hair cells to the ear (e.g., the inner ear) of the subject.

In a tenth aspect, the invention features a method of treating a subject having hearing loss or balance loss, in which the method includes: (a) contacting one or more inner ear supporting cells, e.g., in vitro, with one or more agents that promote proliferation of inner ear supporting cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; (v) an E box-dependent transcriptional activator set forth in Table D; (vi) a Notch signaling activator set forth in Table E; (vii) an HDAC inhibitor set forth in Table F; (viii) a protein degradation inhibitor set forth in Table G; (ix) a PI3K-Akt signaling inhibitor set forth in Table H; and (x) a CREB activator set forth in Table I; and (b) administering the expanded population of inner ear supporting cells to the ear (e.g., the inner ear) of the subject in combination with, e.g., concurrently with or prior to administration of, one or more agents that promote differentiation of inner ear supporting cells into inner ear hair cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; (v) an E box-dependent transcriptional activator set forth in Table D; (vi) an HDAC inhibitor set forth in Table F; (vii) a protein degradation inhibitor set forth in Table G; (viii) a PI3K-Akt signaling inhibitor set forth in Table H; (ix) a CREB activator set forth in Table I; and (x) a Notch signaling inhibitor set forth in Table J.

In some embodiments of the eighth, ninth, and tenth aspects of the invention, (a) the one or more agents that promote proliferation of inner ear supporting cells is selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; and (v) an E box-dependent transcriptional activator set forth in Table D; and (b) the one or more agents that promote differentiation of inner ear supporting cells into inner ear hair cells is selected from the group consisting of: (i) a Wnt signaling activator set forth in Table A; (ii) an E box-dependent transcriptional activator set forth in Table D; (iii) an HDAC inhibitor set forth in Table F; (iv) a protein degradation inhibitor set forth in Table G; and (v) a Notch signaling inhibitor set forth in Table J.

In some embodiments of the eighth, ninth, and tenth aspects of the invention, the retinoid receptor signaling activator is an RAR agonist set forth in Table K or an RXR agonist set forth in Table K.

In some embodiments of the eighth, ninth, and tenth aspects of the invention, the inner ear supporting cells are Lgr5+ inner ear supporting cells.

In some embodiments of the eighth, ninth, and tenth aspects of the invention, the inner ear hair cells are Atoh1+ inner ear hair cells.

In some embodiments of the eighth, ninth, and tenth aspects of the invention, the subject has balance loss. In some embodiments of the eighth, ninth, and tenth aspects of the invention, the subject has hearing loss (e.g., sensorineural hearing loss). In some embodiments, the hearing loss is the result of a genetic or congenital defect, trauma (e.g., physical trauma or noise-related insult trauma), aging, or chemical-induced ototoxicity. In some embodiments, the hearing loss is the result of an infection (e.g., a viral or a bacterial infection).

In some embodiments of the eighth, ninth, and tenth aspects of the invention, the subject is a human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

Definitions

As used herein, the term "expanded population" of inner ear supporting cells refers to a population of cells including at least one more inner ear supporting cells, such that the quantity of inner ear supporting cells in the population is greater (e.g., at least 10% greater, at least 20% greater, at least 30% greater) than the number of inner ear supporting cells prior to administration of one or more agents as described herein (e.g., one or more agents that exhibit one or more activities, such as activation of retinoid receptor signaling, activation of Wnt signaling, inhibition of bone morphogenetic protein (BMP) signaling, activation of a cyclin-dependent kinase (CDK), activation of E box-dependent transcription, activation Notch signaling, inhibition of a histone deacetylase (HDAC), inhibition of protein degradation, inhibition of PI3K-Akt signaling, and activation of cAMP response element binding protein (CREB).

As used herein, the term "inner ear supporting cells" refers to non-sensory cells that reside between hair cells (e.g., cochlear supporting cells and vestibular supporting cells) and serve a diverse set of functions, such as maintaining an environment in the epithelium that enables hair cells to function and supporting the structural integrity of the sensory organs during sound stimulation and head movements.

As used herein, the term "inner ear hair cells" refers to sensory cells that reside within the organ of Corti in the cochlea or the vestibule of the osseous labyrinth of the inner ear. The inner ear hair cells are responsible for transmitting sounds waves as electrical signals to the brain. Damage to cochlear inner ear hair cells can result in decreased hearing sensitivity or hearing loss. Damage to vestibular inner ear hair cells can result in balance impairment or balance loss.

As used herein, a "retinoid receptor signaling activator" refers to a compound that binds and activates one or more retinoid receptors (e.g., RARα, RARβ, RARγ, RXRα, RXRβ, and RXRγ), thereby affecting the transcriptional activity of a target gene to which the activated retinoid receptor binds. A retinoid receptor signaling activator may be a pan-retinoid receptor activator or exhibit selectivity towards one or more retinoid receptors. Examples of activators of retinoid receptor signaling include, but are not limited to, compounds listed in Table K.

As used herein, a "Wnt signaling activator" refers to an agonist of the canonical Wnt signaling pathway. Agonists of this pathway further include Wnt proteins or other compounds that bind directly to the Frizzled and lipoprotein receptor-related protein 5/6 (LRP5/6) co-receptor proteins (e.g., a Frizzled receptor activator, a LRP5/6 activator), in manner that promotes an increase in the concentration of β-catenin in the nucleus of a mammalian cell. Alternatively, a β-catenin/Wnt pathway agonist may function by inhibiting one or more secreted Frizzled-related proteins (sFRPs) (e.g., an sFRP inhibitor) or Wnt inhibitory protein (WIF) (e.g., a WIF inhibitor), which bind and sequester Wnt proteins from interacting with the endogenous Wnt co-receptors. Examples of Wnt signaling activators also include, but are not limited to, a glycogen synthase kinase-3β (GSK-3β) inhibitor, a Wnt activator, a Disheveled (Dvl) activator, an Axin inhibitor, a Dickkopf (Dkk) inhibitor, and a Groucho inhibitor. GSK-3β is a kinase that forms a complex with Axin, APC (Adenomatous polyposis coli), and β-catenin to prepare β-catenin for downstream degradation by the proteasome. Disheveled (Dvl) is an intracellular protein that relays signals from activated Notch receptors to downstream effectors. Disheveled (Dvl) is recruited by the receptor Frizzled and prevents the constitutive descruction of β-catenin. Dickkopf (Dkk) is a secreted protein that acts to isolate the LRP5/6 co-receptor proteins, thus inhibiting Wnt signaling. Groucho is a protein that forms a complex with TLE in the nucleus to repress gene expression. Once β-catenin enters the nucleus, it disrupts the Groucho/TLE complex to activate gene expression. A Wnt activator refers to a small molecule compound that activates Wnt signaling.

Exemplary methods that can be used to determine the activity of a β-catenin/Wnt pathway agonist include, without limitation, monitoring the expression of a reporter gene under the control of a TCF/LEF family transcription factor, as well as TOPFlash luciferase reporter assays, as described in US 2014/0044763. Examples of activators of Wnt signaling include, but are not limited to, compounds listed in Table A.

As used herein, a "bone morphogenic protein (BMP) signaling inhibitor" refers to an antagonist of the BMP signaling pathway. BMP is a member of the TGFβ superfamily of ligands, and modulators of BMP signaling can be used in conjunction with the methods of the invention, e.g., to expand inner ear supporting cells or to differentiate inner ear supporting cells to inner ear hair cells. Inhibitors of the BMP signaling pathway include any proteins or small molecule compounds that inhibit a protein involved in the BMP signaling pathway. Examples of BMP signaling inhibitors include, but are not limited to, a Noggin activator, a Chordin activator, a BMP receptor inhibitor, a SMAD1/5/8 inhibitor, a SMAD2/3 inhibitor, and a SMAD4 inhibitor. Noggin and Chordin are antagonists that inhibit the binding of BMP to BMP receptors. BMP receptors transduce signals from BMPs. Activated BMP receptors recruit and phosphorylate transcription factors SMAD1/5/8. Phosphorylated SMAD1/5/8 interacts with SMAD4 to form a complex, which goes into the nucleus to regulate gene expression. BMP receptors transduce signals from activin or activin-like ligands. Activated BMP receptors recruit and phosphorylate transcription factors SMAD2/3. Phosphorylated SMAD2/3 interacts with SMAD4 to form a complex, which goes into the nucleus to regulate gene expression. Examples of BMP signaling inhibitors include, but are not limited to, compounds listed in Table B.

As used herein, a "cyclin-dependent kinase (CDK) activator" refers to an agonist of CDK. CDKs are a family of serome/threonine kinases involved regulating cell cycle. A CDK binds a regulatory protein cyclin to form the activated kinase. A CDK activator may be a protein or a small molecule compound that interacts with CDK to increase its activity, or a protein or a small molecule compound that interacts with a protein that interacts with CDK to indirectly increase CDK activity. A CDK activator may be an inhibitor of a CDK inhibitor (e.g., a p27Kip1 inhibitor) or a retinoblastoma protein (Rb) inhibitor. The protein p27Kip1 is a cell-cycle regulatory protein that interacts with cyclin-CDK2 complex and cyclin-CDK4 complex and inhibits cell cycle progression at G1. An Rb is a tumor suppressor protein that also inhibits cell cycle progression at G1.

As used herein, an "E box-dependent transcriptional activator" refers to a protein (e.g., a transcription factor) compound that binds to E box to activate the expression of the gene downstream of the E box. An E box refers to an enhancer box, which is a DNA response element that acts as a protein-binding site to regulate gene expression. Transcription factors bind to an E box to initiate gene transcription. An example of an E box-dependent transcriptional activator is an Atoh1 activator, which up-regulates the expression of Atoh1. Atoh1 is a basic helix-loop-helix (bHLH) transcription factor involved in regulating neurosensory development in the ear.

As used herein, a "Notch signaling activator" refers to a protein or a small molecule compound that promotes the activation of Notch pathway function. The term "Notch pathway function" as used herein refers to a function mediated by the Notch signal transduction pathway including, but not limited to, nuclear translocation of the intracellular domain of Notch, nuclear translocation of RBP-Jκ or its *Drosophila* homolog Suppressor of Hairless; activation of bHLH genes of the Enhancer of Split complex, e.g., Mastermind; activation of the HES-1 gene or the KBF2 (also referred to as CBF1) gene; inhibition of *Drosophila* neuroblast segregation; and binding of Notch to a Delta protein, a Jagged/Serrate protein, Fringe, Deltex or RBP-Jκ/Suppressor of Hairless, or homologs or analogs thereof. The Notch signal transduction cascade and the phenotypes effected by Notch signaling are described, e.g., in Kopan et al., Cell 137:216-233 (2009) and Jarriault, et al., Mol. Cell. Biol. 18:7423-7431 (1998), the disclosures of each of which are incorporated herein by reference.

Examples of Notch agonists are described, e.g., in US 2014/0369973 and in U.S. Pat. No. 7,399,633, the disclosures of each of which are incorporated herein by reference. Exemplary Notch agonists include, without limitation, Notch proteins, as well as analogs, derivatives, and fragments thereof, other proteins that propagate the Notch signaling pathway, as well as analogs, derivatives, and fragments thereof; activating antibodies that stimulate Notch receptor activity and antigen-binding fragments thereof that retain agonistic activity; nucleic acids encoding proteins that potentiate Notch signaling; as well as proteins, derivatives, and analogs thereof which bind to or otherwise interact with Notch proteins or other proteins in the Notch pathway such that Notch pathway activity is promoted. Such agonists include, but are not limited to, Notch proteins and derivatives thereof containing the Notch intracellular domain, Notch nucleic acids encoding the foregoing, and proteins contacting the Notch-interacting domain of Notch ligands (e.g., the extracellular domain of Delta or Serrate).

Other Notch agonists include, but are not limited to, a Delta-like protein activator, a Jagged protein activator, a Notch activator, and a γ-secretase activator. Delta-like protein and Jagged protein are transmembrane proteins that interact with Notch receptors on adjacent cells to activate Notch signaling. Gamma-secretase is an enzyme that cleaves the part of the Notch receptor on the inside the inner leaflet of the cell membrane of the Notch receptor-expression cell. The cleavage by γ-secretase releases the intracellular domain of the Notch receptor, which then moves to the nucleus to regulate gene expression. A Notch activator refers to a small molecule compound that activates Notch signaling. Other Notch agonists include, but are not limited to, RBPJκ/Suppressor of Hairless or Deltex. Fringe can additionally be used to enhance Notch activity, for example in conjunction with Delta protein. These proteins, fragments, and derivatives thereof can be recombinantly expressed and isolated or can be chemically.

As used herein, a "Notch signaling inhibitor" refers to a protein or a small molecule compound that inhibits Notch pathway function. The term "Notch pathway function" is described above. In some embodiments, a Notch signaling inhibitor may inhibit the activity of one or more proteins involved in the activation of Notch signaling. In some embodiments, a Notch signaling inhibitor may activate the activity of one or more proteins involved in the inhibition of Notch signaling. Notch signaling inhibitors include, but are not limited to, a Delta-like protein inhibitor, a Jagged protein inhibitor, a Notch inhibitor, and/or a γ-secretase inhibitor. Examples of Notch signaling inhibitors include, but are not limited to, compounds listed in Table J.

As used herein, a "histone deacetylase (HDAC) inhibitor" refers a compound that binds and inhibits one or more HDACs, thereby affecting the enzyme activity of the HDAC. An HDAC refers to any one of a family of enzymes that catalyze the removal of acetyl groups from the ε-amino groups of lysine residues at the N-terminus of a histone. Unless otherwise indicated by context, the term "histone" is meant to refer to any histone protein, including HI, H2A, H2B, H3, H4, and H5, from any species. Human HDAC proteins are separated into four classes: class I includes HDAC1, HDAC2, HDAC3, and HDAC8; class II includes HDAC4, HDAC5, HDAC7, and HDAC9; class III includes SIRT1, SIRT2, SIRT3, SIRT4, SIRT5, SIRT6, and SIRT7; and class IV includes HDAC11. An HDAC inhibitor may be a pan-HDAC inhibitor or exhibit selectivity towards one or more HDACs. Examples of HDAC inhibitors include, but are not limited to, compounds listed in Table F.

As used herein, a "protein degradation inhibitor" refers to a compound that inhibits a protein degradation pathway, e.g., an ubiquitin-proteasome degradation pathway. A protein degradation inhibitor may inhibit the activity of one or more of the proteins involved in a protein degradation pathway, e.g., an ubiquitin-proteasome degradation pathway. For example, a protein degradation inhibitor may be a small molecule compound that inhibits the proteasome (e.g., a proteasome inhibitor), i.e., inhibits the 19S or 20S of the proteasome, or a small molecule compound that inhibits ubiquitin activating enzyme (E1), ubiquitin conjugating enzyme (E2), and/or ubiquitin ligase (E3) (e.g., an ubiquitin ligase inhibitor). In the ubiquitin-proteasome degradation pathway, proteins are marked for degradation by the proteasome by being linked to the co-factor ubiquitin. E1 first forms a thio-ester bond with ubiquitin. This reaction allows subsequent binding of ubiquitin to E2, which replaces E1. Finally, E3 ligase forms an isopeptide bond between the carboxy-terminus of ubiquitin and a lysine residue on the substrate protein. Numerous E3 ligases provide specificity in that each can modify only a subset of substrate proteins. Further specificity is achieved by post-translational modification of substrate proteins, including, but not limited to, phosphorylation. Examples of protein degradation inhibitors include, but are not limited to, compounds listed in Table G.

As used herein, a "PI3K-Akt signaling inhibitor" refers to a compound that inhibits one or more proteins involved in PI3K-Akt signaling. Akt is a serine/threonine kinase (also known as protein kinase B or PKB) that regulates diverse cellular functions, such as metabolism, growth, proliferation, survival, transcription, and protein synthesis. The Akt signaling cascade is activated by receptor tyrosine kinases, integrins, B and T cell receptors, cytokine receptors, G-protein-coupled receptors, and other stimuli that induce production of phosphatidylinositol (3,4,5) trisphosphates (PIP3) by phosphoinositide 3-kinase (PI3K). These lipids serve as plasma membrane docking sites for proteins that harbor pleckstrin-homology (PH) domains, including Akt and its upstream activator PDK1. At the membrane, PDK1 phosphorylates Akt, leading to partial activation of Akt. Phosphorylation of Akt by mTORC2 stimulates full enzymatic activity. Members of the PI3K-related kinase (PIKK) family, including DNA-PK, can also phosphorylate Akt. Akt is dephosphorylated by protein phosphatase 2A (PP2A) and the PH-domain leucine-rich-repeat-containing protein phosphatases (PHLPP1/2). In addition, the tumor suppressor phosphatase and tensin homolog (PTEN) inhibits Akt activity by dephosphorylating PIP3. There are three highly related isoforms of Akt (Akt1, Akt2, and Akt3), which phosphorylate substrates containing the consensus phosphorylation motif RxRxxS/T. Examples of inhibitors of PI3K-Akt signaling include, but are not limited to, compounds that inhibit Akt (i.e., compounds that inhibit the activation of Akt), compounds that inhibit PI3K, compounds that inhibit PKC, and compounds that inhibit PDK1. Examples of PI3K-Akt signaling inhibitors include, but are not limited to, compounds listed in Table H.

As used herein, a "cAMP response element binding protein (CREB) activator" refers to a compound that binds and activates CREB or a compound that binds and activates a protein involved in the activation of CREB. In some embodiments, a CREB activator may increase the concentration of CREB. CREB is a transcription factor of the leucine zipper family of DNA binding proteins. CREB binds as a homodimer to the cAMP-responsive element (CRE), thereby increasing or decreasing the transcription of the downstream genes. Examples of proteins involved in the activation of CREB include, but are not limited to, PKA and Ca2+/calmodulin-dependent protein kinase. Genes whose regulated by CREB include, but are not limited to, c-fos, BDNF, tyrosine hydroxylase, neuropeptides (e.g., assomatostatin, enkephalin, VGF, corticotropin-releasing hormone), and genes involved in the mammalian circadian clock (e.g., PER1, PER2). Examples of CREBs include, but are not limited to, CREB1, CREB2, CREB3, CREB5, CREB3-like protein 1 (CREB3L1), CREB3L2, CREB3L3, and CREB3L4. An example of a CREB activator is AC102 (see Table I).

As used herein, the term "balance loss" refers to a deficiency in the vestibular system or vestibular function of a subject that causes the subject to feel unsteady, for example, when standing or walking. Balance loss related to the ear also causes vertigo (spinning) and nausea. Diseases and disorders that are related to balance loss (i.e., caused by balance loss, or cause balance loss) include, but are not limited to, benign paroxysmal positional vertigo (BPPV), labyrinthitis (e.g., vestibular neuronitis, cochlear neuronitis), trauma (i.e., injury to the ear or skull, injury caused by surgery to the ear or skull), Meniere's disease, perilymph fistula, superior canal dehiscence syndrome, and bilateral vestibulopathy. Balance loss may also be caused by medication, stress, anxiety, and aging.

DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
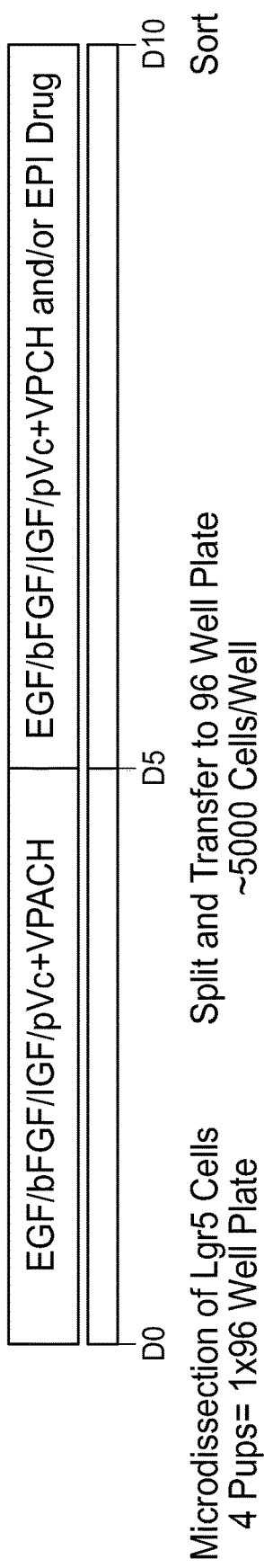
FIG. 1 is a timeline for the screening of Lgr5+ cells for drugs affecting proliferation.

Hair cells transduce sound via an apical stereociliary bundle that couples vibration-induced displacement to ion-channel gating. Damage and death of cochlear hair cells, which occurs in a high percentage of the population, is a cause of widespread hearing loss due to the lack of a mechanism for hair cell replacement. And damage and death of vestibular hair cells can result in balance loss or impairment.

Lgr5, an epithelial stem cell marker, was recently shown to be expressed in supporting cells of the inner ear (e.g., cochlear supporting cells) that surround the hair cells, and the Lgr5-expressing cells could be induced to proliferate when stimulated by Wnt in the normally post-mitotic cochlear sensory epithelium. Indeed, consistent with a progenitor role, supporting cells that expressed Lgr5 gave rise to new Lgr5-positive cells by propagation and to hair cells that were Lgr5-negative, whereas supporting cells that did not express this receptor did not give rise to hair cells. Consistent with its role in upstream regulation of transcription factor Atoh1, which is a master regulator of hair cell differentiation, upregulation of Wnt also increased hair cell differentiation. This combination of the ability to divide in response to Wnt signaling and the potency to differentiate into hair cells suggested that Lgr5 cells were acting as progenitor cells of the cochlear epithelium. Lgr5+ cells showed a limited capacity to regenerate spontaneously after damage, but their ability to divide and differentiate in response to Wnt stimulation and transdifferentiate in response to Notch inhibition was limited and only observed in neonatal animals.

Although these data supported a role of Lgr5+ cells as inner ear (e.g., cochlear) progenitor cells, and some expansion of the cells could be achieved by propagation as cochlear spheres, the heterogeneous cell populations suggested that other signaling pathways may be involved in stem cell expansion and hair cell differentiation. Furthermore, spontaneous regeneration capacity was lost after the first postnatal week, and changes in gene expression of these progenitors resulted in a loss in sphere-forming capacity in the adult mouse cochlea. Efforts to replace hair cells have concentrated on supporting cell transdifferentiation to hair cells, but regenerating a functional cochlea or vestibule would require both stimulating these cells to divide and differentiating them to hair cells. Here, by employing a screen, we identified pathways and small molecules that promoted the proliferation and/or differentiation of inner ear supporting cells (e.g., Lgr5-expressing inner ear supporting cells of the cochlea or the vestibule). These expanded inner ear cells can be used, e.g., for identifying compounds that can be used to treat hearing loss in mammals. Expanded inner ear cells (e.g., Lgr5+ inner ear cells) from transgenic animals comprising reporter genes for inner ear supporting cell and hair cell markers (e.g., Lgr5 and Atoh1 reporter genes, respectively) are particularly useful.

Compounds that Promote Proliferation and/or Differentiation of Inner Ear Supporting Cells Examples of compounds that promote the proliferation and expansion of inner ear supporting cells (e.g., Lgr5+ inner ear supporting cells) include, but are not limited to, a retinoid receptor signaling activator (see, e.g., Table K); a Wnt signaling activator set forth in Table A; a bone morphogenetic protein (BMP) signaling inhibitor set forth in Table B; a cyclin-dependent kinase (CDK) activator set forth in Table C; an E box-dependent transcriptional activator set forth in Table D; a Notch signaling activator set forth in Table E; a histone deacetylase (HDAC) inhibitor set forth in Table F; a protein degradation inhibitor set forth in Table G; a PI3K-Akt signaling inhibitor set forth in Table H; and a cAMP response element binding protein (CREB) activator set forth in Table I.

Examples of compounds that promote the differentiation of inner ear supporting cells (e.g., Lgr5+ inner ear supporting cells) into inner ear hair cells (e.g., atonal homolog 1 (Atoh1)+ inner ear hair cells) include, but are not limited to, a retinoid receptor signaling activator (see, e.g., Table K); a Wnt signaling activator set forth in Table A; a BMP signaling inhibitor set forth in Table B; a CDK activator set forth in Table C; an E box-dependent transcriptional activator set forth in Table D; an HDAC inhibitor set forth in Table F; a protein degradation inhibitor set forth in Table G; a PI3K-Akt signaling inhibitor set forth in Table H; a CREB activator set forth in Table I; and a Notch signaling inhibitor set forth in Table J.

A number of compounds that support or promote the proliferation of inner ear supporting cells (e.g., Lgr5+ inner ear supporting cells) and/or promote the differentiation of inner ear supporting cells (e.g., Lgr5+ inner ear supporting cell) into inner ear hair cells (e.g., Atoh1+ inner ear hair cells) are set forth in Table 1.

A number of compounds that support or promote the proliferation of inner ear supporting cells (e.g., Lgr5+ inner ear supporting cells) are described herein, and include one or more of TTNPB, Compound A, Compound B, Compound C, 1-Azakenpaullone, BIO, WAY-316606, LDN-193189, and Alsterpaullone.

A number of compounds that promote the differentiation of inner ear supporting cells (e.g., Lgr5+ inner ear supporting cell) into to inner ear hair cells (e.g., Atoh1+ inner ear hair cells) are described herein, and include one or more of vorinostat, Compound A, Compound B, Compound C, 1-Azakenpaullone, BIO, WAY-262611, NP031112, MG-132, IM-12, Trichostatin A, HLY78, and PF03084014.

In some embodiments of the invention, derivatives of the compounds listed in Tables A-K may also be used to promote the proliferation and/or expansion of inner ear supporting cells (e.g., Lgr5+ inner ear supporting cells) or to promote the differentiation of inner ear supporting cells (e.g., Lgr5+ inner ear supporting cells) into inner ear hair cells (e.g., Atoh1+ inner ear hair cells). A derivative of a compound listed in Tables A-K is a small molecule that differs in structure from the parent compound, but retains the ability to promote the proliferation and expansion of to inner ear supporting cells (e.g., Lgr5+ inner ear supporting cells) or to promote the differentiation of inner ear supporting cells (e.g., Lgr5+ inner ear supporting cells) into inner ear hair cells (e.g., Atoh1+ inner ear hair cells). A derivative of a compound may change its interaction with certain other molecules or proteins relative to the parent compound. A derivative of a compound may also include a salt, an adduct, or other variant of the parent compound. In some embodiments of the invention, any derivative of a compound described herein (e.g., any one compound of the compounds listed in Tables A-K) may be used instead of the parent compound. In some embodiments, any derivative of a compound listed in Tables A-I and K may be used in a method of producing an expanded population of inner ear supporting cells. In some embodiments, any derivative of a compound listed in Tables A-D and F-K may be used in a method of promoting differentiation of a population of inner ear supporting cells into a population of inner ear hair cells.

TABLE A

| Compound | Target |
| --- | --- |
| CHIR-98023 | GSK-3β |
| CHIR-99021 | GSK-3β |
| CHIR-99030 | GSK-3β |
| Hymenialdisine | GSK-3β |
| debromohymeialdisine | GSK-3β |
| dibromocantherelline | GSK-3β |
| Meridianine A | GSK-3β |
| alsterpaullone | GSK-3β |
| cazapaullone | GSK-3β |
| Aloisine A | GSK-3β |
| NSC 693868 (1H-Pyrazolo[3,4-b]quinoxalin-3-amine) | |
| Indirubin-3'-oxime (Indirubin-3'-monoxime; 3-[1,3-Dihydro-3-(hydroxyimino)-2H-indol-2-ylidene]-1,3-dihydro-2H-indol-2-one) | GSK-3β |

TABLE A-continued

| Compound | Target |
|---|---|
| A 1070722 (1-(7-Methoxyquinolin-4-yl)-3-[6-(trifluoromethyl)pyridin-2-yl]urea) | GSK-3β |
| L803 | GSK-3β |
| L803-mts | GSK-3β |
| TDZD8 | GSK-3β |
| NP00111 | GSK-3β |
| HMK-32 | GSK-3β |
| Manzamine A | GSK-3β |
| Palinurin | GSK-3β |
| Tricantin | GSK-3β |
| IM-12 (3-(4-Fluorophenylethylamino)-1-methyl-4-(2-methyl-1H-indol-3-yl)-1H-pyrrole-2,5-dione) | GSK-3β |
| NP031112 | GSK-3β |
| NP00111 | GSK-3β |
| NP031115 | GSK-3β |
| VP 2.51 | GSK-3β |
| VP2.54 | GSK-3β |
| VP 3.16 | GSK-3β |
| VP 3.35 | GSK-3β |
| HLY78 (4-Ethyl-5,6-Dihydro-5-methyl-[1,3]dioxolo[4,5-j]phenanthridine, 4-Ethyl-5-methyl-5,6-dihydro-[1,3]dioxolo[4,5-j]phenanthridine) | Axin |
| WAY-262611 ((1-(4-(Naphthalen-2-yl)pyrimidin-2-yl)piperidin-4-yl)methanamine)) | Dickkopf-1 (DKK1) |
| BHQ880 | DKK1 |
| NCI8642 | DKK1 |
| gallocyanine dyes | DKK1 |
| Compounds 3-8 (Moore et al., *J. Med. Chem.*, 2009; 52: 105) | secreted frizzled-related protein 1 (sFRP-1) |
| WAY-316606 | sFRP-1 |

TABLE B

| Compound | Target |
|---|---|
| A01 (Cao et al., *Scientific Reports*, 2014; 4: 4965) | SMAD1/5/8 |
| A17 (Cao et al., *Scientific Reports*, 2014; 4: 4965) | SMAD1/5/8 |

TABLE C

| Compound | Target |
|---|---|
| Cerivastatin (Baycol; Lipobay) | p27Kip1 |
| Alsterpaullone 2-cyanoethyl | p27Kip1 |
| SJ403 | p27Kip1 |

TABLE D

Figure 7:
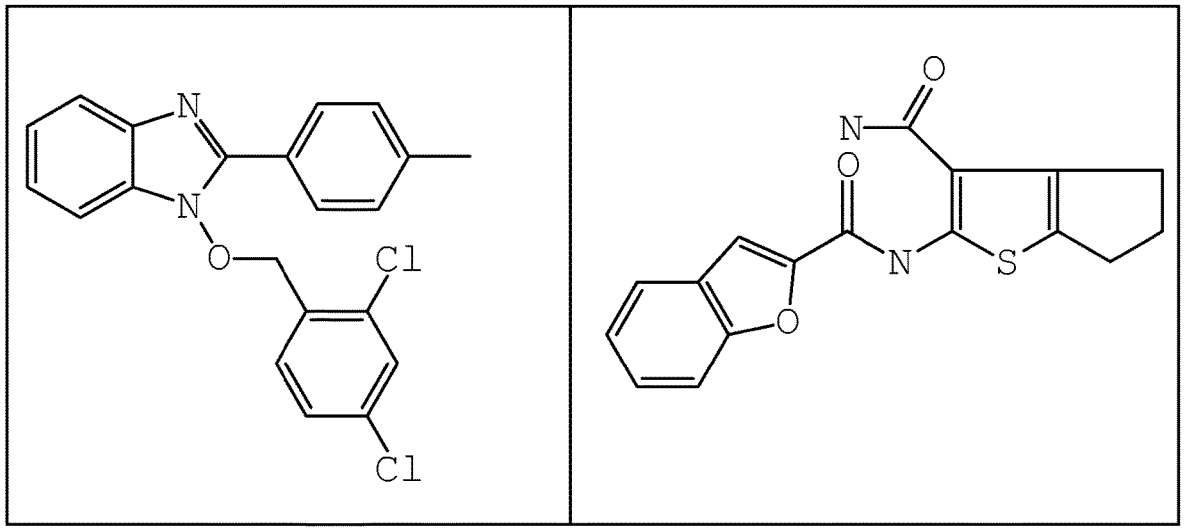
FIG. 7 is structures of specific screening compounds Compound A (see WO 2009/100438), Compound B (see WO 2009/100438), Compound C (see WO 2009/100438), and BI8622 (from Peter et al., EMBO Mol Med. 2014 December; 6(12): 1525-1541).
Figure 7:
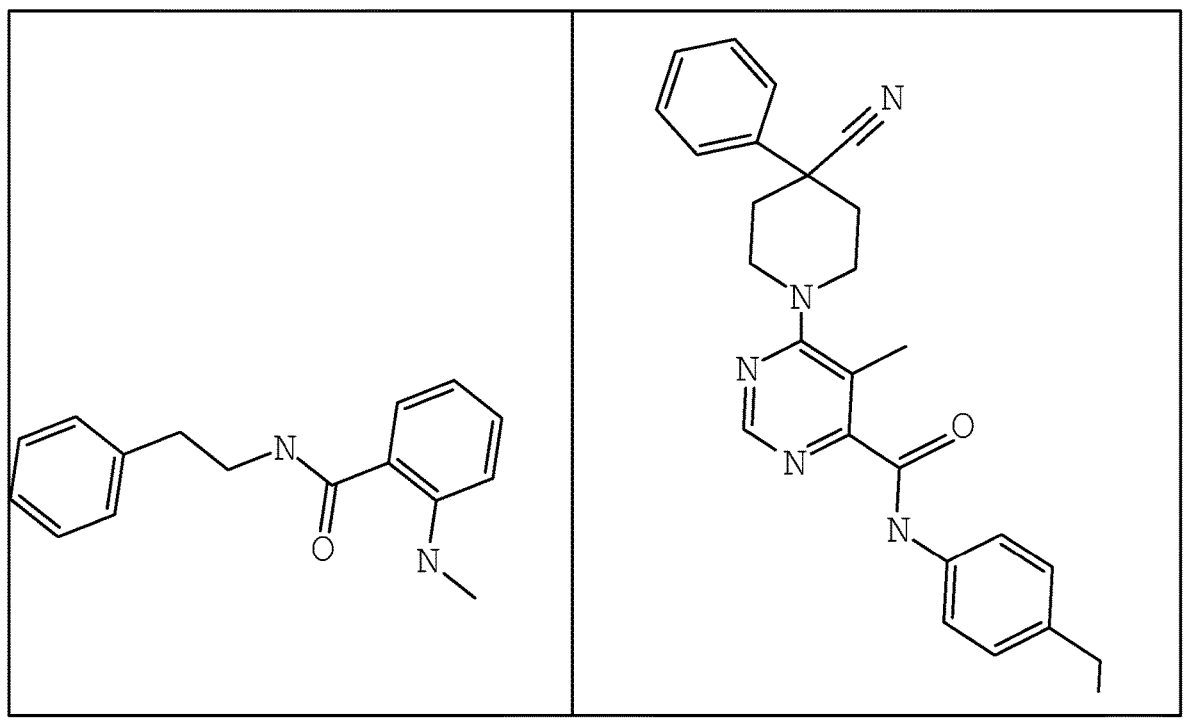

| Compound | Target |
|---|---|
| Compound A (See FIG. 7) | Atoh1 |
| Compound B (See FIG. 7) | Atoh1 |
| Compound C (See FIG. 7) | Atoh1 |
| 1-Azakenpaullone (Pyrido[3',2':2,3]azepino[4,5-b]indol-6(5H)-one, 9-bromo-7,12-dihydro-) | Atoh1 |
| 2-(N)-benzyl ellipticene | Atoh1 |

TABLE E

| Compound | Target |
|---|---|
| Delta/Serrate/Lag-2 peptide | Notch receptor |

TABLE F

| Compound | Target |
|---|---|
| Vorinostat (rINN; suberanilohydroxamic acid; suberoylanilide hydroxamic acid; SAHA (suberoyl + anilide + hydroxamic acid abbreviated); N-Hydroxy-N'-phenyloctanediamide; Zolinza ®) | HDAC class I (HDAC1, 2, 3, and 8) and HDAC class II (IIa: HDAC4, 5, 7, and 9; IIb: 6 and 10) |
| Trichostatin A (TSA; (2E,4E,6R)-7-(4-(Dimethylammo)phenyl)-N-hydroxy-4,6-dimethyl-7-oxo-2,4-heptadienamide) | HDAC class I (HDAC1, 2, 3, and 8) and HDAC class II (IIa: HDAC4, 5, 7, and 9; IIb: 6 and 10) |
| belinostat (PXD101; Beleodaq) | HDAC |
| Valproic acid (VPA; sodium valproate; Sodium 2-propylpentanoate) | HDAC |
| FK 228 (Depsipeptide; FR 901228; Romidepsin; Cyclo[(2Z)-2-amino-2-butenoyl-L-valyl-(3S,4E)-3-hydroxy-7-mercapto-4-heptenoyl-D-valyl-D-cysteinyl], cyclic (3-5) disulfide) | HDAC class I (HDAC1, 2, 3, and 8), HDAC4, and HDAC6 |
| Sodium butyrate (Butanoic acid sodium salt; NaB) | HDAC |
| LMK 235 (N-[[6-(Hydroxyamino)-6-oxohexyl]oxy]-3,5-dimethylbenzamide) | HDAC4 and HDAC5 |
| Scriptaid (N-Hydroxy-1,3-dioxo-1H-benz[de]isoquinoline-2(3H)-hexanamide) | HDAC |
| M 344 (4-(Diethylammo)-N-[7-(hydroxyamino)-7-oxoheptyl]benzamide) | HDAC |

TABLE F-continued

| Compound | Target |
|---|---|
| SBHA (N,N'-Dihydroxyoctanediamide; suberic bishydroxamate) | HDAC1 and HDAC3 |
| CBHA (m-carboxycinnamic acid bishydroxamide) | HDAC1 and HDAC3 |
| HMBA (hexamethylene bisacetamide). | HDAC |
| Tubacin (N-[4-[(2R,4R,6S)-4-[[(4,5-Diphenyl-2-oxazolyl)thio]methyl]-6-[4-(hydroxymethyl)phenyl]-1,3-dioxan-2-yl]phenyl]-N'-hydroxyoctanediamide) | HDAC6 |
| Sodium 4-phenylbutyrate (4-PB; sodium pheylbutyrate; 4-Phenylbutyric acid, sodium salt; 4-phenylbutyrate) | HDAC |
| MC 1568 (3-[5-(3-(3-Fluorophenyl)-3-oxopropen-1-yl)-1-methyl-1H-pyrrol-2-yl]-N-hydroxy-2-propenamide) | HDAC class IIa (HDAC4, 5, 7, and 9) |
| Compound 9 (Mai et al., *J. Med. Chem.*, 2005; 48: 3344) | HDAC class IIa (HDAC4, 5, 7, and 9) |
| Compound 24 (Mai et al., *J. Med. Chem.*, 2005; 48: 3344) | HDAC class IIa (HDAC4, 5, 7, and 9) |
| TC-H 106 (N1-(2-Aminophenyl)-N7-(4-methylphenyl)heptanediamide; Pimelic Diphenylamide 106) | HDAC class I (HDAC1, 2, 3, and 8) |
| Pyroxamide (N-Hydroxy-N'-3-pyridinyloctanediamide) | HDAC1 |
| NCH 51 (PTACH; 2-Methylpropanethioic acid S-[7-oxo-7-[(4-phenyl-2-thiazolyl)amino]heptyl] ester) | HDAC |
| NCH 31 | HDAC |
| PCI 34051 (N-Hydroxy-1-[(4-methoxyphenyl)methyl]-1H-indole-6-carboxamide) | HDAC8 |
| thiophene benzamide | HDAC1 and HDAC2 |
| KD 5170 (S-[2-[6-[[[4-[3-(Dimethylamino)propoxy]phenyl]sulfonyl]amino]-3-pyridinyl]-2-oxoethyl]ethanethioc acid ester) | HDAC class I (HDAC1, 2, 3, and 8) and HDAC class II (IIa: HDAC4, 5, 7, and 9; IIb: 6 and 10) |
| TCS HDAC6 20b (2-Methylpropanethioic acid-S-[(6S)-6-[[(1,1-dimethylethoxy)carbonyl]amino]-7-oxo-7-(tricyclo[3.3.1.1$^{3,7}$]dec-1-ylamino)heptyl] ester) | HDAC6 |
| NSC 3852 (5-Nitroso-8-quinolinol) | HDAC |
| NSC69603 | HDAC |
| NSC86371 | HDAC |
| NSC305819 | HDAC |
| CI 994 (N-acetyldinaline; Acetyldinaline; 4-(Acetylamino)-N-(2-aminophenyl)benzamide) | HDAC class I |
| LAQ824 | HDAC class I |
| LBH589 (panobinostat; Farydak) | pan-HDAC |
| MS275 (SNDX-275; entinostat) | HDAC1-3 |
| MGCD0103 (mocetinostat) | HDAC1-8 and 11 |
| UF 010 (4-Bromo-N'-butylbenzohydrazide) | HDAC1-3 |
| Cpd60 | HDAC1-3 |
| Romidepsin | HDAC1 and HDAC2 |
| MS-27-275 | HDAC |
| NaBu (n-butyrate) | HDAC |
| trapoxin | HDAC |
| Apicidin (Cyclo[(2S)-2-Amino-8-oxodecanoyl-1-methoxy-L-tryptophyl-L-isoleucyl-(2R)-2-piperidinecarbonyl]) | HDAC |
| depudesin | HDAC |
| EX 527 (6-Chloro-2,3,4,9-tetrahydro-1H-carbazole-1-carboxamide) | SIRT1 |
| AGK 2 (2-Cyano-3-[[5-(2,5-dichlorophenyl)-2-furanyl]-N-5-quinolinyl-2-propenamide) | SIRT2 |

TABLE F-continued

| Compound | Target |
| --- | --- |
| AK 7 (N-(3-Bromophenyl)-3-[(hexahydro-1H-azepin-1-yl)sulfonyl]benzamide) | SIRT2 |
| SirReal2 (2-[(4,6-Dimethyl-2-pyrimidinyl)thio]-N-[5-(1-naphthalenylmethyl)-2-thiazolyl]acetamide) | SIRT2 |
| Salermide (N-[3-[[(2-Hydroxy-1-naphthalenyl)methylene]amino]phenyl]-α-methylbenzeneacetamide) | SIRT1 and SIRT2 |
| Splitomicin (1,2-Dihydro-3H-naphtho[2,1-b]pyran-3-one) | Sir2p (yeast form of SIRT1) |

TABLE G

| Compound | Target |
| --- | --- |
| MG132 (Z-LLL-al, Z-Leu-Leu-Leu-CHO; N-[(Phenylmethoxy)carbonyl]-L-leucyl-N-[(1S)-1-formyl-3-methylbutyl]-L-leucinamide) | proteasome |
| MG262 (Z-Leu-Leu-Leu-B(OH)2) | proteasome |
| MG115 (Z-Leu-Leu-Nva-CHO) | proteasome |
| Z-Leu-Leu-Phe-CHO (Z-LLF-CHO) | proteasome |
| N-Acetyl-leucyl-leucyl-norleucinal (Ac-Leu-Leu-Nle-CHO) | proteasome |
| N-acetyl-leucyl-leucyl-methional (Ac-Leu-Leu-Met-CHO) | proteasome |
| N-benzyloxycarbonyl-isoleucyl-γ-t-butyl-glutamyl-alanyl-leucinal (Z-Ile-Glu(OtBu)-Ala-Leu-CHO) | proteasome |
| N-benzyloxycarbonyl-leucyl-leucyl-leucinal (Z-Leu-Leu-Leu-CHO), | proteasome |
| N-benzyloxycarbonyl-leucyl-leucyl-tyrosyl α-keto aldehyde (Z-Leu-Leu-Tyr-COCHO) | proteasome |
| N-benzyloxycarbonyl-leucyl-leucyl-phenylalanal (Z-Leu-Leu-Phe-CHO) | proteasome |
| N-benzyloxycarbonyl-leucyl-leucyl-leucyl boronic acid (Z-Leu-Leu-Leu-B(OH)$_2$) | proteasome |
| Bortezomib (PS-341; Velcade; Neomib; Bortecad) | proteasome |
| Lactacystin ((2R,3S,4R)-3-Hydroxy-2-[(1S)-1-hydroxy-2-methylpropyl]-4-methyl-5-oxo-2-pyrrolidinecarboxy-N-acetyl-L-cysteine thioester) | proteasome |
| Disulfiram (Antabuse and Antabus) | proteasome |
| Epigallocatechin-3-gallate (Epigallocatechin gallate; EGCG) | proteasome |
| Salinosporamide A | proteasome |
| Carfilzomib (Kyprolis) | proteasome |
| epoxomicin | proteasome |
| Ixazomib (Ninlaro; MLN2238) | proteasome |
| ixazomib citrate (MLN9708) | proteasome |
| PS-341 | proteasome |
| VLX1500 (b-AP15) | proteasome |
| clasto-Lactacystin beta Lactone | proteasome |
| Gliotoxin (Aspergillin; (3R,5aS,6S,10aR)-2,3,5a,6-Tetrahydro-6-hydroxy-3-(hydroxymethyl)-2-methyl-10H-3,10a-epidithiopyrazino[1,2-a]indole-1,4-dione) | proteasome |
| AM 114 (3,5-Bis-[benzylidene-4-boronic acid]-1-methylpiperidin-4-one) | proteasome |
| PSI (N-[(Phenylmethoxy)carbonyl]-L-isoleucyl-L-α-glutamyl-tert-butyl ester-N-[(1S)-1-formyl-3-methylbutyl]-L-alaninamide) | proteasome |
| Oprozomib (ONX 0912) | proteasome |
| Delanzomib (CEP-18770) | proteasome |
| BI8622 | Huwe1 (E3 ubiquitin ligase) |
| BI8626 | Huwe1 (E3 ubiquitin ligase) |

TABLE H

| Compound | Target |
| --- | --- |
| MLN4929 (Pevonedistat) | Akt |
| API-2 (Triciribine; NSC 154020; TCN; 1,5-Dihydro-5-methyl-1-β-D-ribofuranosyl-1,4,5,6,8-pentaazaacenaphthylen-3-amine; Akt/protein kinase B signaling inhibitor-2) | Akt |
| API-1 (4-Amino-5,8-dihydro-5-oxo-8-β-D-ribofuranosyl-pyrido[2,3-d]pyrimidine-6-carboxamide) | Akt |
| GSK 690693 (4-[2-(4-Amino-1,2,5-oxadiazol-3-yl)-1-ethyl-7-[(3S)-3-piperidinylmethoxy)-1H-imidazo[4,5-c]pyridin-4-yl]-2-methyl-3-butyn-2-ol) | Akt |
| 10-DEBC hydrochloride (10-[4'-(N,N-Diethylamino)butyl]-2-chlorophenoxazine hydrochloride) | Akt |
| FPA124 (Dichloro[(2Z)-2-[(4-oxo-4H-1-benzopyran-3-yl)methylene]hydrazinecarbothioamide copper complex) | Akt |
| SC66 ((2E,6E)-2,6-Bis(4-pyridinylmethylene)cyclohexanone) | Akt |
| LY 294002 hydrochloride (2-(4-Morpholinyl)-8-phenyl-4H-1-benzopyran-4-one hydrochloride) | PI3K |
| wortmannin | PI3K |
| PI 103 | PI3K |
| Quercetin (2-(3,4-Dihydroxyphenyl)-3,5,7-trihydroxy-4H-1-benzopyran-4-one) | PI3K and PKC |
| PHT 427 (4-Dodecyl-N-1,3,4-thiadiazol-2-yl-benzenesulfonamide) | Akt and PDK1 |
| GSK 2334470 ((3S,6R)-1-[6-(3-Amino-1H-indazol-6-yl)-2-(methylamino)-4-pyrimidinyl]-N-cyclohexyl-6-methyl-3-piperidinecarboxamide) | PDK1 |

TABLE H-continued

| Compound | Target |
| --- | --- |
| Fisetin (2-(3,4-Dihydroxyphenyl)-3,7-dihydroxy-4H-1-benzopyran-4-one) | PI3K, Akt |
| OSU 03012 (2-Amino-N-[4-[5-(2-phenanthrenyl)-3-(trifluoromethyl)-1H-pyrazol-1-yl]phenyl)acetamide) | Akt and PDK1 |
| PIT 1 (N-[[(3-Chloro-2-hydroxy-5-nitrophenyl)amino]thioxomethyl]benzamide) | Akt |

TABLE I

| Compound | Target |
| --- | --- |
| AC102 (6-fluoro-9-methyl-β-carboline; 6F9MβC) | CREB |

TABLE J

| Compound | Target |
| --- | --- |
| LY411575 (LSN-411575; Compound 5; benzeneacetamide; N-[(1s)-2-[[(7s)-6,7-dihydro-5-methyl-6-oxo-5H-dibenz[b,d]azepin-7-yl]amino]-1-methyl-2-oxoethyl]-3,5-difluoro-α-hyroxy-(αS)-); N2-[(2S)-2-(3,5-Difluorophenyl)-2-hydroxyethanoyl]-N1-[(7S)-5-methyl-6-oxo-6,7-dihydro-5H-dibenzo[b,d]azepin-7-yl]-L-alaninamide) | γ-secretase |
| L-685458 ((5S)-(tert-Butoxycarbonylamino)-6-phenyl-(4R)-hydroxy-(2R)-benzylhexanoyl)-L-leucy-L-phenylalaninamide; LY-685458; GSI-X) | γ-secretase |
| DBZ (Dibenzazepine; YO-01027; GSI-XX, deshydroxy LY-411575; N-[(1S)-2-[[(7S)-6,7-Dihydro-5-methyl-6-oxo-5H-dibenz[b,d]azepin-7-yl]amino]-1-methyl-2-oxoethyl]-3,5-difluorobenzeneacetamide) | γ-secretase |
| MRK560 (N-[cis-4-[(4-Chlorophenyl)sulfonyl]-4-(2,5-difluorophenyl)cyclohexyl]-1,1,1-trifluoromethanesulfonamide) | γ-secretase |
| MRK-003 | γ-secretase |
| MK-0752 | γ-secretase |
| Compound W (CW; 3,5-Bis(4-nitrophenoxy)benzoic acid) (Okochi et al., J.Biol.Chem., 2006; 281: 7890; Ford et al., J Neurosci Meth., 2008; 168: 465-474) | γ-secretase |
| Compound E (GSI-XXI) (Olsauskas-Kuprys et al., Onco Targets Ther., 2013; 6: 943) | γ-secretase |
| BMS 2289948 (4-chloro-N-(2,5-difluorophenyl)-N-((1R)-{4-fluoro-2-[3-(1H-imidazol-1-yl)propyl]phenyl}ethyl)benzenesulfonamide hydrochloride) | γ-secretase |
| BMS-433796 ((S)-2-((S)-2-(3,5-difluorophenyl)-2-hydroxyacetamido)-N-((S,Z)-3-methyl-4-oxo-4,5-dihydro-3H-benzo[d][1,2]diazepin-5-yl)propanamide) | γ-secretase |
| IN973 | γ-secretase |
| Flurbiprofen bi((R)-Flurbiprofen; tarenflurbil; Flurizan; (R)-2-Fluoro-α-methyl[1,1'-biphenyl]-4-acetic acid) | γ-secretase |
| JLK2, JLK4, JLK6, JLK7 (7-Amino-4-chloro-3-methoxy-1H-2-benzopyran) | γ-secretase |
| Begacestat (GSI-953; 5-Chloro-N-[(1S)-3,3,3-trifluoro-1-(hydroxymethyl)-2-(trifluoromethyl)propyl]-2-thiophenesulfonamide) | γ-secretase |

TABLE J-continued

| Compound | Target |
| --- | --- |
| DFK167 | γ-secretase |
| PF-0308414 | γ-secretase |

TABLE K

| Compound | Target |
| --- | --- |
| TTNBP (RO 13-7410, arotinoid acid, AGN 191183) | RAR |
| ATRA | RAR |
| 9-cis RA | RAR |
| CD271 (6-(4-Methoxy-3-tricyclo[3.3.1.13,7]dec-1-ylphenyl)-2-naphthalenecarboxylic acid) | RAR |
| CD336 | RAR |
| CD-394 | RAR |
| CD437 (6-3-(1-adamantyl)-4-hydroXyphenyl)-2 naphthanoic acid) (6-(4-Hydroxy-3-tricyclo[3.3.1.13,7]dec-1-ylphenyl)-2-naphthalenecarboxylic acid) | RAR |
| CD666 ((E)-4-(1-hydroXy-1-(5,6,7,8-tetrahydro-5,5,8,8 tetramethyl-2-naphthyl)-2-propenyl)benzoic acid) | RAR |
| CD1530 (4-(6-Hydroxy-7-tricyclo[3.3.1.13,7]dec-1-yl-2-naphthalenyl)benzoic acid) | RAR |
| CD2019 (6-(3-(1-methylcycloheXyl)-4-methoXyphenyl)-2 naphthanoic acid) | RAR |
| CD2247 | RAR |
| CD2081 | RAR |
| CD2314 | RAR |
| CD2325 (4-[(E)-2-(3-(1-adamantyl)-4-hydroXyphenyl)-1 propenyl]benZoic acid) | RAR |
| CD2425 | RAR |
| CD2503 | RAR |
| CD2665 | RAR |
| BMS-270394 (enantiomer of BMS-189961) (3-Fluoro-4-[(R)-2-hydroxy-2-(5,5,8,8-tetramethyl-5,6,7,8-tetrahydro-naphthalen-2-yl)-acetylaminol-benzoic acid) | RAR |
| BMS-189961 (3-Fluoro-4-[2-hydroxy-2-(5,5,8,8-tetramethyl-5,6,7,8-tetrahydro-naphthalen-2-yl)-acetylamino]-benzoic acid) | RAR |
| 6-[3-(adamantan-1-yl)-4-(prop-2-ynyloxy)phenyl]naphthalene-2-carboxylic acid | RAR |
| 5-[(E)-3-oxo-3-(5,5,8,8-tetrahydronaphthalene-2-yl)propenyl]thiophene-2-carboxylic acid | RAR |
| Palovarotene (4[(1E)-2-[5,6,7,8-Tetrahydro-5,5,8,8-tetramethyl-3-(1H-pyrazol-1-ylmethyl)-2-naphthalenyl]-ethenyl]-benzoic acid; R667; CLM-001, RG667) | RAR |
| CH-55 (4-[(E)-3-(3,5-Di-tert-butyl-phenyl)-3-oxo-propenyl]-benzoic acid) | RAR |
| Docosahexaenoic acid (DHA; (4Z,7Z,10Z,13Z,16Z,19Z)-4,7,10,13,16,19-Docosahexaenoic acid) | RXR |
| CD 3254 (3-[4-Hydroxy-3-(5,6,7,8-tetrahydro-3,5,5,8,8-pentamethyl-2-naphthalenyl)phenyl]-2-propenoic acid) | RXR |
| 9 cis-RA | RXR |
| 3-cis-retinoic acid (Accutane; isotretinoin; 13-cis-Retinoic acid) | RXR |
| LG 100754 ((2E,4E,6Z)-3-Methyl-7-(5,6,7,8-tetrahydro-5,5,8,8-tetramethyl-3-propoxy-3-naphthalenyl)-2,4,6-octatrienoic acid) | RXR |
| SR 11237 (BMS 649; 4-[2-(5,6,7,8-Tetrahydro-5,5,8,8-tetramethyl-2-naphthalenyl)-1,3-dioxolan-2-yl]-benzoic acid) | RXR |
| Fluorobexarotene (2-Fluoro-4-[1-(5-,6,7,8-tetrahydro-3,5,5,8,8-pentamethyl-2-naphthalenyl)ethenyl]benzoic acid) | RXR |

TABLE K-continued

| Compound | Target |
|---|---|
| LGD1069<br>(4-[1-(3,5,5,8,8-pentamethyl-5,6,7,8-tetrahydro-2-naphthyl)ethenyl] acid) | RXR |
| LG100268<br>(6-[1-(3,5,5,8,8-pentamethyl-5,6,7,8-tetrahydronaphthalen-2-yl)cyclopropyl]nicotinic acid) | RXR |
| LG100754<br>(2E,4E,6Z)-3-Methyl-7-(5,6,7,8-tetrahydro-5,5,8,8-tetramethyl-3-propoxy-2-naphthalenyl)-2,4,6-Octatrienoic acid) | RXR |
| Compounds 1-11<br>(Wagner et al., J. Med. Chem., 2009; 52: 5950) | RXR |
| HX 630<br>(4-(7,8,9,10-Tetrahydro-7,7,10,10-tetramethylbenzo[b]naphtho[2,3-f][1,4]thiazepin-12-yl-benzoic acid) | RXR |
| HX 640 | RXR |
| HX 600 | RXR |
| TZ335 | RXR |
| Adapalene<br>(6-(4-Methoxy-3-tricyclo[3.3.1.1$^{3,7}$]dec-1-ylphenyl)-2-naphthalenecarboxylic acid, 6-[3-(1-Adamantyl)-4-methoxyphenyl]-2-naphthoic acid; CD-271; Differin) | RXR |
| Bexarotene<br>(4-[1-(5,6,7,8-Tetrahydro-3,5,5,8,8-pentamethyl-2-naphthalenyl)ethenyl]benzoic acid, LGD-1069; SR-11247; targretin; TRG) | RXR |
| Retinoic acid<br>(ATRA; Tretinoin; Vitamin A acid; all-trans-Retinoic acid) | RXR |
| 4-[N-methanesulfonyl-N-(5,5,8,8-tetramethyl-5,6,7,8-tetrahydro-2-naphthyl)amino]benzoic acid | RXR |
| 6-[N-ethyl-N-(3-isopropoxy-4-isopropylphenyl)amino]nicotinic acid (NEt-3IP) | RXR |
| 6-[N-ethyl-N-(3-isobutoxy-4-isopropylphenyl)amino]nicotinic acid (NEt-3IB | RXR |
| PA024 | RXR |
| AGN 194204 | RXR |
| CNX-013-B2 | RXR |
| UAB30 | RXR |
| IRX4204 | RXR |

In some embodiments, the one or more agents used to promote the proliferation and expansion of inner ear supporting cells (e.g., Lgr5+ inner ear supporting cells) or to promote the differentiation of inner ear supporting cells (e.g., Lgr5+ inner ear supporting cells) into inner ear hair cells (e.g., Atoh1+ inner ear hair cells) include a combination of agents, in which the agents target two or more (e.g., three, four, five, or more) of the following pathways, proteins, and DNA response elements: the retinoid receptor signaling pathway, the Wnt signaling pathway, the BMP signaling pathway, the CDK signaling pathway, the Notch signaling pathway, the protein degradation pathway, the PI3K-Akt signaling pathway, the cAMP-dependent pathway, histone deacetylase (HDAC), and/or E box DNA response element.

In some embodiments, the one or more agents used to promote the proliferation and expansion of inner ear supporting cells (e.g., Lgr5+ inner ear supporting cells) or to promote the differentiation of inner ear supporting cells (e.g., Lgr5+ inner ear supporting cells) into inner ear hair cells (e.g., Atoh1+ inner ear hair cells) include a combination of agents (e.g., a combination two agents each selected from the compounds set forth in Tables A-K, wherein the two agents are different from each other; a combination of three agents each selected from the compounds set forth in Tables A-K, wherein the three agents are different from each other; a combination of four agents each selected from the compounds set forth in Tables A-K, wherein the four agents are different from each other; and a combination of five agents each selected from the compounds set forth in Tables A-K, wherein the five agents are different from each other).

For example, if a combination of two agents each selected from the compounds set forth in Tables A-K is used to promote the proliferation and expansion of inner ear supporting cells (e.g., Lgr5+ inner ear supporting cells) or to promote the differentiation of inner ear supporting cells (e.g., Lgr5+ inner ear supporting cells) into inner ear hair cells (e.g., Atoh1+ inner ear hair cells), the two agents in the combination may be selected based on the combinations listed in Table L.

TABLE L

| Combination | Agent 1 chosen from | Agent 2 chosen from |
|---|---|---|
| 1 | Table A | Table A |
| 2 | Table A | Table B |
| 3 | Table A | Table C |
| 4 | Table A | Table D |
| 5 | Table A | Table E |
| 6 | Table A | Table F |
| 7 | Table A | Table G |
| 8 | Table A | Table H |
| 9 | Table A | Table I |
| 10 | Table A | Table J |
| 11 | Table A | Table K |
| 12 | Table B | Table B |
| 13 | Table B | Table C |
| 14 | Table B | Table D |
| 15 | Table B | Table E |
| 16 | Table B | Table F |
| 17 | Table B | Table G |
| 18 | Table B | Table H |
| 19 | Table B | Table I |
| 20 | Table B | Table J |
| 21 | Table B | Table K |
| 22 | Table C | Table C |
| 23 | Table C | Table D |
| 24 | Table C | Table E |
| 25 | Table C | Table F |
| 26 | Table C | Table G |
| 27 | Table C | Table H |
| 28 | Table C | Table I |
| 29 | Table C | Table J |
| 30 | Table C | Table K |
| 31 | Table D | Table D |
| 32 | Table D | Table E |
| 33 | Table D | Table F |
| 34 | Table D | Table G |
| 35 | Table D | Table H |
| 36 | Table D | Table I |
| 37 | Table D | Table J |
| 38 | Table D | Table K |
| 39 | Table E | Table E |
| 40 | Table E | Table F |
| 41 | Table E | Table G |
| 42 | Table E | Table H |
| 43 | Table E | Table I |
| 44 | Table E | Table J |
| 45 | Table E | Table K |
| 46 | Table F | Table F |
| 47 | Table F | Table G |
| 48 | Table F | Table H |
| 49 | Table F | Table I |
| 50 | Table F | Table J |
| 51 | Table F | Table K |
| 52 | Table G | Table G |
| 53 | Table G | Table H |
| 54 | Table G | Table I |
| 55 | Table G | Table J |
| 56 | Table G | Table K |
| 57 | Table H | Table H |
| 58 | Table H | Table I |
| 59 | Table H | Table J |
| 60 | Table H | Table K |
| 61 | Table I | Table I |

TABLE L-continued

| Combination | Agent 1 chosen from | Agent 2 chosen from |
|---|---|---|
| 62 | Table I | Table J |
| 63 | Table I | Table K |
| 64 | Table J | Table J |
| 65 | Table J | Table K |
| 66 | Table K | Table K |

Alternatively, the invention also contemplates methods that use one or more proteins involved in the retinoid receptor signaling pathway, the Wnt signaling pathway, the BMP signaling pathway, the CDK signaling pathway, the Notch signaling pathway, the protein degradation pathway, the PI3K-Akt signaling pathway, and/or the cAMP-dependent pathway to down-regulate or up-regulate the pathway to promote the proliferation and expansion of inner ear supporting cells (e.g., Lgr5+ inner ear supporting cells) or to promote the differentiation of inner ear supporting cells (e.g., Lgr5+ inner ear supporting cells) into inner ear hair cells (e.g., Atoh1+ inner ear hair cells).

In some embodiments of the methods, RAR and/or RXR may be used to up-regulate retinoid receptor signaling.

In some embodiments of the methods, RSPO, Norrin, Wnt3a, and/or Wnt5a may be used to up-regulate the Wnt signaling pathway.

In some embodiments of the methods, Noggin and/or Chordin may be used to down-regulate the BMP signaling pathway.

In some embodiments of the methods, CDKs and/or cyclins may be used to up-regulate the CDK signaling pathway.

In some embodiments of the methods, Delta/Serrate/Lag-2 peptide and/or Notch receptors may be used to up-regulate the Notch signaling pathway.

In some embodiments of the methods, the level of ubiquitin may be decreased to down-regulate the protein degradation pathway.

In some embodiments of the methods, the level of Akt, PI 3-kinase, and/or PDK1 may be decreased to down-regulate the PI3K-Akt signaling pathway.

In some embodiments of the methods, the level of CREB protein may be increased to up-regulate cAMP-dependent pathway.

In some embodiments of the methods, the level of one or more transcription factors that bind to the E box DNA response element may be increased to up-regulate E box-dependent transcription.

In some embodiments of the methods, the level of histone deacetylase (HDAC) may be decreased to down-regulate HDAC activity.

Alternatively, the invention also contemplates methods that use one or more growth factors to down-regulate or up-regulate one or more of the following pathways: retinoid receptor signaling pathway, the Wnt signaling pathway, the BMP signaling pathway, the CDK signaling pathway, the Notch signaling pathway, the protein degradation pathway, the PI3K-Akt signaling pathway, and/or the cAMP-dependent pathway, in order to promote the proliferation and expansion of inner ear supporting cells (e.g., Lgr5+ inner ear supporting cells) or to promote the differentiation of inner ear supporting cells (e.g., Lgr5+ inner ear supporting cells) into inner ear hair cells (e.g., Atoh1+ inner ear hair cells).

In some embodiments of the methods, the growth factors include, but are not limited to, epidermal growth factor (EGF), basic fibroblast growth factor (bFGF), and/or insulin-like growth factor (IGF1).

Transgenic Animals and Methods of Use

In one aspect, the invention provides non-human transgenic animals having two or more (e.g., two, three, or four or more) recombinant nucleic acid molecules stably integrated into their genome. The two or more recombinant nucleic acid molecules include at least a first recombinant nucleic acid molecule that comprises a first reporter gene (e.g., a fluorescent marker) under the control of a regulatory element of an inner ear supporting cell marker selected from the group consisting of Lgr5, Sox2, p27, Prox1, FGFR3, Glast, and Lfng (e.g., Lgr5), and a second recombinant nucleic acid molecule that comprises a second reporter gene under the control of a regulatory element of an inner ear hair cell marker selected from the group consisting of Atoh1, Myo7a, Cdh23, Pcdh15, Myo6, Myo1c, Tmc1, and Cav1.3 (e.g., Atoh1), wherein the first reporter gene is different from the second reporter gene.

The invention also contemplates using various genetic engineering techniques to generate one or more reporters in a cell or a transgenic animal. In some embodiments, various genetic engineering techniques can be used to generate two or more reporters in a cell or a transgenic animal. Examples of genetic engineering techniques include, but are not limited to, techniques that use the CRISPR/Cas system, techniques that use the Cre recombinase-loxP recombination system, techniques that use the Cre-Lox recombination syste, techniques that use the Flp-FRT recombination system, and techniques that use the RMCE (recombinase-mediated cassette exchange) system.

In some embodiments, the inner ear supporting cell marker is Lgr5 and the inner ear hair cell marker is Atoh1. In some embodiments, the regulatory element of an inner ear supporting cell marker is an Lgr5 promoter. In some embodiments, the regulatory element of an inner ear hair cell marker is an Atoh1 enhancer. In some embodiments, the Atoh1 enhancer is operably linked to an SV40 promoter or a globin promoter.

In some embodiments, the first reporter gene encodes a first fluorescent protein and the second reporter gene encodes a second fluorescent protein, in which the first fluorescent protein is different from the second fluorescent protein.

In some embodiments, the expression of Lgr5 results in expression of the first fluorescent marker (Lgr5 reporter transgene). In some embodiments, the expression of Atoh1 results in expression of the second fluorescent marker (Atoh1 reporter transgene). In preferred embodiments a mouse is obtained that contains the Lgr5 reporter protein and Atoh1 reporter protein transgenes in all of its somatic and germ cells. The first and second markers should be distinguishable from each other. In some embodiments, the first and second markers produce green and red fluorescence in the cells. Although fluorescent markers are exemplified herein, other markers (reporter genes) can also be used; Examples of suitable enzymes include horseradish peroxidase, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; examples of bioluminescent materials include luciferase, luciferin, and aequorin. Numerous others are known in the art. In some embodiments, one of the markers is green fluorescent protein or a derivative thereof, fluorescent proteins (e.g., green fluorescent protein (GFP), cyan fluorescent protein (CFP), red fluorescent protein (RFP), mCherry, Tag-RFP, etc.), luciferase which is a luminescent reporter (Ranella, Firefly, etc.), chomogenic (beta-Gal, etc.), etc. See e.g., Pollock et al., Trends in Cell Biology 9:57 (1999). Useful fluorescent proteins also include mutants and spectral variants of these proteins which retain the ability to fluoresce. See e.g., Shaner et al., Nat. Biotech. 22:1567 (2004), Tag-RFP (Shaner, N. C. et al., 2008 Nature Methods, 5(6), 545-551), Other fluorescent proteins that can be used in the methods described include, but are not limited to, AcGFP, AcGFP1, AmCyan, copGFP, CyPet, dKeima-Tandem, DsRed, dsRed-Express, DsRed-Monomer, DsRed2, AmCyan1, AQ143, AsRed2, Azami Green, Azurite, BFP, Cerulean, CFP, CGFP, Citrine, dTomato, dTomato-Tandem, EBFP, EBFP2, ECFP, EGFP, Emerald, EosFP, EYFP, GFP, mBanana, mCerulean, mCFP, mCherry, mCitrine, mECFP, mEmerald, mGrape1, mGrape2, mHoneydew, Midori-Ishi Cyan, mKeima, mKO, mOrange, mOrange2, mPlum, mRaspberry, mRFP1, mRuby, mStrawberry, mTagBFP, mTangerine, mTeal, mTomato, mTurquoise, mWasabi, PhiYFP, ReAsH, Sapphire, Superfolder GFP, T-HcRed-Tandem, HcRedl, JRed, Katuska, Kusabira Orange, Kusabira Orange2, mApple, Sapphire, TagCFP, TagGFP, TagRFP, TagRFP-T, TagYFP, tdTomato, Topaz, TurboGFP, Venus, YFP, YPet, ZsGreen, and ZsYellowl, all of which are known in the art, e.g., described in the literature or otherwise commercially available.

A "transgenic animal" is a non-human animal, such as a mammal, generally a rodent such as a rat or mouse, in which one or more of the cells of the animal includes a transgene as described herein. Other examples of transgenic animals include non-human primates, sheep, dogs, cows, goats, chickens, amphibians, and the like. A "transgene" is exogenous DNA that is integrated into the genome of a cell from which a transgenic animal develops and thus remains in the genome of the mature animal, thereby directing the expression of an encoded gene product in one or more cell types or tissues of the transgenic animal. Knock-in animals, which include a gene insertion, are included in the definition of transgenic animals.

A "Lgr5 reporter transgene" or "Atoh1 reporter transgene" as used herein refers to a construct that features a coding sequence for a reporter protein inserted downstream of an Lgr5 or Atoh1 promoter, so as to result in expression of the reporter protein in cells expressing Lgr5 or Atoh1. The promoter drives expression of the reporter protein, and transcription is stopped by a polyadenylation signal. The transgene is generally integrated into or occurs in the genome of the cells of a transgenic animal. Thus an Lgr5/Atoh1 transgenic animal as described herein is one in which at least one copy of an Lgr5 reporter transgene and at least one copy of an Atoh1 reporter transgene have been introduced into a cell of the animal, e.g., an embryonic cell of the animal, prior to development of the animal. A line of transgenic animals (e.g., mice, rats, guinea pigs, hamsters, rabbits, or other mammals) can be produced bearing an Lgr5 reporter transgene and an Atoh1 reporter transgene in some or (preferably) all of their cells. Methods known in the art for generating such transgenic animals would be used, e.g., as described below.

Methods known in the art for producing transgenic animals can be used to generate an animal, e.g., a mouse, which bears an Lgr5 reporter transgene or an Atoh1 reporter transgene (see, e.g., Barker et al., Nature. 2007 Oct. 25; 449(7165):1003 and Lumpkin et al., Gene Expr Patterns. 2003 August; 3(4):389, both of which are incorporated herein in their entirety). Such animals can be crossed to produce offspring that are homozygous for both the Lgr5 reporter transgene and Atoh1 reporter transgene, i.e., that have the Lgr5 reporter transgene and Atoh1 reporter transgene integrated into the genome.

For example, in one embodiment, a suitable vector including a sequence encoding the Lgr5 reporter transgene or Atoh1 reporter transgene is introduced into a cell, e.g., a fertilized oocyte or an embryonic stem cell. Such cells can then be used to create non-human transgenic animals in which said sequences have been introduced into their genome. These animals can then in turn be bred with other transgenic animals that express a recombinase, e.g., under the control of an Lgr5 or Atoh1 promoter that will turn on expression of the reporter protein in a specific cell or tissue, or at a specific time in development.

Methods for generating transgenic animals, particularly animals such as mice, via embryo manipulation and electroporation or microinjection of pluripotent stem cells or oocytes, are known in the art and are described, for example, in U.S. Pat. Nos. 4,736,866 and 4,870,009, 4,873,191, U.S. Ser. No. 10/006,611, "Transgenic Mouse Methods and Protocols (Methods in Molecular Biology)," Hofker and van Deursen, Editors (Humana Press, Totowa, N.J., 2002); and in "Manipulating the Mouse Embryo," Nagy et al., Editors (Cold Spring Harbor Laboratory Press, Cold Spring Harbor, N.Y., 2002), which are incorporated herein by reference in their entirety. Methods similar to those used to create transgenic mice can be used for production of other transgenic animals.

In general, in the present methods, a transgenic mouse as described herein is made by injecting a vector made as described herein into the pronucleus of a fertilized mouse oocyte (e.g., an oocyte from a mouse with an Lgr5 reporter gene knocked in, see Barker et al., Nature. 2007 Oct. 25; 449(7165):1003) and used for generation of a transgenic mouse with the Lgr5 reporter gene and Atoh1 reporter transgene expressed in all cells, using standard transgenic techniques, e.g., as described in "Transgenic Mouse Methods and Protocols (Methods in Molecular Biology)," Hofker and van Deursen, Editors (Humana Press, Totowa, N.J., 2002); U.S. Pat. Nos. 4,736,866 and 4,870,009, 4,873,191 and 6,791,006, and in Hogan, "Manipulating the Mouse Embryo," Nagy et al., Editors (Cold Spring Harbor Laboratory Press, Cold Spring Harbor, N.Y., 2002). The reporter genes can be maintained and expressed in all cells, e.g., on plasmids or stably integrated into the genome, using standard molecular techniques.

A transgenic founder Lgr5/Atoh1 animal can be identified based upon the presence of the Lgr5 reporter transgene and Atoh1 reporter transgene in its genome, for example by detecting the presence or expression of the reporter sequences or proteins in tissues or cells of the animals. A transgenic founder animal can then be used to breed additional animals carrying the transgene. Moreover, transgenic animals carrying the Lgr5 reporter transgene and Atoh1 reporter transgene can further be bred to other transgenic animals carrying other transgenes.

Vectors

The mice described herein can be made using vectors, e.g., expression vectors, containing a nucleic acid encoding the Lgr5 reporter transgene or Atoh1 reporter transgene as described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a nucleic acid encoding a Lgr5 reporter protein or Atoh1 reporter protein in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce the Lgr5 reporter and Atoh1 reporter, encoded by nucleic acids as described herein.

The recombinant expression vectors described herein can be designed for expression of the Lgr5 reporter and Atoh1 reporter proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, "Gene Expression Technology: Methods in Enzymology 185," Academic Press, San Diego, Calif. (1990). Alternatively, the recombinant expression vector can be transcribed and translated in vitro, for example using T7 promoter regulatory sequences and T7 polymerase.

In some embodiments, the Atoh1 enhancer described in Example 5 is used to drive expression of a reporter gene.

Cells

In another aspect, the invention provides isolated cells that include a nucleic acid molecule as described herein, e.g., a nucleic acid molecule encoding an Lgr5 reporter protein or Atoh1 reporter protein within a recombinant expression vector, or a nucleic acid molecule containing sequences that allow it to homologously recombine into a specific site of the host cell's genome. The terms "host cell" and "recombinant host cell" are used interchangeably herein. Such terms refer not only to the particular subject cell that was contacted with a nucleic acid molecule (e.g., a vector as described herein), but to the progeny or potential progeny of such a cell that also contain the nucleic acid molecule. Because certain modifications may occur in succeeding generations due to either mutation or environmental influences, such progeny may not, in fact, be identical to the parent cell, but are still included within the scope of the term as used herein so long as they also contain the nucleic acid molecule.

A host cell can be any prokaryotic or eukaryotic cell. For example, the cell can be a bacterial cell such as *E. coli*, insect cells, yeast or mammalian cells (such as Chinese hamster ovary cells (CHO), HEK, or COS cells). Other suitable host cells are known to those skilled in the art. Where the vector is a viral vector that can be produced from recombinant cells, e.g., retroviral vectors, the cells can be those that produce the viral vector.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. In some embodiments, naked DNA is simply applied to a cell. Where the vector is a viral vector, known infection protocols can be used.

For example, retroviral vectors can be used, e.g., as described in Robertson et al., Nature 323:445-448 (1986). Retroviruses generally integrate into the host genome with no rearrangements of flanking sequences, which is not always the case when DNA is introduced by microinjection or other methods.

Cells of the present invention also include those cells obtained from the transgenic animals described herein, e.g., cells from the tissues of those animals, that contain the nucleic acid molecule.

Identity of Sequences

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For the present methods, the percent identity between two amino acid sequences is determined using the Needleman and Wunsch ((1970) J. Mol. Biol. 48:444-453) algorithm, which has been incorporated into the GAP program in the GCG software package (available on the world wide web at gcg.com), using the default parameters, i.e., a Blossum 62 scoring matrix with a gap penalty of 12, a gap extend penalty of 4, and a frameshift gap penalty of 5.

Methods for constructing transgenes useful in the present methods are known in the art; see, e.g., Sambrook and Russell, "Molecular Cloning: A Laboratory Manual," Cold Spring Harbor Laboratory Press; 3rd Labman edition (Jan. 15, 2001); and Ausubel et al., Eds., "Short Protocols in Molecular Biology," Current Protocols; 5 edition (Nov. 5, 2002). In some embodiments, commercially-available vectors can be used in constructing the nucleic acid molecules described herein, e.g., pC4M-Fv2E (available from Ariad Pharmaceuticals, Cambridge, Mass.).

Methods of Screening

Included herein are methods for screening test compounds, such as polypeptides, polynucleotides, inorganic or organic large or small molecule test compounds (e.g., compounds listed in Tables A-K) to identify agents useful in the treatment of hearing loss associated with a loss of cochlear hair cells (e.g., cochlear hair cells in the inner ear).

The present disclosure provides a method for identifying a candidate agent for the treatment of hearing loss or balance loss associated with a loss of cochlear or vestibular hair cells, in which the method includes: (a) isolating a population of inner ear supporting cells (e.g., Lgr5+ inner ear supporting cells) from the transgenic mouse described herein; (b) maintaining the population of inner ear supporting cells under conditions sufficient to produce an expanded population of inner ear supporting cells; (c) administering a test compound to the expanded population of inner ear supporting cells; (d) detecting the expression levels of the first reporter gene and the second reporter gene in the expanded population of inner ear supporting cells in the presence of the test compound; and (e) selecting as a candidate agent for the treatment of hearing loss or balance loss a test compound that increases the expression level of the first reporter gene compared to the expression level of the first reporter gene in the absence of the test compound, and/or increases the expression level of the second reporter gene compared to the expression level of the second reporter gene in the absence of the test compound.

In some embodiments, the conditions sufficient to produce an expanded population of inner ear supporting cells comprise one or more agents set forth in Table 1.

The present disclosure also provides a method for identifying a candidate agent for the treatment of hearing loss or balance loss associated with a loss of cochlear or vestibular hair cells, in which the method includes: (a) providing a population of inner ear supporting cells having a stably integrated recombinant nucleic acid molecule that comprises a reporter gene under the control of a regulatory element of an inner ear supporting cell marker selected from the group consisting of Lgr5, Sox2, p27, Prox1, FGFR3, Glast, and Lfng; (b) maintaining the population of inner ear supporting cells under conditions sufficient to produce an expanded population of inner ear supporting cells, wherein the conditions comprise one or more agents selected from the group consisting of: (i) a retinoid receptor signaling activator, (ii) a Wnt signaling activator set forth in Table A, (iii) a BMP signaling inhibitor set forth in Table B, (iv) a CDK activator set forth in Table C, (v) an E box-dependent transcriptional activator set forth in Table D, (vi) a Notch signaling activator set forth in Table E, (vii) an HDAC inhibitor set forth in Table F, (viii) a protein degradation inhibitor set forth in Table G, (ix) a PI3K-Akt signaling inhibitor set forth in Table H, and (x) a CREB activator set forth in Table I; (c) administering a test compound to the expanded population of inner ear supporting cells; (d) detecting the expression level of the reporter gene in the expanded population of inner ear supporting cells in the presence of the test compound; and (e) selecting as a candidate agent for the treatment of hearing loss or balance loss a test compound that increases the expression level of the reporter gene compared to the expression level of the reporter gene in the absence of the test compound.

The present disclosure also provides a method for identifying a candidate agent for the treatment of hearing loss or balance loss associated with a loss of cochlear or vestibular hair cells, in which the method includes: (a) providing a population of inner ear supporting cells having a stably integrated recombinant nucleic acid molecule that comprises a reporter gene under the control of a regulatory element of an inner ear hair cell marker selected from the group consisting of Atoh1, Myo7a, Cdh23, Pcdh15, Myo6, Myo1c, Tmc1, and Cav1.3; (b) maintaining the population of inner ear supporting cells under conditions sufficient to produce an expanded population of inner ear supporting cells, wherein the conditions comprise one or more agents selected from the group consisting of: (i) a retinoid receptor signaling activator, (ii) a Wnt signaling activator set forth in Table A, (iii) a BMP signaling inhibitor set forth in Table B, (iv) a CDK activator set forth in Table C, (v) an E box-dependent transcriptional activator set forth in Table D, (vi) a Notch signaling activator set forth in Table E, (vii) an HDAC inhibitor set forth in Table F, (viii) a protein degradation inhibitor set forth in Table G, (ix) a PI3K-Akt signaling inhibitor set forth in Table H, and (x) a CREB activator set forth in Table I; (c) administering a test compound to the expanded population of inner ear supporting cells; (d) detecting the expression level of the reporter gene in the expanded population of inner ear cells in the presence of the test compound; and (e) selecting as a candidate agent for the treatment of hearing loss or balance loss a test compound that increases the expression level of the reporter gene compared to the expression level of the reporter gene in the absence of the test compound.

The present disclosure also provides methods of using hair cells to screen for ototoxins. The present disclosure also provides methods of identifying one or more compounds (e.g., compounds listed in Tables A-K) that exhibit protective properties against hair cell damage caused by ototoxins. In some embodiments, ototoxins include therapeutic drugs including antineoplastic agents, salicylates, quinines, and aminoglycoside antibiotics, contaminants in foods or medicinals, and environmental or industrial pollutants. The present disclosure also provides methods of using hair cells to identify synaptic connectivity. In some embodiments, the hair cells (e.g., Atoh1+ inner ear hair cells) used in these methods may be isolated from a mammal (e.g., a mouse or a human). In some embodiments, the hair cells (e.g., Atoh1+ inner ear hair cells) used in these methods may be differentiated from inner ear supporting cells (e.g., Lgr5+ inner ear supporting cells), as described by the methods provided herein.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds (e.g., compounds listed in Tables A-K and Table 1) can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds (e.g., compounds listed in Tables A-K and Table 1). A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound (e.g., a compound listed in Tables A-K and Table 1) is applied to a test sample, e.g., a cell or living tissue or organ, e.g., an eye, and one or more effects of the test compound is evaluated. In a cultured or primary cell for example, the ability of the test compound to increase expression of a supporting cell marker (e.g., Lgr5) and/or a hair cell marker (e.g., Atoh1).

In some embodiments, the test sample is, or is derived from (e.g., a sample taken from) an in vivo model of a disorder as described herein. For example, an animal model, e.g., a rodent such as a rat, can be used.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect an effect on expression of a supporting cell marker (e.g., Lgr5) and/or a hair cell marker (e.g., Atoh1).

A test compound (e.g., a compound listed in Tables A-K and Table 1) that has been screened by a method described herein and determined to increase expression of Lgr5 and/or Atoh1 can be considered a candidate compound. A candidate compound that has been screened, e.g., in an in vivo model of a disorder, e.g., an animal model of hearing loss, and determined to have a desirable effect on the disorder, e.g., on one or more symptoms of the disorder or on number of hair cells, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that increase expression of Lgr5 and/or Atoh1) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating disorders associated with loss of cochlear hair cells (e.g., cochlear hair cells in the inner ear), as described herein, e.g., hearing loss. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a disorder associated with loss of cochlear hair cells (e.g., cochlear hair cells in the inner ear), as described herein. The animal can be monitored for a change in the disorder, e.g., for an improvement in a parameter of the disorder, e.g., a parameter related to clinical outcome. In some embodiments, the parameter is hearing ability, and an improvement would be improved hearing response. In some embodiments, the subject is a human, e.g., a human with hearing loss, and the parameter is improved hearing.

Methods of Treatment

In some embodiments, the present disclosure provides novel therapeutic strategies for treating hearing loss or balance loss associated with a loss of cochlear hair cells (e.g., cochlear hair cells in the inner ear) or vestibular hair cells, respectively (i.e., conditions that would benefit from an increased proliferation and differentiation of inner ear supporting cells (e.g., Lgr5+ inner ear supporting cells)). In some embodiments, such strategies can promote an increase in the proliferation of inner ear supporting cells (e.g., Lgr5+ inner ear supporting cells) and/or an increase in the differentiation of the inner ear supporting cells (e.g., Lgr5+ inner ear supporting cells) into inner ear hair cells (e.g., Atoh1+ inner ear hair cells), thereby promoting the expansion and differentiation of a target cell into a mature cell of the inner ear, e.g., an auditory hair cell. In some embodiments, the methods and compositions described herein promote differentiation of target cells (e.g., inner ear supporting cells (e.g., Lgr5+ inner ear supporting cells)) to or towards mature cells of the inner ear, e.g., auditory hair cells (e.g., inner ear hair cells (e.g., Atoh1+ inner ear hair cells)) without promoting substantial cellular proliferation. In some embodiments, the methods and compositions described herein promote proliferation of target cells (e.g., inner ear supporting cells (e.g., Lgr5+ inner ear supporting cells)) without promoting substantial cellular proliferation.

In some embodiments, the present invention can be used to treat hair cell loss and any disorder that arises as a consequence of cell loss in the ear, such as hearing impairments, deafness, and vestibular disorders, for example, by promoting differentiation (e.g., complete or partial differentiation) of one or more cells (e.g., inner ear supporting cells (e.g., Lgr5+ inner ear supporting cells)) into one or more cells capable of functioning as sensory cells of the ear, e.g., hair cells (e.g., inner ear hair cells (e.g., Atoh1+ inner ear hair cells)).

In some embodiments, the hearing loss is sensorineural hearing loss, which can result from damage or malfunction of the cochlea, e.g., loss of or damage to the sensory epithelium resulting in loss of hair cells.

In some embodiments, the hearing loss can be for any reason, or as a result of any type of event. For example, because of a genetic or congenital defect; for example, a human subject can have been deaf since birth, or can be deaf or hard-of-hearing as a result of a gradual loss of hearing due to a genetic or congenital defect. In another example, the hearing loss can be a result of a traumatic event, such as a physical trauma to a structure of the ear, or a sudden loud noise, or a prolonged exposure to loud noises. For example, prolonged exposures to concert venues, airport runways, and construction areas can cause inner ear damage and subsequent hearing loss.

In some embodiments, hearing loss can be due to chemical-induced ototoxicity, wherein ototoxins include therapeutic drugs including antineoplastic agents, salicylates, quinines, and aminoglycoside antibiotics, contaminants in foods or medicinals, and environmental or industrial pollutants. In some embodiments, hearing loss can result from aging.

In some embodiments, the present disclosure provides methods of treating a subject having hearing loss or balance loss, in which:

(a) a therapeutically effective amount of one or more agents that promote proliferation of inner ear supporting cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; (v) an E box-dependent transcriptional activator set forth in Table D; (vi) a Notch signaling activator set forth in Table E; (vii) an HDAC inhibitor set forth in Table F; (viii) a protein degradation inhibitor set forth in Table G; (ix) a PI3K-Akt signaling inhibitor set forth in Table H; and (x) a CREB activator set forth in Table I; and/or (b) a therapeutically effective amount of one or more agents that promote differentiation of inner ear supporting cells into inner ear hair cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; (v) an E box-dependent transcriptional activator set forth in Table D; (vi) an HDAC inhibitor set forth in Table F; (vii) a protein degradation inhibitor set forth in Table G; (viii) a PI3K-Akt signaling inhibitor set forth in Table H; (ix) a CREB activator set forth in Table I; and (x) a Notch signaling inhibitor set forth in Table J, are administered to the subject, e.g., to the ear of a subject, to promote inner ear supporting cells (e.g., Lgr5+ inner ear supporting cells) proliferation and/or differentiation of inner ear supporting cells (e.g., Lgr5+ inner ear supporting cells) into inner ear hair cells (e.g., Atoh1+ inner ear hair cells) (direct therapy).

In some embodiments, the disclosure provides methods of treating a subject having hearing loss or balance loss, in which:

(a) a therapeutically effective amount of one or more agents that promote proliferation of inner ear supporting cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; and (v) an E box-dependent transcriptional activator set forth in Table D; and/or (b) a therapeutically effective amount of one or more agents that promote differentiation of inner ear supporting cells into inner ear hair cells selected from the group consisting of: (i) a Wnt signaling activator set forth in Table A; (ii) an E box-dependent transcriptional activator set forth in Table D; (iii) an HDAC inhibitor set forth in Table F; (iv) a protein degradation inhibitor set forth in Table G; and (v) a Notch signaling inhibitor set forth in Table J, are administered to the subject, e.g., to the ear of a subject, to promote inner ear supporting cells (e.g., Lgr5+ inner ear supporting cells) proliferation and/or differentiation of inner ear supporting cells (e.g., Lgr5+ inner ear supporting cells) into inner ear hair cells (e.g., Atoh1+ inner ear hair cells).

In some embodiments of the methods of treating a subject having hearing loss or balance loss, the one or more agents are administered systemically or to the ear of the subject, e.g., transtympanically to the middle ear of the subject. In some embodiments, the one or more agents that promote proliferation of inner ear supporting cells (e.g., Lgr5+ inner ear supporting cells) are administered prior to the one or more agents that promote differentiation of inner ear supporting cells (e.g., Lgr5+ inner ear supporting cells) into inner ear hair cells (e.g., Atoh1+ inner ear hair cells).

The present disclosure also provides methods of treating a subject having hearing loss or balance loss by:

(a) contacting one or more inner ear supporting cells, e.g., in vitro, with one or more agents that promote proliferation of inner ear supporting cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; (v) an E box-dependent transcriptional activator set forth in Table D; (vi) a Notch signaling activator set forth in Table E; (vii) an HDAC inhibitor set forth in Table F; (viii) a protein degradation inhibitor set forth in Table G; (ix) a PI3K-Akt signaling inhibitor set forth in Table H; and (x) a CREB activator set forth in Table I;

(b) optionally contacting the expanded population of inner ear supporting cells with one or more agents that promote differentiation of inner ear supporting cells into inner ear hair cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; (v) an E box-dependent transcriptional activator set forth in Table D; (vi) an HDAC inhibitor set forth in Table F; (vii) a protein degradation inhibitor set forth in Table G; (viii) a PI3K-Akt signaling inhibitor set forth in Table H; (ix) a CREB activator set forth in Table I; and (x) a Notch signaling inhibitor set forth in Table J; and (c) administering the inner ear hair cells to the ear (e.g., the inner ear) of the subject.

The present disclosure also provides methods of treating a subject having hearing loss or balance loss by:

(a) contacting one or more inner ear supporting cells, e.g., in vitro, with one or more agents that promote proliferation of inner ear supporting cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; (v) an E box-dependent transcriptional activator set forth in Table D; (vi) a Notch signaling activator set forth in Table E; (vii) an HDAC inhibitor set forth in Table F; (viii) a protein degradation inhibitor set forth in Table G; (ix) a PI3K-Akt signaling inhibitor set forth in Table H; and (x) a CREB activator set forth in Table I; and (b) administering the expanded population of inner ear supporting cells to the ear (e.g., the inner ear) of the subject in combination with, e.g., concurrently with or prior to administration of, one or more agents that promote differentiation of inner ear supporting cells into inner ear hair cells selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; (v) an E box-dependent transcriptional activator set forth in Table D; (vi) an HDAC inhibitor set forth in Table F; (vii) a protein degradation inhibitor set forth in Table G; (viii) a PI3K-Akt signaling inhibitor set forth in Table H; (ix) a CREB activator set forth in Table I; and (x) a Notch signaling inhibitor set forth in Table J.

In some embodiments of the methods of treating a subject having a hearing loss or a balance loss described herein, (a) the one or more agents that promote proliferation of inner ear supporting cells is selected from the group consisting of: (i) a retinoid receptor signaling activator; (ii) a Wnt signaling activator set forth in Table A; (iii) a BMP signaling inhibitor set forth in Table B; (iv) a CDK activator set forth in Table C; and (v) an E box-dependent transcriptional activator set forth in Table D; and (b) the one or more agents that promote differentiation of inner ear supporting cells into inner ear hair cells is selected from the group consisting of: (i) a Wnt signaling activator set forth in Table A; (ii) an E box-dependent transcriptional activator set forth in Table D; (iii) an HDAC inhibitor set forth in Table F; (iv) a protein degradation inhibitor set forth in Table G; and (v) a Notch signaling inhibitor set forth in Table J.

In some embodiments, the retinoid receptor signaling activator is an RAR agonist set forth in Table K or an RXR agonist set forth in Table K. In some embodiments, the inner ear supporting cells are Lgr5+ inner ear supporting cells. In some embodiments, the inner ear hair cells are Atoh1+ inner ear hair cells.

In some embodiments of the methods of treating a subject described herein, the subject has a balanced loss. In some embodiments of the methods of treating a subject described herein, the subject has hearing loss (e.g., sensorineural hearing loss). In some embodiments, the hearing loss is the result of a genetic or congenital defect, trauma, aging, or chemical-induced ototoxicity.

In some embodiments of the methods of treating a subject described herein, the subject is a human.

In general, compounds and methods described herein can be used to generate hair cell growth (e.g., Atoh1+ inner ear hair cell growth) in the ear and/or to increase the number of hair cells in the ear (e.g., in the inner, middle, and/or outer ear). For example, the number of hair cells in the ear can be increased about 2-, 3-, 4-, 6-, 8-, or 10-fold, or more, as compared to the number of hair cells before treatment. This new hair cell growth can effectively restore or establish at least a partial improvement in the subject's ability to hear. For example, administration of an agent can improve hearing loss by about 5, 10, 15, 20, 40, 60, 80, 100% or more.

A number of compounds that support or promote the proliferation of inner ear supporting cells (e.g., Lgr5+ inner ear supporting cells) and/or promote the differentiation of inner ear supporting cells (e.g., Lgr5+ inner ear supporting cell) into inner ear hair cells (e.g., Atoh1+ inner ear hair cells) are set forth in Table 1.

A number of compounds that support or promote the proliferation of inner ear supporting cells (e.g., Lgr5+ inner ear supporting cells) are described herein, and include one or more of TTNPB, Compound A, Compound B, Compound C, 1-Azakenpaullone, BIO, WAY-316606, LDN-193189, and Alsterpaullone.

A number of compounds that promote the differentiation of inner ear supporting cells (e.g., Lgr5+ inner ear supporting cell) into to inner ear hair cells (e.g., Atoh1+ inner ear hair cells) are described herein, and include one or more of vorinostat, Compound A, Compound B, Compound C, 1-Azakenpaullone, BIO, WAY-262611, NP031112, MG-132, IM-12, Trichostatin A, HLY78, and PF03084014.

Other examples of compounds that promote the proliferation and expansion of inner ear supporting cells (e.g., Lgr5+ inner ear supporting cells) include, but are not limited to, a retinoid receptor signaling activator (see, e.g., Table K); a Wnt signaling activator set forth in Table A; a bone morphogenetic protein (BMP) signaling inhibitor set forth in Table B; a cyclin-dependent kinase (CDK) activator set forth in Table C; an E box-dependent transcriptional activator set forth in Table D; a Notch signaling activator set forth in Table E; a histone deacetylase (HDAC) inhibitor set forth in Table F; a protein degradation inhibitor set forth in Table G; a PI3K-Akt signaling inhibitor set forth in Table H; and a cAMP response element binding protein (CREB) activator set forth in Table I.

Other examples of compounds that promote the differentiation of inner ear supporting cells (e.g., Lgr5+ inner ear supporting cells) into inner ear hair cells (e.g., Atoh1+ inner ear hair cells) include, but are not limited to, a retinoid receptor signaling activator (see, e.g., Table K); a Wnt signaling activator set forth in Table A; a BMP signaling inhibitor set forth in Table B; a CDK activator set forth in Table C; an E box-dependent transcriptional activator set forth in Table D; an HDAC inhibitor set forth in Table F; a protein degradation inhibitor set forth in Table G; a PI3K-Akt signaling inhibitor set forth in Table H; a CREB activator set forth in Table I; and a Notch signaling inhibitor set forth in Table J.

Where appropriate, following treatment, a human can be tested for an improvement in hearing or in other symptoms related to inner ear disorders. Methods for measuring hearing are well-known and include pure tone audiometry, air conduction, and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Oto-acoustic emission testing can be used to test the functioning of the cochlea hair cells, and electro-cochleography provides information about the functioning of the cochlea and the first part of the nerve pathway to the brain. In some embodiments, treatment can be continued with or without modification or can be stopped.

Pharmaceutical Compositions

In some embodiments, one or more compounds for the promotion of proliferation and/or differentiation of inner ear supporting cells (e.g., Lgr5+ inner ear supporting cells) as described herein can be formulated as a pharmaceutical composition. Pharmaceutical compositions containing one or more compounds as described herein can be formulated according to the intended method of administration.

One or more compounds for the promotion of proliferation and/or differentiation of inner ear supporting cells (e.g., Lgr5+ inner ear supporting cells) as described herein can be formulated as pharmaceutical compositions for direct administration to a subject. Pharmaceutical compositions containing one or more compounds can be formulated in a conventional manner using one or more physiologically acceptable carriers or excipients. For example, a pharmaceutical composition can be formulated for local or systemic administration, e.g., administration by drops (e.g., otic drops) or injection into the ear, insufflation (such as into the ear), intravenous, topical, or oral administration.

The nature of the pharmaceutical compositions for administration is dependent on the mode of administration and can readily be determined by one of ordinary skill in the art. In some embodiments, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral.

A pharmaceutical composition can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, *Remington: The Science and Practice of Pharmacy*, 22$^{nd}$ Ed., Allen, ed., Mack Publishing Co., Easton, Pa., 2012.

One or more of the compounds can be administered, e.g., as a pharmaceutical composition, directly and/or locally by injection or through surgical placement, e.g., to the inner ear. The amount of the pharmaceutical composition may be described as the effective amount or the amount of a cell-based composition may be described as a therapeutically effective amount. Where application over a period of time is advisable or desirable, the compositions of the invention can be placed in sustained released formulations or implantable devices (e.g., a pump).

Alternatively or in addition, the pharmaceutical compositions can be formulated for systemic parenteral administration by injection, for example, by bolus injection or continuous infusion. Such formulations can be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

In addition to the formulations described previously, the compositions can also be formulated as a depot preparation. Such long acting formulations can be administered by implantation (e.g., subcutaneously). Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions formulated for systemic oral administration can take the form of tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

In some embodiments, the pharmaceutical compositions described herein can include one or more of the compounds formulated according to any of the methods described above, and one or more cells obtained to the methods described herein.

EXAMPLES

The invention is further described in the following examples, which do not limit the scope of the invention described in the claims.

Example 1. Drug Screening for Agents that Promote Proliferation and Differentiation Two mouse strains were used to develop a screen for agents that promote the proliferation or differentiation of Lgr5-expressing cells. Each strain contained a fluorescent marker for the either the detection of Lgr5 expressing cells or Atoh1 expressing hair cells. Lgr5-EGFP-IRES-Cre-ER mice were used to monitor the proliferation of Lgr5+ cells (Barker, N. et al. Identification of stem cells in small intestine and colon by marker gene Lgf5. *Nature* 449, 1003-1007 (2007)). This strain was then crossed with Rosa26-td-Tomato reporter mice (Madisen, L. et al. A robust and high-throughput Cre reporting and characterization system for the whole mouse brain. *Nat Neurosci* 13, 133-140 (2010)) to create a mouse line that enabled lineage tracing of the cells that resulted from differentiated Lgr5-expressing cells. Atoh1-nGFP mice were used to identify differentiated hair cells (Lumpkin, E. A. et al. Math1-driven GFP expression in the developing nervous system of transgenic mice. *Gene Expr Patterns* 3, 389-395 (2003)).

Lgr5+ cells from both the Lgr5-GFP+ and Atoh1-GFP+ reporter mice were obtained as follows. *Cochleae* from neonatal mice (postnatal days 1-3) were dissected in HBSS and the organ of Corti was separated from the stria vascularis and the modiolus. The organs of Corti were then treated with Cell Recovery Solution (Corning) for 1 hour to separate cochlear epithelium from the underlying mesenchyme. Epithelia were then collected and treated with TryPLE (Life Technologies) for 15-20 minutes at 37° C. Single cells obtained by mechanical trituration were filtered (40 µm) and suspended in Matrigel for 3D culture. Matrigel is a reconstituted basement membrane preparation extracted from the Engelbreth-Holm-Swarm (EHS) mouse sarcoma, a tumor rich in extracellular matrix proteins, and is approximately 60% laminin, 30% collagen IV, and 8% entactin. The resulting cells were separately cultured in 24 well plates for 5 days at a concentration of 1 cochlea per well using 1:1 mixture of DMEM and F12, supplemented with Glutamax (GIBCO), N2, B27 (Invitrogen), EGF (50 ng/mL; Chemicon), bFGF (50 ng/mL; Chemicon), IGF1 (50 ng/mL; Chemicon) and small molecules including CHIR99021 (3 µM; LC Labs), VPA (1 mM; Sigma), pVc (100 µg/ml; Sigma), and 616452 (2 µM; Calbiochem). Media were changed every other day.

To assess the degree of proliferation of the Lgr5+ cells, 200 µl of cell dissociation solution was then added to each well of the Lgr5-GFP+ cells and incubated for 45 minutes and then TrypleE for 20 minutes. Cell cultures were then transferred to a 15 ml falcon tube for centrifugation. Supernatant was then removed and the cell culture was re-suspended in matrigel once again. Cells were distributed into a 96 well plate with approximately 5000 cells per well. The Lgr5-GFP+ cultures were then treated with DMEM/F12 media containing from nanomolar to micromolar concentrations, e.g., 0.001, 0.005 µM, 0.01 µM, 0.1 µM, 1 µM, 10 µM, 50 µM, or 100 µM, of a candidate drug for an additional 5 days (See FIG. 1). At that point the Lgr5-GFP+ cells were sorted using FACS and the fluorescence was measured (See FIGS. 3 and 4).

Figure 2:
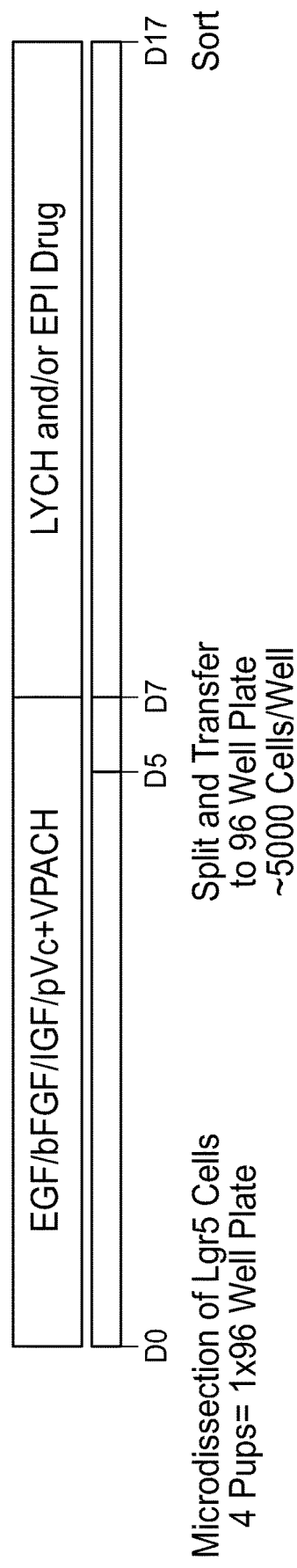
FIG. 2 is a timeline for the screening of Lgr5+ cells for drugs affecting differentiation.

To assess the degree of differentiation of the Lgr5+ cells into hair cells, the Atoh1-nGFP cells were cultured for 2 more days (a total of 7 days) in the DMEM/F12 media containing EGF, bFGF, IGF, pVc, VPA, and CHIR99021 (as above, a 1:1 mixture of DMEM and F12, supplemented with Glutamax (GIBCO), N2, B27 (Invitrogen), EGF (50 ng/mL; Chemicon), bFGF (50 ng/mL; Chemicon), IGF1 (50 ng/mL; Chemicon) and small molecules including CHIR99021 (3 µM), VPA (1 mM), pVc (100 µg/ml), and 616452 (2 µM). Media were changed every other day. 4-hydroxytamoxifen (20 ng/ml) was added to cultures on day 0 for lineage tracing studies) (See FIG. 2). After the 7-day incubation, 200 µl of cell dissociation solution was added to each well and incubated for 45 minutes and then TrypleE for 20 minutes. Cell cultures were then transferred to a 15 ml falcon tube for centrifugation. Supernatant was then removed and the cell culture was re-suspended in matrigel once again. Cells were distributed into a 96 well plate with approximately 5000 cells per well. The cells were then treated with DMEM/F12 media containing the candidate drug. After 10 days of incubating with the candidate drug, the cells were sorted by FACS and the fluorescence levels of the Atoh1-nGFP cells were measured (see FIG. 5). CHIR99021, a GSK-3β inhibitor of the Wnt pathway, and LY411575 a γ-secretase inhibitor of the Notch pathway were used as positive controls for this screen (see WO2014159356 and FIG. 5). This method of screening was used to screen drugs, compounds, genes, and growth factors (see Table 1).

TABLE 1

| Screening agents | |
| --- | --- |
| Name | Target |
| CHIR-99021 (6-(2-(4-(2,4-dichlorophenyl)-5-(4-methyl-1H-imidazol-2-yl)pyrimidin-2-ylamino)ethylamino)nicotinonitrile hydrochloride) | Wnt (GSK3β) |
| LY411575 (Benzeneacetamide, N-[(1S)-2-[[(7S)-6,7-dihydro-5-methyl-6-oxo-5H-dibenz[b,d]azepin-7-yl]amino]-1-methyl-2-oxoethyl]-3,5-difluoro-α-hydroxy-,(αS)-) | Notch (γ-Secretase) |
| Vorinostat (N1-hydroxy-N8-phenyl-octanediamide) | pan-HDAC |
| TTNPB (Ro 13-7410) (Arotinoid Acid) | RAR |
| Cerivastatin (sodium salt) (3R,5S,6E)-7-[4-(4-fluorophenyl)-5-(methoxymethyl)-2,6-bis(propan-2-yl)pyridin-3-yl]-3,5-dihydroxyhept-6-enoic acid) | P27 |
| Compound A (See FIG. 7) | ATOH1 |
| Compound B (See FIG. 7) | ATOH1 |
| Compound C (See FIG. 7) | ATOH1 |
| 1-Azakenpaullone | ATOH1 |
| (Pyrido[3',2':2,3]azepino[4,5-b]indol-6(5H)-one,9-bromo-7,12-dihydro-) | |
| (2'Z,3'E)-6-Bromoindirubin-3'-oxime (BIO) | Wnt (GSK3β) |
| MK-0752 (3-((1r,4s)-4-(4-chlorophenylsulfonyl)-4-(2,5-difluorophenyl)cyclohexyl)propanoic acid) | Notch (γ-Secretase) |
| WAY-262611 ((1-(4-(Naphthalen-2-yl)pyrimidin-2-yl)piperidin-4-yl)methanamine) | Wnt (β-catenin) |
| NP031112 (Tideglusib) (4-benzyl-2-naphthalen-1-yl-1,2,4-thiadiazolidine-3,5-dione) | Wnt (GSK3β) |
| WAY-316606 (5-(benzenesulfonyl)-N-piperidin-4-yl-2-(trifluoromethyl)benzenesulfonamide) | Wnt (sFRP-1) |
| LDN-193189 (4-(6-(4-(piperazin-1-yl)phenyl)pyrazolo[1,5-a]pyrimidin-3-yl)quinoline) | BMP receptor |
| Alsterpaullone, 2 Cyanoethyl (3-(9-nitro-6-oxo-7,12-dihydro-5H-indolo[3,2-d][1]benzazepin-2-yl)propanenitrile) | P27 (Kip1) |
| MLN4924 (pevonedistat) ([(1S,2S,4R)-4-[4-[[(1S)-2,3-dihydro-1H-inden-1-yl]amino]pyrrolo[2,3-d]pyrimidin-7-yl]-2-hydroxycyclopentyl]methyl sulfamate) | AKT |
| MG 132 (Carbobenzoxy-L-leucyl-L-leucyl-L-leucinal) | Proteosome Inhibitor |
| IM-12 (3-(4-Fluorophenylethylamino)-1-methyl-4-(2-methyl-1H-indol-3-yl)-1H-pyrrole-2,5-dione) | Wnt (GSK3β) |
| Trichostatin A ((2E,4E,6R)-7-[4-(dimethylamino)phenyl]-N-hydroxy-4,6-dimethyl-7-oxohepta-2,4-dienamide) | pan-HDAC |
| HLY78 (4-Ethyl-5,6-Dihydro-5-methyl-[1,3]dioxolo[4,5-j]phenanthridine,4-Ethyl-5-methyl-5,6-dihydro-[1,3]dioxolo[4,5-j]phenanthridine) | Wnt |
| DMHI (4-(6-(4-isopropoxyphenyl)pyrazolo[1,5-a]pyrimidin-3-yl)quinoline) | BMP1 |
| 2-(N)-benzyl ellipticene | ATOH1 |
| AC102 (6-Fluor-9-methyl-β-carbolin, see WO2015044434) | PKC/CREB |
| BI8622 (See FIG. 7) | HUWE1 |
| PF-03084014 ((S)-2-(((S)-6,8-difluoro-1,2,3,4-tetrahydronaphthalen-2-yl)amino)-N-(1-(2-methyl-1-(neopentylamino)propan-2-yl)-1H-imidazol-4-yl)pentanamide) | Notch (γ-Secretase) |

Figure 3:
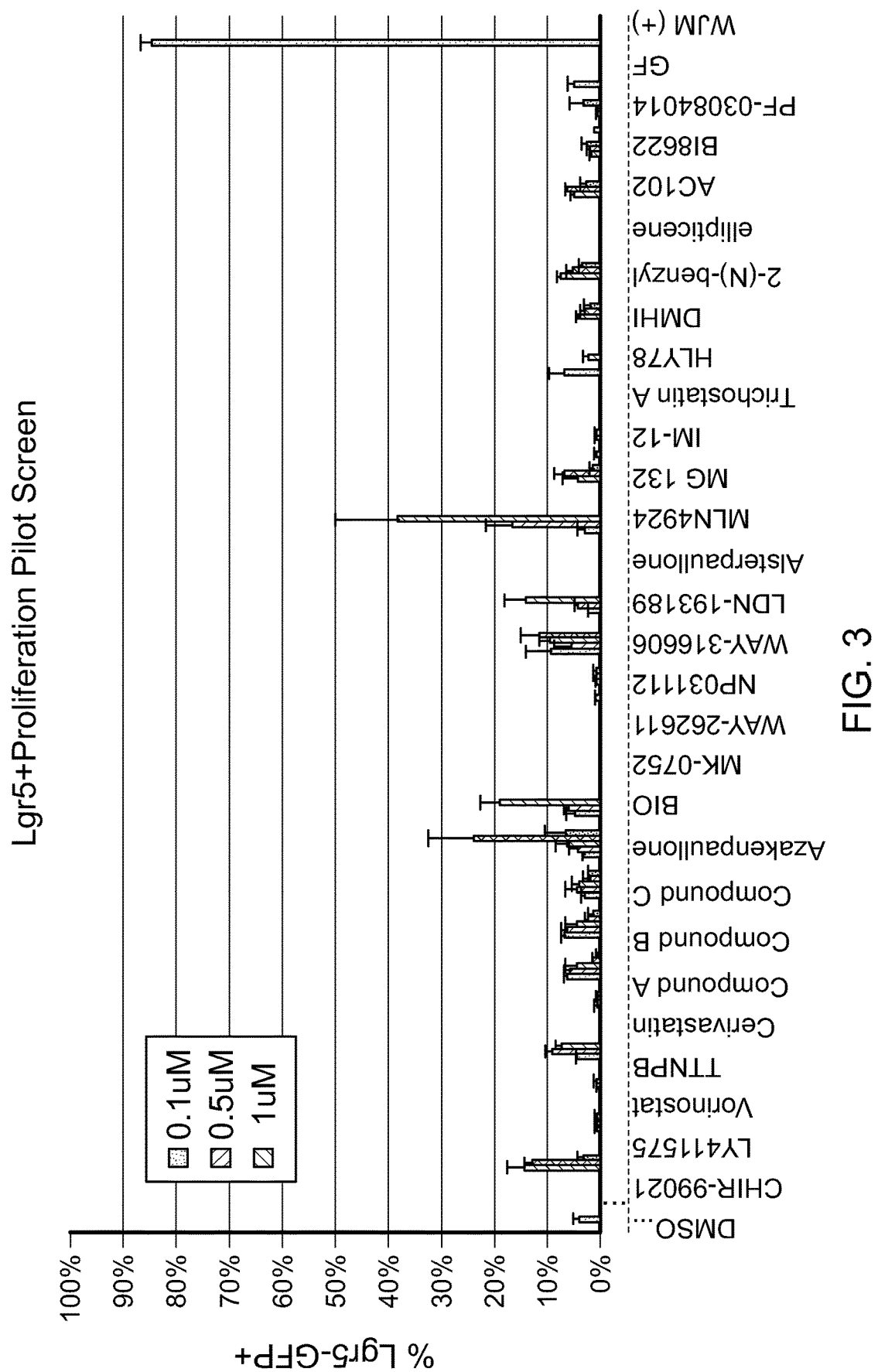
FIG. 3 is a graph depicting the percent of Lgr5-GFP+ cells from a screen for drugs that affect the proliferation of Lgr5-GFP cells. See Table 1 for a key to the compounds (WJM=CHIR 99021 and valproic acid).
Figure 4:
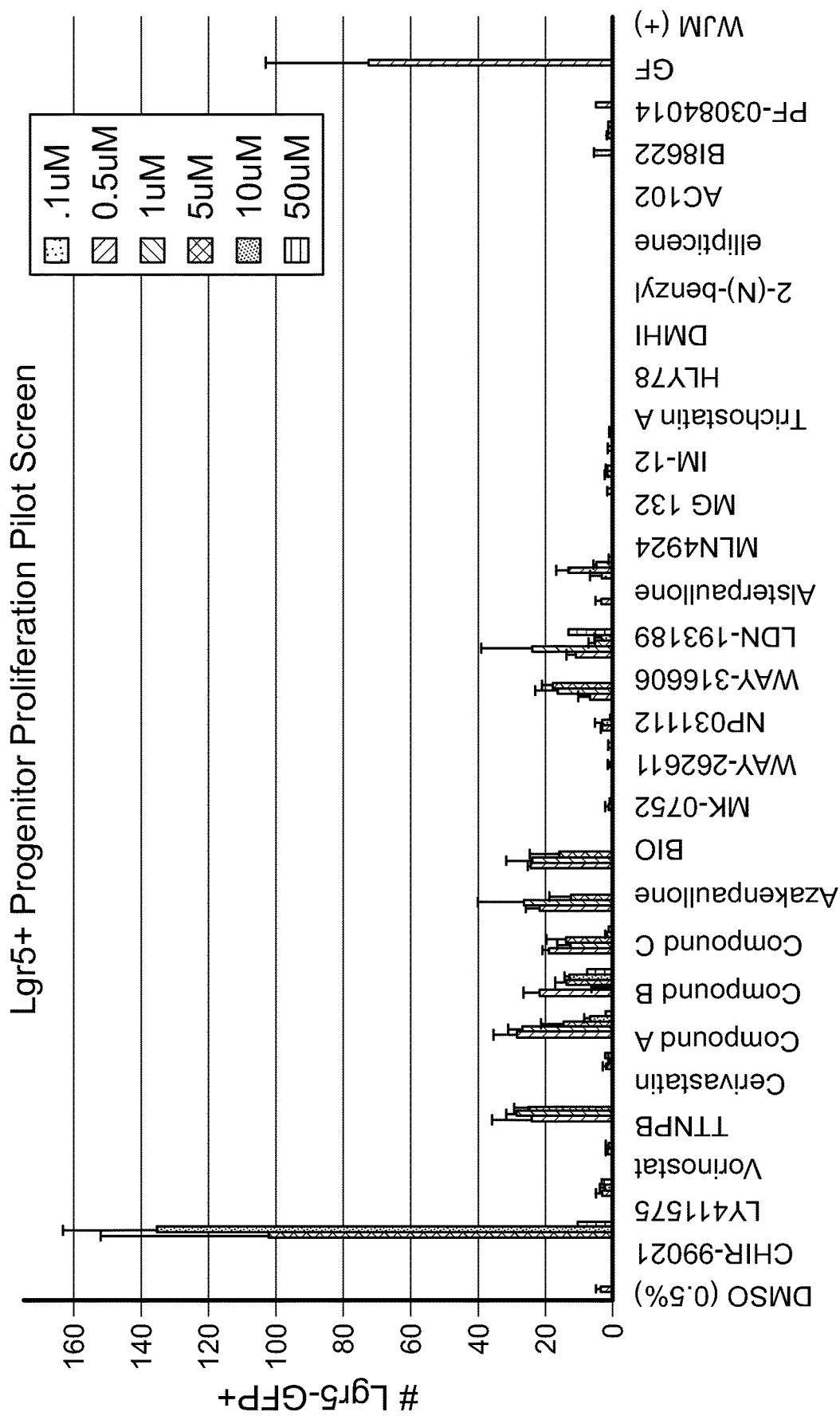
FIG. 4 is a graph depicting the number of Lgr5-GFP+ cells from a screen for drugs affecting proliferation of Lgr5-GFP cells. See Table 1 for a key to the compounds (WJM=CHIR 99021 and valproic acid).
Figure 5:
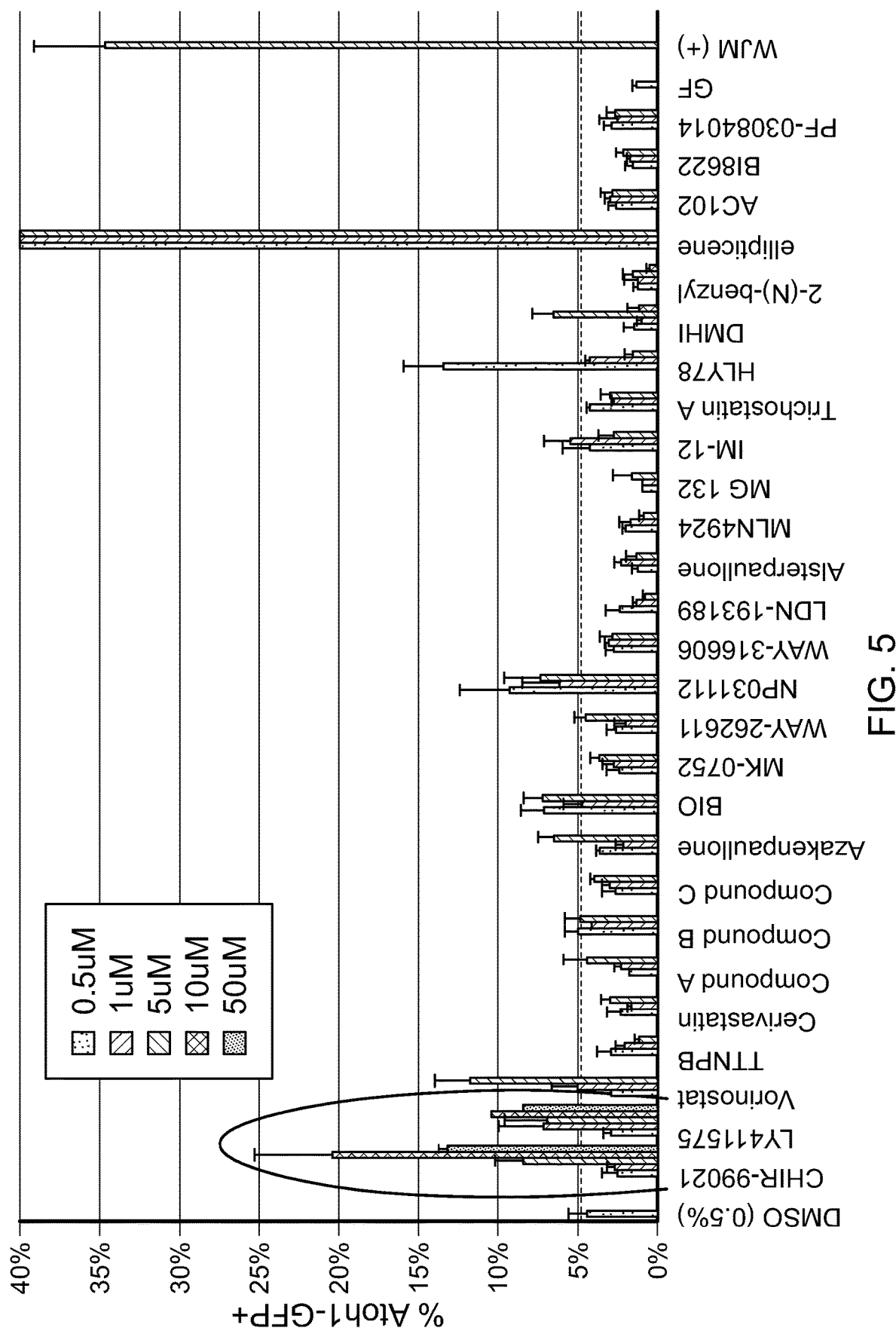
FIG. 5 is a graph depicting the percent of Atoh1-GFP+ cells from a screen for drugs that affect the differentiation of Atoh1-GFP+ cells. See Table 1 for a key to the compounds (WJM=CHIR 99021 and valproic acid).

The results, shown in FIGS. 3-5 showed that a number of compounds screened were able to effectively induce proliferation or differentiation. Tables 2 and 3 list the top compounds for proliferation and differentiation, respectively.

TABLE 2

Compounds selected for ability to enhance proliferation of Lgr5+ cells

| | |
|---|---|
| CHIR99021 | GSK3β inhibitor |
| TTNPB | retinoid acid receptor agonist |
| Compound A | Atoh1 stimulating compound |
| Compound B | Atoh1 stimulating compound |
| Compound C | Atoh1 stimulating compound |
| 1-Azakenpaullone | Atoh1 stimulating compound |
| BIO | GSK-3β inhibitor |
| WAY-316606 | sFRP-1 (secreted frizzled-related 1) inhibitor |
| LDN-193189 | BMP receptor inhibitor |
| Alsterpaullone, 2 Cyanoethyl | p27 Kip1 inhibitor |

TABLE 3

Compounds selected for ability to enhance differentiation of Lgr5+ cells into Atoh1+ cells

| | |
|---|---|
| CHIR99021 | GSK3β inhibitor |
| LY411575 | gamma-secretase inhibitor |
| vorinostat | class I, II and IV HDAc inhibitor |
| Compound A | Atoh1 stimulating compound |
| Compound B | Atoh1 stimulating compound |
| Compound C | Atoh1 stimulating compound |
| 1-Azakenpaullone | Atoh1 stimulating compound |
| BIO | GSK-3β inhibitor |
| WAY-262611 | dickopf inhibitor |
| NP031112 | GSK3β inhibitor |
| MG-132 | proteasome inhibitor |
| IM-12 | GSK3β inhibitor |
| Trichostatin A | class I and II HDAC inhibitor |
| HLY78 | Wnt signal transduction activator |
| PF03084014 | gamma-secretase inhibitor |

Figure 6:
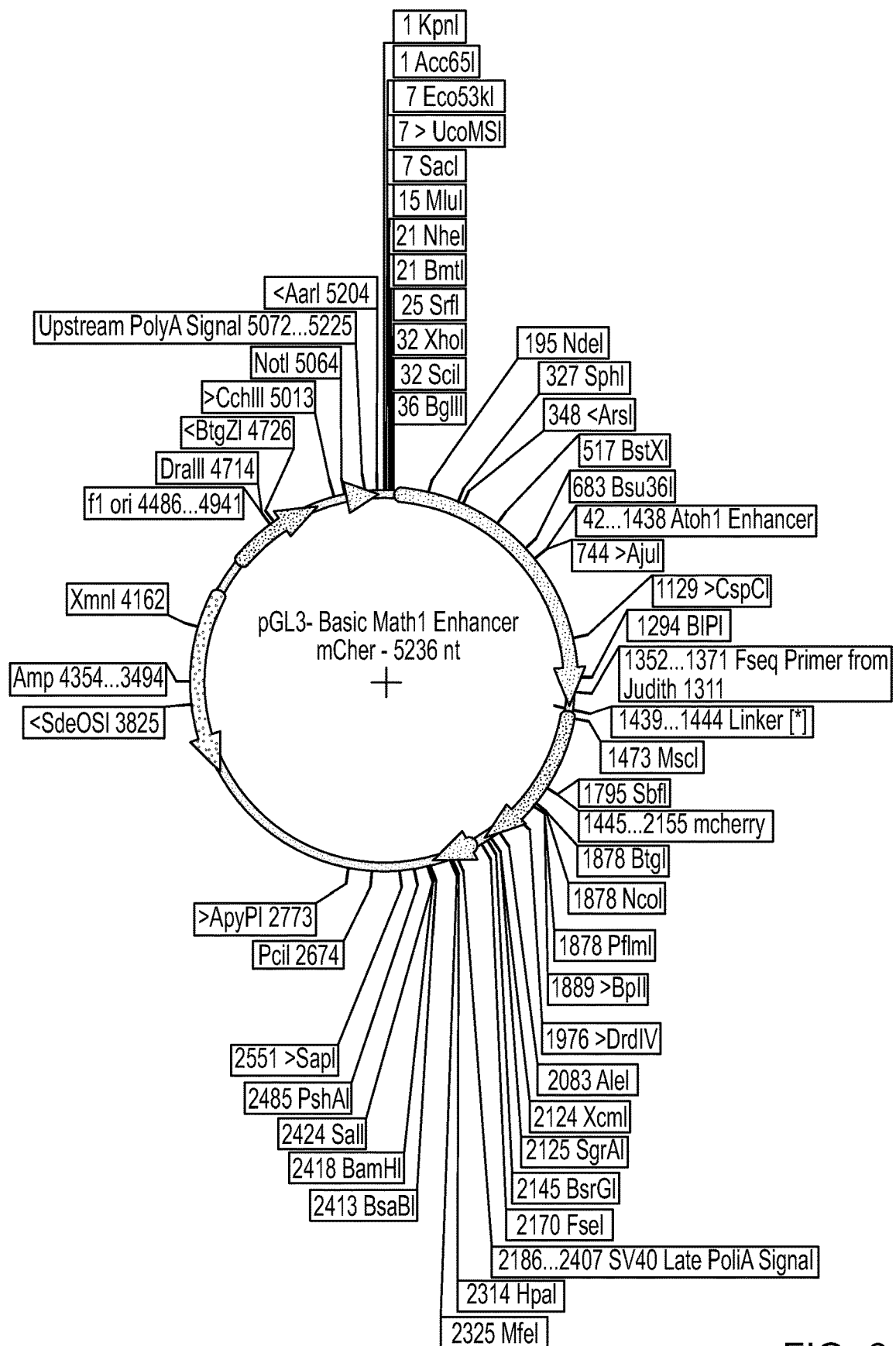
FIG. 6 is a schematic illustration of a plasmid for use in generating transgenic mice, in which mCherry fluorescent protein is under the control of an Atoh1 enhancer.

Example 2. Drug Screening for Agents for the Treatment of Hearing Loss Associated with the Loss of Cochlear Hair Cells A novel transgenic mouse is made that contains two florescent reporters stably integrated into the genome of the mouse (Lgr5/Atoh1 reporter mice). The Lgr5/Atoh1 reporter mice are made by starting with oocytes from a transgenic mouse that has GFP under the control of a Lgr5 promoter (Barker et al., supra) and adding a plasmid comprising mCherry under the control of an Atoh1 enhancer and a promoter (e.g., an SV40 or globin minimal promoter) (see FIG. 6).

The sequence of the Atoh1 enhancer used in these constructs is as follows:

(SEQ ID NO: 1)
```
TCCAAGGTCCGGCAATGAAGTTTGCATAACAAACGTTTGGCAGCTCCCTC
TCTCACACCCCATTAACAAGCTGTAACATATAGCTGCAGGTTGCTATAAT
CTCATTAATATTTTGGAAACTTGAATATTGAGTATTTCTGAGCGCTCATT
CCCCATATGCCAGACCACTCCTGCCATGCTGACTGGTTCCTTTCTCTCCA
TTATTAGCAATTAGCTTCTACCTTCCAAAGTCAGATCCAAGTATCTAAGA
TACTACCAAAGGCATCAACTATGTATGCAAGTTAGGCATGCTTAATATCA
CCCAAACAAACAAAGAGTCAGCACTTCTTAAAGTAATGAAGATAGATAAA
TCGGGTTAGTTCTTTGGGACACCGCTGTTGTTTTCCAGAGTTTTTCTATA
CTTTAAGCAGCTTGTTTTATATTCTGTCTTTGCCCTCAGCCAGCTAACAT
TTTATTTGTTGAGGGTTTTGGCTCACCACACTTTTGGAAACTTATTTGAT
TTCACGGGGAGCTGAAGGAAGATTGTTTTTGGCAACAGGCAAGTTTAACA
CGTTCTTCATGGGGCATTGCGAATGGCACATCTACCAGAAAGGGAGGGGG
AGTAACTTCCTCGTGCTGAACCAGCAGGAGACCAGAGCTTTCCTGAGGTC
TTCCTATTGATTTTAAAGATTTAAAACTGAGCCCCAAAGTTGTAATGTTA
TTGAAGTTTGTCTTGGAATATACATCTCCTCTGCTAACTTAAAAGTTCAA
GAAAGGAAAGGAAAGAAATAGAACCCCTTGCTAACTACAACCTAGACTGA
GAGGTGAAGATCGCGGGCAAAGACAGGTGGTCACTGAAACGTTTGCAGTT
CTTTTCTTCCGAAGGCTTAGGACACAGGGTAAGGAGGAGCTAAAATAAAG
CCGAGTGTACGTTTAGTCTTCTCTGCACCCCAGGCCTAGTGTCTCCCCAG
GCAAGGAGTCACCCCCTTTGCTTCTGGCTCCTAACTGAAAAAGGCAAAAG
GGAGTGGAGAATGGGTTAAATCCCAGGACACAGGGGAGAGGCAGGGGAGG
AGAGAAGTCGGAGGAAGATAAAGGAAAGGACAGGAACCAAGAAGCGTGGG
GGTAGTTTGCCGTAATGTGAGTGTTTCTTAATTAGAGAGCGGCTGACAAT
AGAGGGGCTGGCAGAGGCTCCTGGCCCCGGTGCGGAGCGTCTGGAGCGGA
GCACGCGCTGTCAGCTGGTGAGCGCACTCGCTTTCAGGCCGCTCCCCGGG
GAGCTGAGCGGCCACATTTAACACCGTCGTCACCCTCCCCGGCCTCCTCA
ACATCGGCCTCCTCCTCGTAGACAGCCTTGCTCGGCCCCCCACCGGCAGA
GTTTACAGAAGCCAGAGCCTCTCGCCGTTCCCCCGCATTCGCCCGGG
```

The sequence of the Atoh1-mCherry plasmid is as follows:

(SEQ ID NO: 2)
```
GGTACCGAGCTCTTACGCGTGCTAGCCCGGGCTCGAGATCTTCCAAGGTC
CGGCAATGAAGTTTGCATAACAAACGTTTGGCAGCTCCCTCTCTCACACC
CCATTAACAAGCTGTAACATATAGCTGCAGGTTGCTATAATCTCATTAAT
ATTTTGGAAACTTGAATATTGAGTATTTCTGAGCGCTCATTCCCCATATG
CCAGACCACTCCTGCCATGCTGACTGGTTCCTTTCTCTCCATTATTAGCA
ATTAGCTTCTACCTTCCAAAGTCAGATCCAAGTATCTAAGATACTACCAA
AGGCATCAACTATGTATGCAAGTTAGGCATGCTTAATATCACCCAAACAA
ACAAAGAGTCAGCACTTCTTAAAGTAATGAAGATAGATAAATCGGGTTAG
TTCTTTGGGACACCGCTGTTGTTTTCCAGAGTTTTTCTATACTTTAAGCA
GCTTGTTTTATATTCTGTCTTTGCCCTCAGCCAGCTAACATTTTATTTGT
TGAGGGTTTTGGCTCACCACACTTTTGGAAACTTATTTGATTTCACGGGG
AGCTGAAGGAAGATTGTTTTTGGCAACAGGCAAGTTTAACACGTTCTTCA
TGGGGCATTGCGAATGGCACATCTACCAGAAAGGGAGGGGGAGTAACTTC
CTCGTGCTGAACCAGCAGGAGACCAGAGCTTTCCTGAGGTCTTCCTATTG
ATTTTAAAGATTTAAAACTGAGCCCCAAAGTTGTAATGTTATTGAAGTTT
GTCTTGGAATATACATCTCCTCTGCTAACTTAAAAGTTCAAGAAAGGAAA
GGAAAGAAATAGAACCCCTTGCTAACTACAACCTAGACTGAGAGGTGAAG
ATCGCGGGCAAAGACAGGTGGTCACTGAAACGTTTGCAGTTCTTTTCTTC
```

-continued

CGAAGGCTTAGGACACAGGGTAAGGAGGAGCTAAAATAAAGCCGAGTGTA
CGTTTAGTCTTCTCTGCACCCCAGGCCTAGTGTCTCCCCAGGCAAGGAGT
CACCCCCTTTGCTTCTGGCTCCTAACTGAAAAAGGCAAAAGGGAGTGGAG
AATGGGTTAAATCCCAGGACACAGGGGAGAGGCAGGGGAGGAGAGAAGTC
GGAGGAAGATAAAGGAAAGGACAGGAACCAAGAAGCGTGGGGGTAGTTTG
CCGTAATGTGAGTGTTTCTTAATTAGAGAGCGGCTGACAATAGAGGGGCT
GGCAGAGGCTCCTGGCCCCGGTGCGGAGCGTCTGGAGCGGAGCACGCGCT
GTCAGCTGGTGAGCGCACTCGCTTTCAGGCCGCTCCCCGGGGAGCTGAGC
GGCCACATTTAACACCGTCGTCACCCTCCCCGGCCTCCTCAACATCGGCC
TCCTCCTCGTAGACAGCCTTGCTCGGCCCCCCACCGGCAGAGTTTACAGA
AGCCAGAGCCTCTCGCCGTTCCCCCGCATTCGCCCGGGTCTAGAATGGTG
AGCAAGGGCGAGGAGGATAACATGGCCATCATCAAGGAGTTCATGCGCTT
CAAGGTGCACATGGAGGGCTCCGTGAACGGCCACGAGTTCGAGATCGAGG
GCGAGGGCGAGGGCCGCCCCTACGAGGGCACCCAGACCGCCAAGCTGAAG
GTGACCAAGGGTGGCCCCCTGCCCTTCGCCTGGGACATCCTGTCCCCTCA
GTTCATGTACGGCTCCAAGGCCTACGTGAAGCACCCCGCCGACATCCCCG
ACTACTTGAAGCTGTCCTTCCCCGAGGGCTTCAAGTGGGAGCGCGTGATG
AACTTCGAGGACGGCGGCGTGGTGACCGTGACCCAGGACTCCTCCCTGCA
GGACGGCGAGTTCATCTACAAGGTGAAGCTGCGCGGCACCAACTTCCCCT
CCGACGGCCCCGTAATGCAGAAGAAGACCATGGGCTGGGAGGCCTCCTCC
GAGCGGATGTACCCCGAGGACGGCGCCCTGAAGGGCGAGATCAAGCAGAG
GCTGAAGCTGAAGGACGGCGGCCACTACGACGCTGAGGTCAAGACCACCT
ACAAGGCCAAGAAGCCCGTGCAGCTGCCCGGCGCCTACAACGTCAACATC
AAGTTGGACATCACCTCCCACAACGAGGACTACACCATCGTGGAACAGTA
CGAACGCGCCGAGGGCCGCCACTCCACCGGCGGCATGGACGAGCTGTACA
AGTAATCTAGAGTCGGGGCGGCCGGCCGCTTCGAGCAGACATGATAAGAT
ACATTGATGAGTTTGGACAAAACCACAACTAGAATGCAGTGAAAAAAATGC
TTTATTTGTGAAATTTGTGATGCTATTGCTTTATTTGTAACCATTATAAG
CTGCAATAAACAAGTTAACAACAACAATTGCATTCATTTTATGTTTCAGG
TTCAGGGGGAGGTGTGGGAGGTTTTTTAAAGCAAGTAAAACCTCTACAAA
TGTGGTAAAATCGATAAGGATCCGTCGACCGATGCCCTTGAGAGCCTTCA
ACCCAGTCAGCTCCTTCCGGTGGGCGCGGGCATGACTATCGTCGCCGCA
CTTATGACTGTCTTCTTTATCATGCAACTCGTAGGACAGGTGCCGGCAGC
GCTCTTCCGCTTCCTCGCTCACTGACTCGCTGCGCTCGGTCGTTCGGCTG
CGGCGAGCGGTATCAGCTCACTCAAAGGCGGTAATACGGTTATCCACAGA
ATCAGGGGATAACGCAGGAAAGAACATGTGAGCAAAAGGCCAGCAAAAGG
CCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAA
CCCGACAGGACTATAAAGATACCAGGCGTTTCCCCCTGGAAGCTCCCTCG
TGCGCTCTCCTGTTCCGACCCTGCCGCTTACCGGATACCTGTCCGCCTTT
CTCCCTTCGGGAAGCGTGGCGCTTTCTCATAGCTCACGCTGTAGGTATCT

CAGTTCGGTGTAGGTCGTTCGCTCCAAGCTGGGCTGTGTGCACGAACCCC
CCGTTCAGCCCGACCGCTGCGCCTTATCCGGTAACTATCGTCTTGAGTCC
AACCCGGTAAGACACGACTTATCGCCACTGGCAGCAGCCACTGGTAACAG
GATTAGCAGAGCGAGGTATGTAGGCGGTGCTACAGAGTTCTTGAAGTGGT
GGCCTAACTACGGCTACACTAGAAGAACAGTATTTGGTATCTGCGCTCTG
CTGAAGCCAGTTACCTTCGGAAAAAGAGTTGGTAGCTCTTGATCCGGCAA
ACAAACCACCGCTGGTAGCGGTGGTTTTTTTGTTTGCAAGCAGCAGATTA
CGCGCAGAAAAAAAGGATCTCAAGAAGATCCTTTGATCTTTTCTACGGGG
TCTGACGCTCAGTGGAACGAAAACTCACGTTAAGGGATTTTGGTCATGAG
ATTATCAAAAAGGATCTTCACCTAGATCCTTTTAAATTAAAAATGAAGTT
TTAAATCAATCTAAAGTATATATGAGTAAACTTGGTCTGACAGTTACCAA
TGCTTAATCAGTGAGGCACCTATCTCAGCGATCTGTCTATTTCGTTCATC
CATAGTTGCCTGACTCCCCGTCGTGTAGATAACTACGATACGGGAGGGCT
TACCATCTGGCCCCAGTGCTGCAATGATACCGCGAGACCCACGCTCACCG
GCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTT
GCCATTGCTACAGGCATCGTGGTGTCACGCTCGTCGTTTGGTATGGCTTC
ATTCAGCTCCGGTTCCCAACGATCAAGGCGAGTTACATGATCCCCCATGT
TGTGCAAAAAAGCGGTTAGCTCCTTCGGTCCTCCGATCGTTGTCAGAAGT
AAGTTGGCCGCAGTGTTATCACTCATGGTTATGGCAGCACTGCATAATTC
TCTTACTGTCATGCCATCCGTAAGATGCTTTTCTGTGACTGGTGAGTACT
CAACCAAGTCATTCTGAGAATAGTGTATGCGGCGACCGAGTTGCTCTTGC
CCGGCGTCAATACGGGATAATACCGCGCCACATAGCAGAACTTTAAAAGT
GCTCATCATTGGAAAACGTTCTTCGGGGCGAAAACTCTCAAGGATCTTAC
CGCTGTTGAGATCCAGTTCGATGTAACCCACTCGTGCACCCAACTGATCT
TCAGCATCTTTTACTTTCACCAGCGTTTCTGGGTGAGCAAAAACAGGAAG
GCAAAATGCCGCAAAAAAGGGAATAAGGGCGACACGGAAATGTTGAATAC
TCATACTCTTCCTTTTTCAATATTATTGAAGCATTTATCAGGGTTATTGT
CTCATGAGCGGATACATATTTGAATGTATTTAGAAAAATAAACAAATAGG
GGTTCCGCGCACATTTCCCCGAAAAGTGCCACCTGACGCGCCCTGTAGCG
GCGCATTAAGCGCGGCGGGTGTGGTGGTTACGCGCAGCGTGACCGCTACA
CTTGCCAGCGCCCTAGCGCCCGCTCCTTTCGCTTTCTTCCCTTCCTTTCT
CGCCACGTTCGCCGGCTTTCCCCGTCAAGCTCTAAATCGGGGGCTCCCTT
TAGGGTTCCGATTTAGTGCTTTACGGCACCTCGACCCCAAAAAACTTGAT
TAGGGTGATGGTTCACGTAGTGGGCCATCGCCCTGATAGACGGTTTTTCG
CCCTTTGACGTTGGAGTCCACGTTCTTTAATAGTGGACTCTTGTTCCAAA
CTGGAACAACACTCAACCCTATCTCGGTCTATTCTTTTGATTTATAAGGG
ATTTTGCCGATTTCGGCCTATTGGTTAAAAAATGAGCTGATTTAACAAAA
ATTTAACGCGAATTTTAACAAAATATTAACGCTTACAATTTGCCATTCGC

-continued
CATTCAGGCTGCGCAACTGTTGGGAAGGGCGATCGGTGCGGGCCTCTTCG

CTATTACGCCAGCCCAAGCTACCATGATAAGTAAGTAATATTAAGGTACG

GGAGGTACTTGGAGCGGCCGCAATAAAATATCTTTATTTTCATTACATCT

GTGTGTTGGTTTTTTGTGTGAATCGATAGTACTAACATACGCTCTCCATC

AAAACAAAACGAAACAAAACAAACTAGCAAAATAGGCTGTCCCCAGTGCA

AGTGCAGGTGCCAGAACATTTCTCTATCGATACATA

Stem cells from this mouse are isolated from the inner ear, suspended in matrigel and cultured in DMEM/F12 media containing EFG, bFGF, IGF, pVc and VPACHIR in a 24 well plate for up to 5 days. After 5 days, 200 μl of cell dissociation solution is added to each well and incubated for 45 minutes and then TrypleE for 20 minutes. Cell cultures are then transferred to a 15 ml falcon tube for centrifugation. Supernatant is then removed and the cell culture is re-suspended in matrigel once again. Cells are then distributed into a 96 well plate with approximately 5000 cells per well.

The cell culture is then treated with DMEM/F12 media containing a candidate drug for an addition 5-7 days. At that point the cells are sorted using FACS and the fluorescence of both markers is measured. Those candidate drugs that increase the fluorescence of both markers in the transgenic mouse cells when compared to an untreated transgenic control cell are selected as candidate agents for the treatment of hearing loss associated with the loss of cochlear hair cells (e.g., cochlear hair cells in the inner ear). This method of screening is used to screen drugs, compounds, genes, or growth factors.

REFERENCES

1. Cox, B. C. et al. Spontaneous hair cell regeneration in the neonatal mouse cochlea in vivo. Development 141, 816-829 (2014).
2. Fujioka, M., Okano, H. & Edge, A. S. Manipulating cell fate in the cochlea: a feasible therapy for hearing loss. Trends Neurosci (2015).
3. Davis, A. C. Hearing disorders in the population: first phase findings of the MRC National Study of Hearing. Hearing science and hearing disorders 35 (1983).
4. Chai, R. et al. Wnt signaling induces proliferation of sensory precursors in the postnatal mouse cochlea. Proc Natl Acad Sci USA 109, 8167-8172 (2012).
5. Shi, F., Kempfle, J. S. & Edge, A. S. Wnt-responsive lgr5-expressing stem cells are hair cell progenitors in the cochlea. J Neurosci 32, 9639-9648 (2012).
6. Shi, F., Hu, L. & Edge, A. S. Generation of hair cells in neonatal mice by beta-catenin overexpression in Lgr5-positive cochlear progenitors. Proc Natl Acad Sci USA 110, 13851-13856 (2013).
7. Shi, F., Cheng, Y. F., Wang, X. L. & Edge, A. S. Beta-catenin up-regulates Atoh1 expression in neural progenitor cells by interaction with an Atoh1 3' enhancer. J Biol Chem 285, 392-400 (2010).
8. Edge, A. S. & Chen, Z. Y. Hair cell regeneration. Curr Opin Neurobiol 18, 377-382 (2008).
9. Kelley, M. W. Regulation of cell fate in the sensory epithelia of the inner ear. Nat Rev Neurosci 7, 837-849 (2006).
10. Bramhall, N. F., Shi, F., Arnold, K., Hochedlinger, K. & Edge, A. S. Lgr5-positive supporting cells generate new hair cells in the postnatal cochlea. Stem Cell Reports 2, 311-322 (2014).
11. Oshima, K. et al. Differential distribution of stem cells in the auditory and vestibular organs of the inner ear. J Assoc Res Otolaryngol 8, 18-31 (2007).
12. Mizutari, K. et al. Notch inhibition induces cochlear hair cell regeneration and recovery of hearing after acoustic trauma. Neuron 77, 58-69 (2013).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject having hearing loss or balance loss, the method comprising administering to the subject in need thereof a therapeutically effective amount of a protein degradation inhibitor and a therapeutically effective amount of a Notch signaling inhibitor, wherein the protein degradation inhibitor is not Epigallocatechin-3-gallate.

2. The method of claim 1, wherein the protein degradation inhibitor and the Notch inhibitor are administered systemically or to the ear of the subject, preferably transtympanically to the middle ear of the subject.

3. The method of claim 1, wherein the subject has hearing loss.

4. The method of claim 3, wherein the hearing loss is sensorineural hearing loss.

5. The method of claim 3, wherein the hearing loss is the result of a genetic or congenital defect, trauma, aging, or chemical-induced ototoxicity.

6. The method of claim 1, wherein the subject is a human.

7. The method of claim 1, wherein the protein degradation inhibitor is selected from the group consisting of MG132, MG262, MG115, Z-Leu-Leu-Phe-CHO, N-Acetyl-leucyl-leucyl-norleucinal, N-acetyl-leucyl-leucyl-methional, N-benzyloxycarbonyl-isoleucyl-γ-t-butyl-glutamyl-alanyl-leucinal, N-benzyloxycarbonyl-leucyl-leucyl-leucinal, N-benzyloxycarbonyl-leucyl-leucyl-tyrosyl α-keto aldehyde, N-benzyloxycarbonyl-leucyl-leucyl-phenylalanal, N-benzyloxycarbonyl-leucyl-leucyl-leucyl boronic acid, Bortezomib, Lactacystin, Disulfiram, Salinosporamide A, Carfilzomib, epoxomicin, Ixazomib, ixazomib citrate, VLX1500 (b-AP15), clasto-Lactacystin beta Lactone, Gliotoxin, AM 114 (3,5-Bis-[benzylidene-4-boronic acid]-1-methylpiperidin-4-one), PSI (N-[(Phenylmethoxy)carbonyl]-L-isoleucyl-L-α-glutamyl-tert-butyl ester-N-[(1S)-1-formyl-3-methylbutyl]-alaninamide), Oprozomib, Delanzomib, BI8622, and BI8626.

8. The method of claim 1, wherein the Notch signaling inhibitor is selected from the group consisting of LY411575, L-685458, DBZ (Dibenzazepine), MRK560 (N-[cis-4-[(4-Chlorophenyl)sulfonyl]-4-(2,5-difluorophenyl)cyclohexyl]-1,1,1-trifluoromethanesulfonamide), MRK-003, MK-0752 (3-(((1r,4s)-4-(4-chlorophenylsulfonyl)-4-(2,5-difluorophenyl)cyclohexyl)propanoic acid), Compound W (3,5-Bis(4-nitrophenoxy)benzoic acid), Compound E (GSI-XXI), BMS 2289948, BMS-433796, IN973, Flurbiprofen, JLK2, JLK4, JLK6, JLK7, Begacestat, DFK167, and PF-0308414.

9. The method of claim 2, wherein the protein degradation inhibitor and the Notch inhibitor are administered transtympanically to the middle ear of the subject.

* * * * *

UNITED STATES PATENT AND TRADEMARK OFFICE
CERTIFICATE OF CORRECTION

PATENT NO. : 11,466,252 B2
APPLICATION NO. : 16/073701
DATED : October 11, 2022
INVENTOR(S) : Albert Edge, Michael Venuti and Agnieszka Czechowicz Page 1 of 1

It is certified that error appears in the above-identified patent and that said Letters Patent is hereby corrected as shown below:

In the Claims

In Column 55, Line 64-65, Claim 2, delete "subject, preferably transtympanically to the middle ear of the subject." and insert -- subject. --

In Column 57, Line 8, Claim 7, delete "methylbutyl]-alaninamide)," and insert -- methylbutyl]-L-alaninamide), --

In Column 57, Line 15, Claim 8, delete "(3-(((1r,4s)" and insert -- (3-((1r,4s) --

Signed and Sealed this
Twenty-fifth Day of April, 2023

Katherine Kelly Vidal
*Director of the United States Patent and Trademark Office*